US012453787B2

(12) United States Patent
Wurzer et al.

(10) Patent No.: US 12,453,787 B2
(45) Date of Patent: *Oct. 28, 2025

(54) DUAL MODE RADIOTRACER AND-THERAPEUTICS

(71) Applicants: Technische Universität München, Munich (DE); Technische Universität München—Klinikum Rechts der Isar, Munich (DE)

(72) Inventors: Alexander Josef Wurzer, Munich (DE); Hans-Jürgen Wester, Immünster (DE); Matthias Johannes Eiber, Vaterstetten (DE)

(73) Assignee: Technische Universität München and Technische Universität München—Klinikum Rechts der Isar, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/948,808

(22) Filed: Nov. 15, 2024

(65) Prior Publication Data

US 2025/0121102 A1 Apr. 17, 2025

Related U.S. Application Data

(63) Continuation of application No. 17/849,297, filed on Jun. 24, 2022, now Pat. No. 12,390,540, which is a continuation of application No. 16/634,759, filed as application No. PCT/EP2018/070533 on Jul. 30, 2018, now Pat. No. 11,413,360.

(30) Foreign Application Priority Data

Jul. 28, 2017 (EP) .................................... 17183795

(51) Int. Cl.
*A61K 51/04* (2006.01)

(52) U.S. Cl.
CPC ...... *A61K 51/0497* (2013.01); *A61K 51/0402* (2013.01); *A61K 51/0482* (2013.01)

(58) Field of Classification Search
CPC ............ A61K 51/0497; A61K 51/0402; A61K 51/0482; A61K 2121/00; A61K 2123/00; A61K 51/08; A61P 35/00
USPC ........................................................ 424/1.65
See application file for complete search history.

(56) References Cited

FOREIGN PATENT DOCUMENTS

| | | | |
|---|---|---|---|
| WO | WO-2019020831 A1 * | 1/2019 | ......... A61K 51/0402 |
| WO | WO-2019115547 A1 * | 6/2019 | ........... A61K 1/0482 |

OTHER PUBLICATIONS

Banerjee et al. Anqew. Chem. Int. Ed. 2011, 50-9167-9170. (Year: 2011).*
Bailey et al. J. Label Compd Radiopharm. 2017, 60 (suppl. 1), S353. (Year: 2017).*
Kratochwil et al. J Nucl. Med. 2016, 57, 1941-1944. (Year: 2016).*
Lindner et al. Bioconjugate Chem. 2014, 25, 718-749. (Year: 2014).*
STN RN 2271115-11-6, entered 2019, 1-2. (Year: 2019).*

* cited by examiner

*Primary Examiner* — Michael G. Hartley
*Assistant Examiner* — Sean R Donohue
(74) *Attorney, Agent, or Firm* — Min Yang

(57) ABSTRACT

The present invention relates to a ligand-SIFA-chelator conjugate, comprising, within in a single molecule three separate moieties: (a) one or more ligands which are capable of binding to a disease-relevant target molecule, (b) a silicon-fluoride acceptor (SIFA) moiety which comprises a covalent bond between a silicon atom and a fluorine atom, and (c) one or more chelating groups, optionally containing a chelated nonradioactive or radioactive cation.

7 Claims, 34 Drawing Sheets

Figure 1:
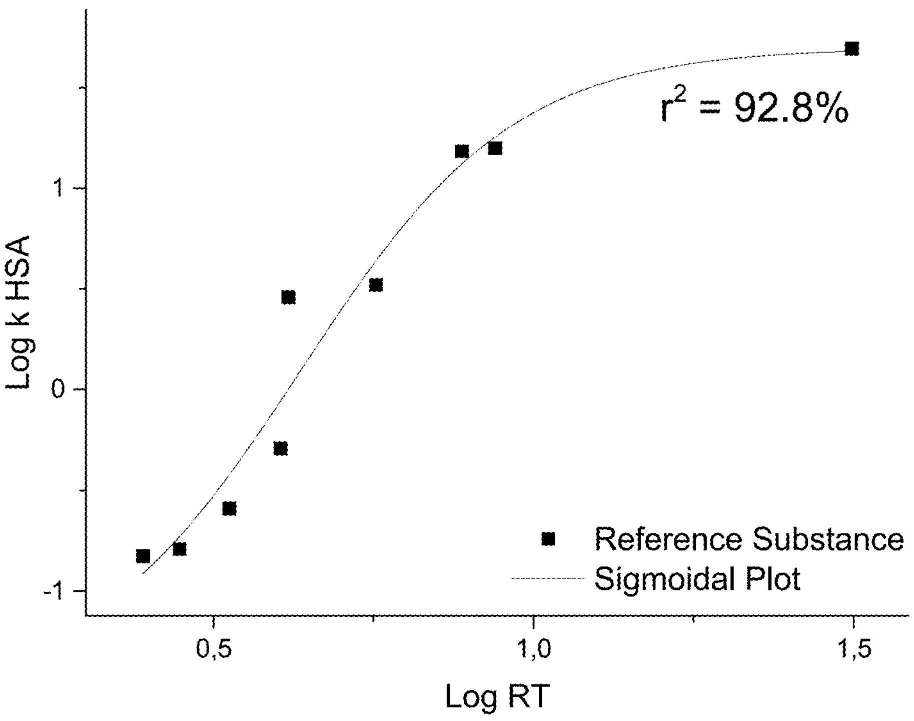

| organ | %ID/mL |
|---|---|
| tumor | 4. 8 ± 1.3 |
| salivary glands | 1.4 ± 0.17 |
| muscle | 0.58 ± 0.01 |
| kidney | 35.4 ± 7.9 |
| heart | 1.5 ± 0.11 |
| liver | 1.4 ± 0.12 |

| organ | %ID/mL |
|---|---|
| tumor | 4.0 ± 0.18 |
| salivary glands | 2.1 ± 0.25 |
| muscle | 0.57 ± 0.17 |
| kidney | 46.2 ± 6.1 |
| heart | 1.4 ± 0.29 |
| liver | 1.3 ± 0.27 |

| organ | %ID/mL |
|---|---|
| tumor | 8.3 ± 2.3 |
| salivary glands | 0.89 ± 0.12 |
| muscle | 0.29 ± 0.03 |
| kidney | 40.7 ± 2.3 |
| heart | 0.77 ± 0.05 |
| liver | 0.64 ± 0.02 |

| organ | %ID/mL |
|---|---|
| tumor | 11.0 ± 4.1 |
| salivary glands | 2.0 ± 1.4 |
| muscle | 0.68 ± 0.05 |
| kidney | 46.3 ± 13.1 |
| heart | 1.6 ± 0.17 |
| liver | 1.3 ± 0.17 |

| | $^{68}$Ga-$^{nat}$F -7 | $^{18}$F-7 |
|---|---|---|
| **blood** | 1.9 ± 0.14 | 1.9 ± 0.81 |
| **heart** | 1.2 ± 0.27 | 1.0 ± 0.40 |
| **lung** | 1.7 ± 0.16 | 2.0 ± 0.68 |
| **liver** | 0.77 ± 0.10 | 0.91 ± 0.21 |
| **spleen** | 13.8 ± 5.0 | 11.0 ± 2.9 |
| **pancreas** | 0.71 ± 0.11 | 0.55 ± 0.18 |
| **stomach** | 0.51 ± 0.07 | 0.66 ± 0.18 |
| **intestine** | 0.43 ± 0.07 | 0.67 ± 0.23 |
| **kidneys** | 34.1 ± 6.6 | 71.9 ± 6.8 |
| **adrenals** | 6.7 ± 2.2 | 14.6 ± 7.0 |
| **muscle** | 0.42 ± 0.22 | 0.37 ± 0.14 |
| **bone** | 0.52 ± 0.11 | 0.70 ± 0.14 |
| **brain** | 0.06 ± 0.01 | 0.07 ± 0.02 |
| **tumor** | 8.6 ± 0.20 | 5.5 ± 0.56 |

| organ | %ID/mL |
|---|---|
| tumor | 5.3 ± 0.45 |
| salivary glands | 0.96 ± 0.15 |
| muscle | 0.26 ± 0.02 |
| kidney | 23.5 ± 5.4 |
| heart | 0.82 ± 0.12 |
| liver | 0.54 ± 0.05 |

| organ | %ID/mL |
|---|---|
| tumor | 11.2 ± 3.3 |
| salivary glands | 2.0 ± 0.37 |
| muscle | 0.59 ± 0.06 |
| kidney | 46.2 ± 7.7 |
| heart | 1.7 ± 0.33 |
| liver | 1.5 ± 0.24 |

| | $^{68}$Ga-$^{nat}$F -8 | $^{18}$F-8 |
|---|---|---|
| **blood** | 1.7 ± 0.09 | 1.7 ± 0.48 |
| **heart** | 0.93 ± 0.08 | 0.92 ± 0.27 |
| **lung** | 1.3 ± 0.23 | 1.8 ± 0.70 |
| **liver** | 0.79 ± 0.17 | 0.93 ± 0.17 |
| **spleen** | 6.3 ± 1.5 | 9.6 ± 4.0 |
| **pancreas** | 0.48 ± 0.11 | 0.55 ± 0.14 |
| **stomach** | 0.42 ± 0.11 | 1.4 ± 1.1 |
| **intestine** | 0.35 ± 0.01 | 0.42 ± 0.10 |
| **kidneys** | 82.3 ± 5.9 | 118 ± 31.2 |
| **adrenals** | 2.2 ± 0.82 | 7.3 ± 2.8 |
| **muscle** | 0.24 ± 0.02 | 0.30 ± 0.06 |
| **bone** | 0.32 ± 0.07 | 1.3 ± 0.31 |
| **brain** | 0.06 ± 0.003 | 0.07 ± 0.01 |
| **tumor** | 6.5 ± 0.84 | 4.6 ± 2.2 |

| organ | %ID/mL |
|---|---|
| tumor | 4.1 ± 0.34 |
| salivary glands | 1.1 ± 0.11 |
| muscle | 0.27 ± 0.09 |
| kidney | 43.6 ± 2.6 |
| heart | 0.65 ± 0.25 |
| liver | 0.49 ± 0.07 |

| organ | %ID/mL |
|---|---|
| tumor | 6.9 ± 0.34 |
| salivary glands | 1.5 ± 0.20 |
| muscle | 0.56 ± 0.12 |
| kidney | 40.3 ± 7.4 |
| heart | 1.1 ± 0.41 |
| liver | 1.0 ± 0.40 |

| | $^{68}$Ga-$^{nat}$F -9 | $^{18}$F-9 |
|---|---|---|
| **blood** | 0.46 ± 0.11 | 1.1 ± 0.67 |
| **heart** | 0.48 ± 0.17 | 0.81 ± 0.40 |
| **lung** | 0.94 ± 0.20 | 0.98 ± 0.12 |
| **liver** | 0.42 ± 0.07 | 0.74 ± 0.45 |
| **spleen** | 25.43 ± 5.2 | 14.5 ± 3.3 |
| **pancreas** | 0.39 ± 0.09 | 0.48 ± 0.26 |
| **stomach** | 0.48 ± 0.40 | 0.46 ± 0.23 |
| **intestine** | 0.44 ± 0.34 | 0.41 ± 0.21 |
| **kidneys** | 54.9 ± 3.0 | 74.3 ± 6.1 |
| **adrenals** | 2.7 ± 0.19 | 1.9 ± 1.6 |
| **muscle** | 0.19 ± 0.06 | 0.32 ± 0.18 |
| **bone** | 0.18 ± 0.05 | 0.60 ± 0.17 |
| **brain** | 0.04 ± 0.01 | 0.06 ± 0.04 |
| **tumor** | 7.2 ± 0.63 | 9.1 ± 1.9 |

$^{18}F$-$^{nat}Ga$-7

| organ | %ID/mL |
|---|---|
| tumor | 7.2 ± 0.22 |
| salivary glands | 1.2 ± 0.09 |
| muscle | 0.58 ± 0.09 |
| kidney | 48.3 ± 11.9 |
| heart | 0.80 ± 0.12 |
| liver | 0.74 ± 0.04 |

| | $^{68}Ga-^{nat}F$ -7 | $^{18}F-^{nat}Ga-7$ |
|---|---|---|
| **blood** | 1.9 ± 0.14 | 1.1 ± 0.03 |
| **heart** | 1.2 ± 0.27 | 0.7 ± 0.07 |
| **lung** | 1.7 ± 0.16 | 1.4 ± 0.17 |
| **liver** | 0.77 ± 0.10 | 0.67 ± 0.07 |
| **spleen** | 13.8 ± 5.0 | 11.1 ± 2.3 |
| **pancreas** | 0.71 ± 0.11 | 0.60 ± 0.10 |
| **stomach** | 0.51 ± 0.07 | 0.49 ± 0.07 |
| **intestine** | 0.43 ± 0.07 | 0.60 ± 0.27 |
| **kidneys** | 34.1 ± 6.6 | 71.3 ± 13.3 |
| **adrenals** | 6.7 ± 2.2 | 3.0 ± 0.45 |
| **muscle** | 0.42 ± 0.22 | 0.36 ± 0.06 |
| **bone** | 0.52 ± 0.11 | 0.91 ± 0.11 |
| **brain** | 0.06 ± 0.01 | 0.11 ± 0.08 |
| **tumor** | 8.6 ± 0.20 | 10.4 ± 0.67 |

| | SUVmax | | | SUVmean | | |
|---|---|---|---|---|---|---|
| | mean | min | max | mean | min | max |
| background | 1,0 | 0,6 | 1 9 | 0,6 | 0,4 | 1,2 |
| bloodpool | 2,4 | 1,6 | 3 9 | 2,0 | 1,1 | 17,0 |
| parotid gland | 23.5 | 8,2 | 42,3 | 16,8 | 5,5 | 32,7 |
| submandibular gland | 26,7 | 10,1 | 43,8 | 19,6 | 7,0 | 29,7 |
| lungs | 1,0 | 0,5 | 3,1 | 0,7 | 0,3 | 2,0 |
| liver | 9,5 | 4,5 | 25,2 | 7,0 | 3,2 | 17,7 |
| spleen | 11,8 | 4,7 | 21 | 9,1 | 3,4 | 17,1 |
| pancreas | 3,9 | 1,8 | 9,2 | 2,7 | 1,3 | 7,4 |
| duodenum | 14,2 | 2,8 | 32,7 | 10,5 | 1,9 | 23,9 |
| bone | 1,7 | 0,8 | 3,1 | 1,1 | 0,6 | 2,1 |
| kidney | 44,3 | 19,1 | 75,2 | 32,1 | 13,2 | 54,7 |
| bladder | 8,3 | 0,5 | 112,0 | 6,1 | 0,3 | 85,7 |
| tumor lesions | 26,6 | 4,0 | 95,4 | 19,2 | 2,7 | 71,7 |

| | ratio SUVmax to background | | | ratio SUVmean to background | | |
|---|---|---|---|---|---|---|
| | mean | min | max | mean | min | max |
| bloodpool | 2,5 | 1,3 | 4,8 | 3,1 | 1,5 | 21,3 |
| parotid gland | 24,3 | 8,2 | 45,3 | 27,5 | 9,2 | 54,5 |
| submandibular gland | 27,8 | 10,1 | 54,7 | 32,5 | 11,7 | 61,8 |
| lungs | 1,1 | 0,4 | 3,3 | 1,1 | 0,4 | 4,0 |
| liver | 10,1 | 2,9 | 42,0 | 11,7 | 3,7 | 44,3 |
| spleen | 12,3 | 4,7 | 35,0 | 14,9 | 5,7 | 39,5 |
| pancreas | 4,0 | 1,5 | 11,3 | 4,3 | 1,9 | 10,8 |
| duodenum | 14,8 | 2,8 | 31,3 | 17,3 | 3,2 | 35,3 |
| bone | 1,7 | 0,9 | 2,9 | 1,8 | 1,0 | 3,2 |
| kidney | 46,7 | 16,9 | 98 7 | 53,8 | 19,8 | 109,3 |
| bladder | 8,3 | 0,6 | 112,0 | 9,8 | 0,5 | 142,8 |
| tumor lesions | 28,6 | 5,0 | 83,4 | 31,9 | 5,4 | 83,2 |

| local tumor | | SUVmax | ratio SUVmax | SUVmean | ratio SUVmean |
|---|---|---|---|---|---|
| | mean | 26,9 | 29,6 | 19,3 | 32,4 |
| | min | 4 | 5 | 2,7 | 5,4 |
| | max | 75,1 | 83,4 | 19,3 | 83,2 |

| lymph node metastases | | SUVmax | ratio SUVmax | SUVmean | ratio SUVmean |
|---|---|---|---|---|---|
| | mean | 22,2 | 23,7 | 16,5 | 27,3 |
| | min | 8,1 | 5,8 | 6,4 | 7,1 |
| | max | 67,5 | 63,6 | 44,6 | 70,7 |

| bone metastses | | SUVmax | ratio SUVmax | SUVmean | ratio SUVmean |
|---|---|---|---|---|---|
| | mean | 31,2 | 32,8 | 22,2 | 36,6 |
| | min | 7,9 | 7,9 | 5,3 | 6,8 |
| | max | 95,4 | 73,4 | 71,7 | 80 |

| visceral metastases | | SUVmax | ratio SUVmax | SUVmean | ratio SUVmean |
|---|---|---|---|---|---|
| | mean | 26,1 | 28,9 | 17,4 | 30,2 |
| | min | 20,4 | 18,5 | 15,5 | 22,1 |
| | max | 32,5 | 40,6 | 19,1 | 38,2 |

| | SUVmax | | | SUVmean | | |
|---|---|---|---|---|---|---|
| | mean | min | max | mean | min | max |
| with furosemide | 4,8 | 1,6 | 32 | 3,4 | 1,1 | 26,6 |
| without furosemide | 13,9 | 0,5 | 112 | 10,5 | 0,3 | 85,7 |

ROI-

| | %ID/mL |
|---|---|
| tumor | 10.9 ± 3.2 |
| salivary glands | 1.7 ± 0.1 |
| muscle | 0.41 ± 0.09 |
| kidney | 53 ± 5.9 |
| heart | 1.2 ± 0.12 |
| liver | 0.96 ± 0.03 |

| | $^{177}$Lu-rh-7 | $^{177}$Lu-rh-8 | $^{177}$Lu-rh-10 |
|---|---|---|---|
| **blood** | 0.006 ± 0.001 | 0.002 ± 0.0004 | 0.004 ± 0.001 |
| **heart** | 0.03 ± 0.01 | 0.02 ± 0.007 | 0.03 ± 0.007 |
| **lung** | 0.07 ± 0.01 | 0.04 ± 0.01 | 0.05 ± 0.007 |
| **liver** | 0.23 ± 0.03 | 0.31 ± 0.14 | 0.28 ± 0.13 |
| **spleen** | 0.27 ± 0.09 | 0.20 ± 0.04 | 0.22 ± 0.11 |
| **pancreas** | 0.02 ± 0.007 | 0.02 ± 0.005 | 0.02 ± 0.001 |
| **stomach** | 0.15 ± 0.05 | 0.11 ± 0.04 | 0.04 ± 0.008 |
| **intestine** | 1.1 ± 0.82 | 0.18 ± 0.09 | 0.11 ± 0.06 |
| **kidneys** | 10.1 ± 2.9 | 3.0 ± 0.62 | 4.1 ± 2.3 |
| **adrenals** | 0.13 ± 0.04 | 0.09 ± 0.03 | 0.09 ± 0.06 |
| **muscle** | 0.01 ± 0.006 | 0.01 ± 0.003 | 0.01 ± 0.003 |
| **bone** | 0.03 ± 0.01 | 0.03 ± 0.007 | 0.02 ± 0.01 |
| **brain** | 0.03 ± 0.02 | 0.009 ± 0,002 | 0.01 ± 0.003 |
| **LNCaP** | 11.7 ± 2.0 | 6.08 ± 1.01 | 10.2± 2.8 |

| | 1 h | 24 h |
|---|---|---|
| **blood** | 0.48 ± 0.15 | 0.004 ± 0.001 |
| **heart** | 0.42 ± 0.15 | 0.03 ± 0.007 |
| **lung** | 0.80 ± 0.16 | 0.05 ± 0.007 |
| **liver** | 0.40 ± 0.13 | 0.28 ± 0.13 |
| **spleen** | 10.7 ± 2.9 | 0.22 ± 0.11 |
| **pancreas** | 0.31 ± 0.12 | 0.02 ± 0.001 |
| **stomach** | 0.26 ± 0.08 | 0.04 ± 0.008 |
| **intestine** | 0.28 ± 0.10 | 0.11 ± 0.06 |
| **kidneys** | 173 ± 55.5 | 4.1 ± 2.3 |
| **adrenals** | 1.3 ± 0.37 | 0.09 ± 0.06 |
| **muscle** | 0.36 ± 0.10 | 0.01 ± 0.003 |
| **bone** | 0.37 ± 0.24 | 0.02 ± 0.01 |
| **brain** | 0.05 ± 0.01 | 0.01 ± 0.003 |
| **LNCaP** | 12.2 ± 1.8 | 10.2 ± 2.8 |

DUAL MODE RADIOTRACER AND-THERAPEUTICS

RELATED APPLICATIONS

This application is a continuation of U.S. patent application Ser. No. 17/849,297, filed on Jun. 24, 2022, which is a continuation of U.S. patent application Ser. No. 16/634,759, filed on Jan. 28, 2020, which is a 371 of international Patent Application No.: PCT/EP2018/070533, filed Jul. 30, 2018, which claims priority to EP Application No.: 17183795.8 filed Jul. 28, 2017.

The present invention relates to a ligand-SIFA-chelator conjugate, comprising, within in a single molecule: (a) one or more ligands which are capable of binding to a disease-relevant target molecule, (b) a silicon-fluoride acceptor (SIFA) moiety which comprises a covalent bond between a silicon and a fluorine atom and which can be labeled with $^{18}F$ by isotopic exchange of $^{19}F$ by $^{18}F$ or which is labeled with $^{18}F$, and (c) one or more chelating groups, optionally containing a chelated nonradioactive or radioactive cation.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Prostate Cancer

Prostate Cancer (PCa) remained over the last decades the most common malignant disease in men with high incidence for poor survival rates. Due to its overexpression in prostate cancer (Silver et al., Clinical Cancer Research 3, 81-85 (1997)), prostate-specific membrane antigen (PSMA) or glutamate carboxypeptidase II (GCP II) proved its eligibility as excellent target for the development of highly sensitive radiolabelled agents for endoradiotherapy and imaging of PCa (Afshar-Oromieh et al., European journal of nuclear medicine and molecular imaging 42, 197-209 (2015); Benešová et al., Journal of Nuclear Medicine 56, 914-920 (2015); Robu et al., Journal of Nuclear Medicine, jnumed. 116.178939 (2016); Weineisen et al.; Journal of Nuclear Medicine 55, 1083-1083 (2014); Rowe et al., Prostate cancer and prostatic diseases (2016); Maurer et al., Nature Reviews Urology (2016)). Prostate-specific membrane antigen is an extracellular hydrolase whose catalytic center comprises two zinc (II) ions with a bridging hydroxido ligand. It is highly upregulated in metastatic and hormone-refractory prostate carcinomas, but its physiologic expression has also been reported in kidneys, salivary glands, small intestine, brain and, to a low extent, also in healthy prostate tissue. In the intestine, PSMA facilitates absorption of folate by conversion of pteroylpoly-γ-glutamate to pteroylglutamate (folate). In the brain, it hydrolyses N-acetyl-Laspartyl-L-glutamate (NAAG) to N-acetyl-L-aspartate and glutamate.

Prostate-Specific Membrane Antigen (PSMA)

Prostate-specific membrane antigen (PSMA) is a type II transmembrane glycoprotein that is highly overexpressed on prostate cancer epithelial cells. Despite its name, PSMA is also expressed, to varying degrees, in the neovasculature of a wide variety of nonprostate cancers. Among the most common nonprostate cancers to demonstrate PSMA expression include breast, lung, colorectal, and renal cell carcinoma.

The general necessary structures of PSMA targeting molecules comprise a binding unit that encompasses a zinc-binding group (such as urea (Zhou et al., Nature Reviews Drug Discovery 4, 1015-1026 (2005)), phosphinate or phosphoramidate) connected to a P1' glutamate moiety, which warrants high affinity and specificity to PSMA and is typically further connected to an effector functionality (Machulkin et al., Journal of drug targeting, 1-15 (2016)). The effector part is more flexible and to some extent tolerant towards structural modifications. The entrance tunnel accommodates two other prominent structural features, which are important for ligand binding. The first one is an arginine patch, a positively charged area at the wall of the entrance funnel and the mechanistic explanation for the preference of negatively charged functionalities at the P1 position of PSMA. This appears to be the reason for the preferable incorporation of negative charged residues within the ligand-scaffold. An in-depth analysis about the effect of positive charges on PSMA ligands has been, to our knowledge, so far not conducted. Upon binding, the concerted repositioning of the arginine side chains can lead to the opening of an S1 hydrophobic accessory pocket, the second important structure that has been shown to accommodate an iodo-benzyl group of several urea based inhibitors, thus contributing to their high affinity for PSMA (Barinka et al., Journal of medicinal chemistry 51, 7737-7743 (2008)).

Zhang et al. discovered a remote binding site of PSMA, which can be employed for bidentate binding mode (Zhang et al., Journal of the American Chemical Society 132, 12711-12716 (2010)). The so called arene-binding site is a simple structural motif shaped by the side chains of Arg463, Arg511 and Trp541, and is part of the GCPII entrance lid. The engagement of the arene binding site by a distal inhibitor moiety can result in a substantial increase in the inhibitor affinity for PSMA due to avidity effects. PSMA I&T was developed with the intention to interact this way with PSMA, albeit no crystal structure analysis of binding mode is available. A necessary feature according to Zhang et al. is a linker unit (Suberic acid in the case of PSMA I&T) which facilitates an open conformation of the entrance lid of GCPII and thereby enabling the accessibility of the arene-binding site. It was further shown that the structural composition of the linker has a significant impact on the tumor-targeting and biologic activity as well as on imaging contrast and pharmacokinetics (Liu et al., Bioorganic & medicinal chemistry letters 21, 7013-7016 (2011)), properties which are crucial for both high imaging quality and efficient targeted endoradiotherapy.

Two categories of PSMA targeting inhibitors are currently used in clinical settings. On the one side there are tracers with chelating units for radionuclide complexation such as PSMA I&T or related compounds (Kiess et al., The quarterly journal of nuclear medicine and molecular imaging 59, 241 (2015)). On the other side there are small molecules, comprising a targeting unit and effector molecules.

The most often used agents for selective PSMA imaging are PSMA HBED-CC (Eder et al., Bioconjugate chemistry 23, 688-697 (2012)), PSMA-617 (Benešová et al., Journal of Nuclear Medicine 56, 914-920 (2015)) and PSMA I&T (Weineisen et al.; Journal of Nuclear Medicine 55, 1083-1083 (2014)), which are predominantly labelled with $^{68}Ga$ (88.9% $\beta^+$, $E_{\beta+,max}$=1.89 MeV, $t_{1/2}$=68 min). Among these $^{68}Ga$-PSMA-HBED-CC (also known as $^{68}Ga$-PSMA-11), is so far considered as the golden standard for PET imaging of PCa.

$^{18}F$ Labelling

Recently, several groups have focused on the development of novel $^{18}F$-labelled urea-based inhibitors for PCa diagnosis. In contrast to the radiometal $^{68}Ga$, which can be obtained from commercially distributed $^{68}Ge/^{68}Ga$ radionuclide generators ($^{68}Ge$; $t_{1/2}$=270.8 d), the radioisotope $^{18}F$-fluoride (96.7% $\beta^+$, $E_{\beta+,max}$=634 keV) requires an on-site cyclotron for its production. Despite this limitation, $^{18}F$ offers due to its longer half-live ($t_{1/2}$=109.8 min) and its lower positron energy, significant advantages in terms of routine-handling and image quality. Additionally, there is the possibility for largescale production in a cyclotron, which would be beneficial for a higher patient throughput and reduction of production costs. The $^{18}F$-labelled urea-based PSMA inhibitor $^{18}F$-DCFPyl demonstrated promising results in the detection of primary and metastatic PCa (Rowe et al., Molecular Imaging and Biology, 1-9 (2016)) and superiority to $^{68}Ga$-PSMA-HBED-CC in a comparative study (Dietlein et al., Molecular Imaging and Biology 17, 575-584 (2015)). Based on the structure of PSMA-617, the $^{18}F$-labelled analogue PSMA-1007 was recently developed, which showed comparable tumor-to-organ ratios (Cardinale et al., Journal of nuclear medicine: official publication, Society of Nuclear Medicine 58, 425-431 (2017); Giesel et al., European journal of nuclear medicine and molecular imaging 43, 1929-1930 (2016)). A comparative study with $^{68}Ga$-PSMA-HBED-CC revealed similar diagnostic accuracy of both tracers and a reduced urinary clearance of $^{18}F$-PSMA-1007, enabling a better assessment of the prostate (Giesel et al., European journal of nuclear medicine and molecular imaging 44, 678-688 (2017)).

An attractive approach for introducing $^{18}F$ labels is the use of silicon fluoride acceptors (SIFA). Silicon fluoride acceptors are described, for example, in Lindner et al., Bioconjugate Chemistry 25, 738-749 (2014). In order to preserve the silicon-fluoride bond, the use of silicon fluoride acceptors introduces the necessity of sterically demanding groups around the silicone atom. This in turn renders silicon fluoride acceptors highly hydrophobic. In terms of binding to the target molecule, in particular to the target molecule which is PSMA, the hydrophobic moiety provided by the silicone fluoride acceptor may be exploited for the purpose of establishing interactions of the radio-diagnostic or -therapeutic compound with the hydrophobic pocket described in Zhang et al., Journal of the American Chemical Society 132, 12711-12716 (2010). Yet, prior to binding, the higher degree of lipophilicity introduced into the molecule poses a severe problem with respect to the development of radiopharmaceuticals with suitable in vivo biodistribution, i.e. low unspecific binding in non-target tissue.

Failure to Solve the Hydrophobicity Problem

Despite many attempts, the hydrophobicity problem caused by silicon fluoride acceptors has not been satisfactorily solved in the prior art.

To explain further, Schirrmacher E. et al. (Bioconjugate Chem. 2007, 18, 2085-2089) synthesized different $^{18}F$-labelled peptides using the highly effective labelling synthon p-(di-tert-butylfluorosilyl) benzaldehyde ([$^{18}F$]SIFA-A), which is one example of a silicon fluoride acceptor. The SIFA technique resulted in an unexpectedly efficient isotopic $^{19}F$-$^{18}F$ exchange and yielded the $^{18}F$-synthon in almost quantitative yields in high specific activities between 225 and 680 GBq/μmol (6081-18 378 Ci/mmol) without applying HPLC purification. [$^{18}F$]SIFA-benzaldehyde was finally used to label the N-terminal amino-oxy (N-AO) derivatized peptides AO-Tyr3-octreotate (AO-TATE), cyclo(fK(AO-N) RGD) and N-AO-$PEG_2$-[D-Tyr-Gln-Trp-Ala-Val-Ala-His-Thi-Nle-$NH_2$] (AO-BZH3, a bombesin derivative) in high radiochemical yields. Nevertheless, the labelled peptides are highly lipophilic (as can be taken from the HPLC retention times using the conditions described in this paper) and thus are unsuitable for further evaluation in animal models or humans.

In Wängler C. et al. (Bioconjugate Chem., 2009, 20 (2), pp 317-321), the first SIFA-based Kit-like radio-fluorination of a protein (rat serum albumin, RSA) has been described. As a labelling agent, 4-(di-tert-butyl[$^{18}F$]fluorosilyl)benzenethiol (Si[$^{18}F$]FA-SH) was produced by simple isotopic exchange in 40-60% radiochemical yield (RCY) and coupled the product directly to maleimide derivatized serum albumin in an overall RCY of 12% within 20-30 min. The technically simple labelling procedure does not require any elaborated purification procedures and is a straightforward example of a successful application of Si-18F chemistry for in vivo imaging with PET. The time-activity cureves and μPET images of mice showed that most of the activity was localized in the liver, thus demonstrating that the labelling agent is too lipophilic and directs the in vivo probe to hepatobiliary excretion and extensive hepatic metabolism.

Wängler C. et al. (see Bioconjug Chem. 2010 Dec. 15; 21(12):2289-96) subsequently tried to overcome the major drawback of the SIFA technology, the high lipophilicity of the resulting radiopharmaceuticals, by synthesizing and evaluating new SIFA-octreotate analogues (SIFA-Tyr3-octreotate, SIFA-Asn (AcNH-β-Glc)-Tyr3-octreotate and SIFA-Asn (AcNH-β-Glc)-PEG-Tyr3-octreotate). In these compounds, hydrophilic linkers and pharmacokinetic modifiers were introduced between the peptide and the SIFA-moiety, i.e. a carbohydrate and a PEG linker plus a carbohydrate. As a measure of lipophilicity of the conjugates, the log P(ow) was determined and found to be 0.96 for SIFA-Asn(AcNH-β-Glc)-PEG-$Tyr^3$-octreotate and 1.23 for SIFA-Asn(AcNH-β-Glc)-$Tyr^3$-octreotate. These results show that the high lipophilicity of the SIFA moiety can only be marginally compensated by applying hydrophilic moieties. A first imaging study demonstrated excessive hepatic clearance/liver uptake and thus has never been transferred into a first human study.

Bernard-Gauthier et al. (Biomed Res Int. 2014; 2014: 454503) reviews a great plethora of different SIFA species that have been reported in the literature ranging from small prosthetic groups and other compounds of low molecular weight to labelled peptides and most recently affibody molecules. Based on these data the problem of lipophilicity of SIFA-based prosthetric groups has not been solved sofar; i.e. a methodology that reduces the overall lipophilicity of a SIFA conjugated peptide to a log D lower than approx −2,0 has not been described.

In Lindner S. et al. (Bioconjug Chem. 2014 Apr. 16; 25(4):738-49) it is described that PEGylated bombesin (PESIN) derivatives as specific GRP receptor ligands and RGD (one-letter codes for arginine-glycine-aspartic acid) peptides as specific αvβ3 binders were synthesized and tagged with a silicon-fluorine-acceptor (SIFA) moiety. To compensate the high lipophilicity of the SIFA moiety various hydrophilic structure modifications were introduced leading to reduced log D values. SIFA-Asn(AcNH-β-Glc)-PESIN, SIFA-Ser(β-Lac)-PESIN, SIFA-Cya-PESIN, SIFA-LysMe3-PESIN, SIFA-γ-carboxy-d-Glu-PESIN, SIFA-Cya2-PESIN, SIFA-LysMe3-γ-carboxy-d-Glu-PESIN, SIFA-(γ-carboxy-d-Glu)2-PESIN, SIFA-RGD, SIFA-γ-carboxy-d-Glu-RGD, SIFA-(γ-carboxy-d-Glu)2-RGD, SIFA-LysMe3-γ-carboxy-d-Glu-RGD. All of these peptides—already improved and derivatized with the aim to reduce the lipophilicity—showed a log D value in the range between +2 and −1.22.

In Niedermoser S. et al. (J Nucl Med. 2015 July; 56(7): 1100-5), newly developed $^{18}$F-SIFA- and $^{18}$F-SIFAlin-(SIFA=silicon-fluoride acceptor) modified TATE derivatives were compared with the current clinical gold standard $^{68}$Ga-DOTATATE for high-quality imaging of somatostatin receptor-bearing tumors. For this purpose, $^{18}$F-SIFA-TATE and two quite complex analogues, $^{18}$F-SIFA-Glc-PEG1-TATE, $^{18}$F-SIFAlin-Glc-Asp2-PEG1-TATE were developed. None of the agents showed a log D<−1.5.

In view of the above, the technical problem underlying the present invention can be seen in providing radio-diagnostics and radio-therapeutics which contain a silicone fluoride acceptor and which are, at the same time, characterized by favourable in-vivo properties.

As will be become apparent in the following, the present invention established a proof-of-principle using specific conjugates which bind with high affinity to prostate-specific antigen (PSMA) as target. Accordingly, a further technical problem underlying the present invention can be seen in providing improved radio-therapeutics and -diagnostics for the medical indication which is cancer, preferably prostate cancer.

These technical problems are solved by the subject-matter of the claims. Accordingly, in the first aspect, the present invention relates to a ligand-SIFA-chelator conjugate, comprising, within in a single molecule: (a) one or more ligands which are capable of binding to a disease-relevant target molecule, (b) a silicon-fluoride acceptor (SIFA) moiety which comprises a covalent bond between a silicon and a fluorine atom and which can be labeled with $^{18}$F by isotopic exchange of $^{19}$F by $^{18}$F or which is labeled with $^{18}$F, and (c) one or more chelating groups, optionally containing a chelated nonradioactive or radioactive cation.

The ligand-SIFA-chelator conjugate comprises three separate moieties. The three separate moieties are a) one or more ligands which are capable of binding to a disease-relevant target molecule, (b) a silicon-fluoride acceptor (SIFA) moiety which comprises a covalent bond between a silicon and a fluorine atom, and (c) one or more chelating groups, optionally containing a chelated nonradioactive or radioactive cation.

The fluorine atom on the SIFA moiety can be $^{19}$F or $^{18}$F.

Whilst certain ligands which are capable of binding to a disease-relevant target molecule may be cyclic peptides, such cyclic peptides are not chelating groups as envisaged herein, as the problem of the hydrophobic SIFA moiety is not solved in the absence of a further chelating moiety. Thus compounds of the invention require a hydrophilic chelating group in addition to the ligands which are capable of binding to a disease-relevant target molecule. The hydrophilic chelating group is required to reduce the hydrophobic nature of the compounds caused by the presence of the SIFA moiety.

The ligand in relation to the first aspect of the invention is defined in functional terms. This is the case because the present invention does not depend on the specific nature of the ligand in structural terms. Rather, a key aspect of the invention is the combination, within a single molecule, of a silicon fluoride acceptor and a chelator or a chelate. These two structural elements, SIFA and the chelator, exhibit a spatial proximity. Preferably, the shortest distance between two atoms of the two elements is less or equal 25 Å, more preferably less than 20 Å and even more preferably less than 15 Å. Alternatively or in addition, it is preferred that not more than 25 covalent bonds separate an atom of the SIFA moiety and an atom the chelator, preferably not more than 20 chemical bonds and even more preferably not more than 15 chemical bonds.

The cation in accordance with item (c) of the first aspect is a radioactive or non-radioactive cation. It is preferably a radioactive or non-radioactive metal cation, and more preferably a radioactive metal cation. Examples are given further below.

As a consequence, conjugates fall under the terms of the first aspect which are radioactively labelled at both the SIFA moiety and the chelating group, molecules which are radioactive labelled at only one of the two sides, as well as molecules which are not radiolabelled at all. In the latter case, the chelating group may be either a complex of a cold (non-radioactive) ion or may devoid of any ion.

The present inventors surprisingly discovered that placement of the silicone fluoride acceptor in the neighbourhood of a hydrophilic chelator such as, but not limited to, DOTAGA or DOTA, shields or compensates efficiently the lipophilicity of the SIFA moiety to an extent which shifts the overall hydrophobicity of the radio-therapeutic or -diagnostic compound in a range which renders the compound suitable for in-vivo administration.

In addition, the combination of the use of a chelator and an isotopic exchange on SIFA by means of $^{18}$F-fluoride also results in "paired" diagnostic tracers that can either be used as [$^{18}$F][$^{nat}$Ion] tracers at centers with onsite cyclotron or centers that obtain $^{18}$F-fluoride by shipment from cyclotron centers, whereas in centers, that do not have access to $^{18}$F-fluoride but have access to radioisotope generators, such as a Ge-68/Ga-68 generator, the corresponding versions, e.g. [$^{nat}$F][$^{68}$Ga] tracers can be used.

Importantly, in both cases, the chemically identical radiopharmaceutical is injected, and thus no differences in the in vivo behavior are expected. Whereas currently, due to chemical differences, the clinical data of a $^{18}$F-labelled compound provided by a patient cohort at one site cannot be directly compared with the clinical data of a $^{68}$Ga-analogue provided by another group at another site, radiopharmaceuticals and/or diagnostics according to the invention can be directly compared and thus will allow to link such data (e.g. data from a center in Europe working with F-18 and another center in India working with Ga-68).

Furthermore, when suitably selected, the chelate can also be used for labelling with a therapeutic isotope, such as the beta-emitting isotopes Lu-177, Y-90, or the alpha emitting isotope Ac-225, thus allowing to expand the concept of "paired" tracers to bridge diagnostic ([$^{18}$F][$^{nat}$Lu] tracers) and therapeutic radiopharmaceuticals ([$^{nat}$F][$^{177}$Lu].

A further advantage of the compounds, especially of PSMA targeted compounds of the present invention is their surprisingly low accumulation in the kidneys of mice when compared to other PSMA targeted radiopharmaceuticals, such as PSMA I&T. Without wishing to be bound by a particular theory, it seems to be the combination of the structural element SIFA with a chelator which provides for the unexpected reduction of accumulation in the kidneys.

In terms of lipophilicity/hydrophilicity, the log P value (sometimes also referred to as log D value) is an art-established measure.

The term "lipophilicity" relates to the strength of being dissolved in, or be absorbed in lipid solutions, or being adsorbed at a lipid-like surface or matrix. It denotes a preference for lipids (literal meaning) or for organic or apolar liquids or for liquids, solutions or surfaces with a small dipole moment as compared to water. The term "hydrophobicity" is used with equivalent meaning herein. The adjectives lipophilic and hydrophobic are used with corresponding meaning to the substantives described above.

The mass flux of a molecule at the interface of two immiscible or substantially immiscible solvents is governed by its lipophilicity. The more lipophilic a molecule is, the more soluble it is in the lipophilic organic phase. The partition coefficient of a molecule that is observed between water and n-octanol has been adopted as the standard measure of lipophilicity. The partition coefficient P of a species A is defined as the ratio $P=[A]_{n\text{-}octanol}/[A]_{water}$. A figure commonly reported is the log P value, which is the logarithm of the partition coefficient. In case a molecule is ionizable, a plurality of distinct microspecies (ionized and not ionized forms of the molecule) will in principle be present in both phases. The quantity describing the overall lipophilicity of an ionizable species is the distribution coefficient D, defined as the ratio D=[sum of the concentrations of all microspecies]$_{n\text{-}octanol}$/[sum of the concentrations of all microspecies]$_{water}$. Analogous to log P, frequently the logarithm of the distribution coefficient, log D, is reported. Often, a buffer system, such as phosphate buffered saline is used as alternative to water in the above described determination of log P.

If the lipophilic character of a substituent on a first molecule is to be assessed and/or to be determined quantitatively, one may assess a second molecule corresponding to that substituent, wherein said second molecule is obtained, for example, by breaking the bond connecting said substituent to the remainder of the first molecule and connecting (the) free valence(s) obtained thereby to hydrogen(s).

Alternatively, the contribution of the substituent to the log P of a molecule may be determined. The contribution $\pi x_x$ of a substituent X to the log P of a molecule R—X is defined as $\pi x_x = \log P_{R\text{-}X} - \log P_{R\text{-}H}$, wherein R—H is the unsubstituted parent compound.

Values of P and D greater than one as well as log P, log D and $\pi x_x$ values greater than zero indicate lipophilic/hydrophobic character, whereas values of P and D smaller than one as well as log P, log D and $\pi x_x$ values smaller than zero indicate hydrophilic character of the respective molecules or substituents.

The above described parameters characterizing the lipophilicity of the lipophilic group or the entire molecule according to the invention can be determined by experimental means and/or predicted by computational methods known in the art (see for example Sangster, Octanol-water Partition Coefficients: fundamentals and physical chemistry, John Wiley & Sons, Chichester. (1997)).

In a preferred embodiment, the log P value of the compounds of the invention is between −5 and −1.5. It is particularly preferred that the log P value is between −3.5 and −2.0.

In a preferred embodiment, a ligand in accordance with the invention comprises or consists of a peptide, a peptidomimetic or a substituted urea, substituents including amino acids. It is understood that a ligand which comprises a peptide or peptidomimetic also comprises a non-peptidic and non-peptidomimetic part. In terms of molecular weight, preference is given to molecular weights below 15 kDa, below 10 kDa or below 5 kDa. Accordingly, small proteins are also embraced by the term "ligand". Target molecules are not particularly limited and include enzymes, receptors, epitopes, transporters, cell surface molecules and proteins of the extracellular matrix. Preferred are targets which are disease relevant. Particularly preferred are targets which are causally involved in a given disease, or which are highly overexpressed in a given disease and/or the inhibition of which can cause a beneficial effect in a patient suffering from a given disease. The ligands are preferably high affinity ligands with preferable affinity, expressed as $IC_{50}$, being below 50 nM, below 20 nM or below 5 nM.

Especially preferred are those ligands which bind with high affinity to disease-relevant target molecules or disease-relevant biomolecules including, but not limited to somatostatin receptors, bombesin receptors, chemokine receptors, integrin receptors, cholecystokinin receptors, melanocortin receptors, vasoactive intestinal peptide receptors, neurotensin receptors, neuropeptide Y receptors, neurokinin receptors, glucacon-like peptide 1 receptors, Her2-receptors, PD-L1, PD-1, gonadotropin releasing hormone receptors and prostate-specific membrane antigen (PSMA).

The term "disease-relevant" refers preferably to a causal involvement in a disease.

Preferably, the silicon-fluoride acceptor (SIFA) moiety has the structure represented by formula (I):

(I)

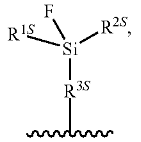

wherein $R^{1S}$ and $R^{2S}$ are independently a linear or branched C3 to C10 alkyl group, preferably $R^{1S}$ and $R^{2S}$ are selected from isopropyl and tert-butyl, and are more preferably $R^{1S}$ and $R^{2S}$ are tert-butyl; $R^{3S}$ is a C1 to C20 hydrocarbon group which may comprise one or more aromatic and one or more aliphatic units and/or up to 3 heteroatoms selected from O and S, preferably $R^{3S}$ is a C6 to C10 hydrocarbon group which comprises an aromatic ring and which may comprise one or more aliphatic units; more preferably $R^{3S}$ is a phenyl ring, and most preferably, $R^{3S}$ is a phenyl ring wherein the Si-containing substituent and the bond marked by ∿∿∿ are in a para-position, and wherein the SIFA moiety is attached to the remainder of the conjugate via the bond marked by ∿∿∿ .

More preferably, the silicon-fluoride acceptor (SIFA) moiety has the structure represented by formula (Ia):

(Ia)

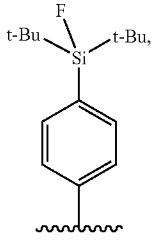

wherein t-Bu indicates a tert-butyl group.

A preferred chelating group comprises at least one of the following (i), (ii) or (iii).

(i) A macrocyclic ring structure with 8 to 20 ring atoms of which 2 or more, more preferably 3 or more, are selected from oxygen atoms or nitrogen atoms. Preferably, 6 or less ring atoms are selected from oxygen atoms or nitrogen atoms. Especially preferred is that 3 or 4 ring atoms are nitrogen atoms or oxygen atoms. Among the oxygen and nitrogen atoms, preference is given to the nitrogen atoms. In combination with the macrocyclic ring structure, the preferred chelating group may comprise 2 or more, such as 2 to 6, preferably 2 to 4, carboxyl groups and/or hydroxyl groups. Among the carboxyl groups and the hydroxyl groups, preference is given to the carboxyl groups.

(ii) An acyclic, open chain chelating structure with 8 to 20 main chain (back bone) atoms of which 2 or more, more preferably 3 or more are heteroatoms selected from oxygen atoms or nitrogen atoms. Preferably, 6 or less back bone atoms are selected from oxygen atoms or nitrogen atoms. Among the oxygen and nitrogen atoms, preference is given to the nitrogen atoms. More preferably, the open chain chelating structure is a structure which comprises a combination of 2 or more, more preferably 3 or more heteroatoms selected from oxygen atoms or nitrogen atoms, and 2 or more, such as 2 to 6, preferably 2 to 4, carboxyl groups and/or hydroxyl groups. Among the carboxyl groups and the hydroxyl groups, preference is given to the carboxyl groups.

(iii) A branched chelating structure containing a quarternary carbon atom. Preferably the quarternary carbon atom is substituted with 3 identical chelating groups in addition to the SIFA/ligand moiety. The substituted chelating groups can comprise an amide. The substituted chelating groups can comprise an aromatic group. The substituted chelating groups can comprise a hydroxypyridinone.

In preferred specific examples, the chelating group is a residue of a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecan (DO2A) 1,4,7,10-tetracyclododecan-N,N',N",N"-tetraacetic acid (DOTA), α-(2-carboxyethyl)-1,4,7,10-tetraazacyclododecane-1,4,7,10-tetraacetic acid (DOTAGA), 1,4,7,10 tetraazacyclododecane N, N', N", N"' 1,4,7,10-tetra(methylene) phosphonic acid (DOTMP), N,N'-dipyridoxylethylendiamine-N,N'-diacetate-5,5'-bis (phosphat) (DPDP), diethylene triamine N,N',N" penta (methylene) phosphonic acid (DTMP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), tetra 3-hydroxy-N-methyl-2-pyridinone chelators (4-((4-(3-(bis(2-(3-hydroxy-1-methyl-2-oxo-1,2-dihydropyridine-4-carboxamido)ethyl)amino)-2-((bis (2-(3-hydroxy-1-methyl-2-oxo-1,2-dihydropyridine-4-carboxamido)ethyl)amino)methyl)propyl)phenyl)amino)-4-oxobutanoic acid), abbreviated as Me-3,2-HOPO, 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), tris(hydroxypyridinone) (THP), terpyridin-bis (methyleneamintetraacetic acid (TMT), 1,4,7-triazacyclononane-1,4,7-tris[methylene(2-carboxyethyl)phosphinic acid] (TRAP), 1,4,7,10-tetraazacyclotridecan-N,N',N",N"'-tetraacetic acid (TRITA), 3-[[4,7-bis[[2-carboxyethyl(hydroxy)phosphoryl]methyl]-1,4,7-triazonan-1-yl]methyl-hydroxy-phosphoryl]propanoic acid, and triethylenetetraaminehexaacetic acid (TTHA), which residue is provided by covalently binding a carboxyl group contained in the chelating agent to the remainder of the conjugate via an ester or an amide bond.

Particular chelators are shown below:

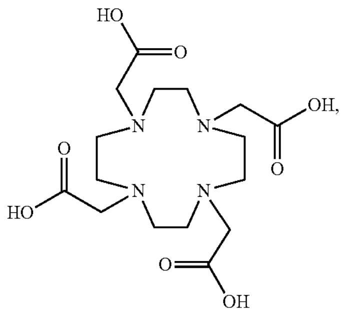

DOTA

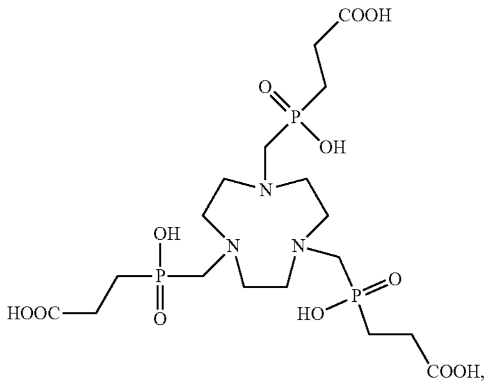

TRAP

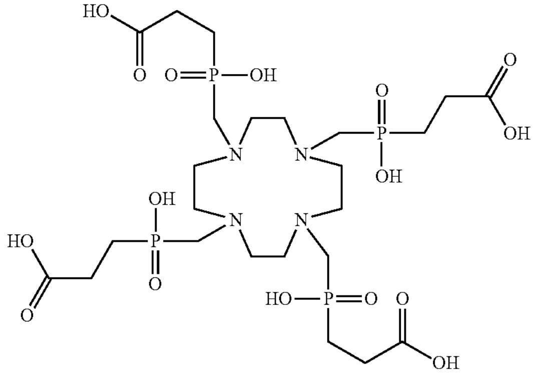

DOTPI

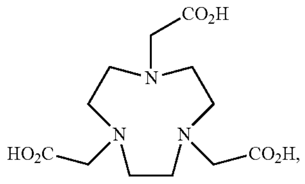

NOTA

-continued

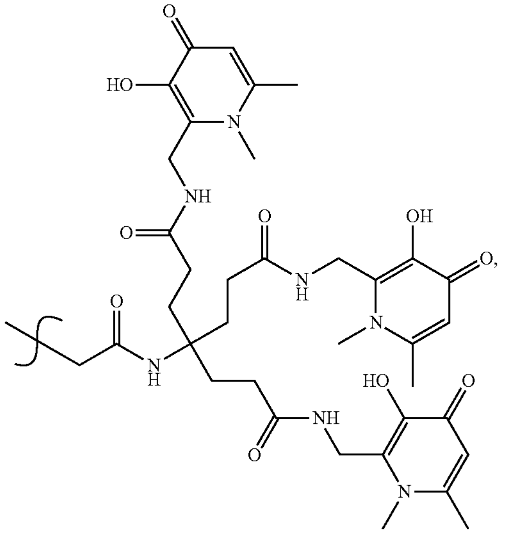

THP

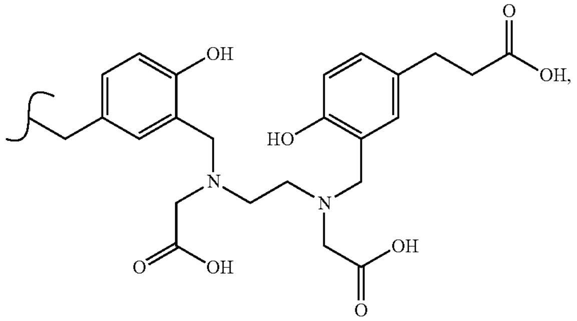

HBED

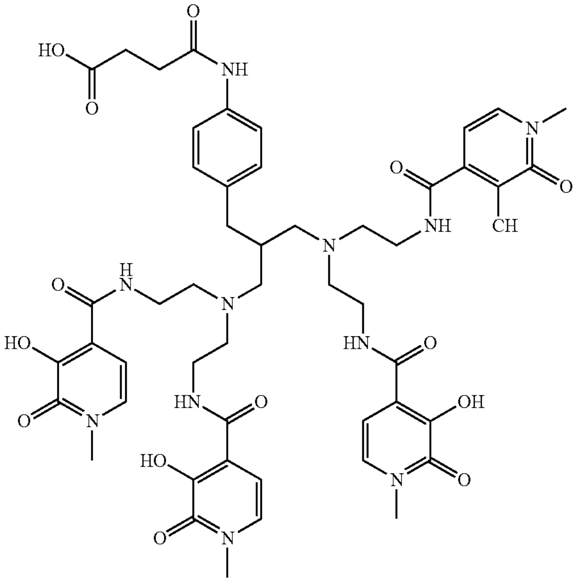

Me-3,2-HOPO

Among the above exemplary chelating agents, particular preference is given to a chelating agent selected from TRAP, DOTA and DOTAGA.

Metal- or cation-chelating macrocyclic and acyclic compounds are well-known in the art and available from a number of manufacturers. While the chelating moiety in accordance with the present invention is not particularly limited, it is understood that numerous moieties can be used in an off-the-shelf manner by a skilled person without further ado.

The chelating group may comprise a chelated cation which may be radioactive or non-radioactive, preferably a chelated metal cation which may be radioactive or non-radioactive. More preferred is a chelated radioactive metal isotope.

Preferred examples of cations that may be chelated by the chelating group are the cations of $^{43}$Sc, $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{67}$Ga $^{68}$Ga, $^{89}$Zr, $^{90}$Y, $^{89}$Y, <Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{152}$Tb, $^{155}$Tb, $^{161}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At., $^{212}$Bi, $^{213}$Bi, $^{223}$Ra, $^{225}$Ac, $^{227}$Th, a cationic molecule comprising $^{18}$F or a cation such as $^{18}$F-$[AlF]^{2+}$; more preferably the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.

Using PSMA binders as an example, the present inventors reduced the above disclosed invention to practice. This is the subject-matter of the preferred aspects and embodiments disclosed in the following. Yet, the surprising finding made by the present inventors—compensation of the lipophilicity of the SIFA moiety to a surprising extent—is not limited to molecules comprising a PSMA binder.

Accordingly, the ligand is preferably capable of binding to prostate-specific membrane antigen (PSMA).

More preferably, the ligand has the structure represented by formula (II):

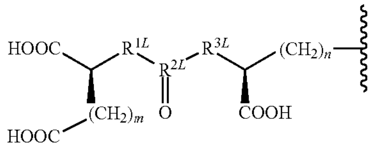

(II)

wherein m is an integer of 2 to 6, preferably 2 to 4, more preferably 2; n is an integer of 2 to 6, preferably 2 to 4, more preferably 2 or 3; $R^{1L}$ is $CH_2$, NH or O, preferably NH; $R^{3L}$ is $CH_2$, NH or O, preferably NH; $R^{2L}$ is C or P(OH), preferably C; and wherein the ligand is attached to the remainder of the conjugate via the bond marked by ∿∿∿.

The ligand can have the structure represented by formula (IIa):

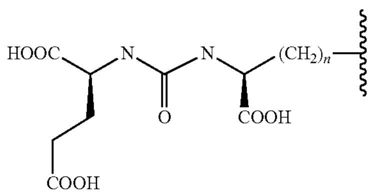

(IIa)

wherein n is an integer of 2 to 6; and wherein the ligand is attached to the remainder of the conjugate via the bond marked by ∿∿∿.

A number of PSMA binders are known in the art which are all suitable in accordance with the invention. The above preferred embodiment is a structural definition of a preferred group of PSMA binders.

It is particularly preferred that the conjugate of the first aspect is a compound of formula (III):

(III)

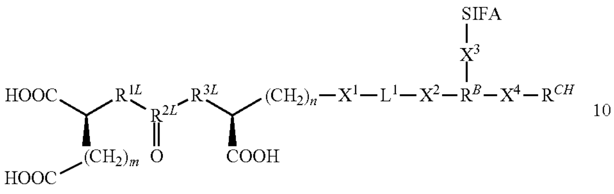

or a pharmaceutically acceptable salt thereof, wherein:

SIFA is a silicon-fluoride acceptor (SIFA) moiety which comprises a covalent bond between a silicon and a fluorine atom and which can be labeled with $^{18}F$ by isotopic exchange of $^{19}F$ by $^{18}F$ or which is labeled with $^{18}F$; preferably SIFA is the SIFA moiety of formula (I) and more preferably of formula (Ia) defined above;

m is an integer of 2 to 6, preferably 2 or 3, more preferably 2;

n is an integer of 2 to 6, preferably 2 or 3, more preferably 2 or 4;

$R^{1L}$ is $CH_2$, NH or O, preferably NH;

$R^{3L}$ is $CH_2$, NH or O, preferably NH;

$R^{2L}$ is C or P(OH), preferably C;

$X^1$ is selected from an amide bond, an ether bond, a thioether bond, an ester bond, a thioester bond, an urea bridge, and an amine bond, preferably an amide bond;

$X^2$ is selected from an amide bond, an ether bond, a thioether bond, an ester bond, a thioester bond, an urea bridge, and an amine bond, preferably an amide bond;

$L^1$ is a divalent linking group with a structure selected from an oligoamide, an oligoether, an oligothioether, an oligoester, an oligothioester, an oligourea, an oligo (ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo ether-urea), an oligo (thioether-ester), an oligo(thioether-thioester), an oligo (thioether-urea), an oligo(ester-thioester), an oligo(ester-urea), and an oligo(thioester-urea), preferably with a structure selected from an oligoamide and an oligo (ester-amide).

$L^1$ can be optionally substituted with one or more substitutents independently selected from —OH, —$OCH_3$, —COOH, —$COOCH_3$, —$NH_2$, and —NHC(NH)$NH_2$.

$X^3$ is selected from an amide bond, and ester bond, an ether, an amine, and a linking group of the formula:

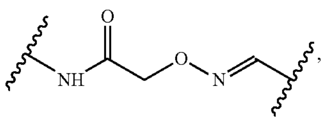 [SMILES: */C=N/OCC(=O)N*]

wherein the bond marked by ~~~ at the NH group is bound to $R^B$ and the other bond marked by ~~~ is bound to SIFA; preferably $X^3$ is an amide bond; $R^B$ is a trivalent coupling group; $X^4$ is selected from an amide bond, an ether bond, a thioether bond, and ester bond, a thioester bond, a urea bridge, an amine bond, a linking group of the formula:

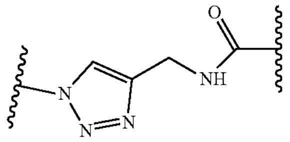 [SMILES: *C(=O)NCc1cn(*)nn1]

wherein the amide bond marked by ~~~ is formed with the chelating group, and the other bond marked by ~~~ is bound to $R^B$; and a linking group of the formula:

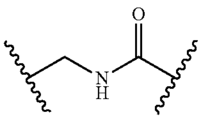 [SMILES: *CNC(*)=O]

wherein the bond marked by ~~~ at the carbonyl end is formed with the chelating group, and the other bond marked by ~~~ is bound to $R^B$; preferably $X^4$ is an amide bond;

$R^{CH}$ is chelating group optionally containing a chelated radioactive or nonradioactive cation, preferably a radioactive or nonradioactive metal cation, wherein preferred embodiments of said chelating group and of the optional chelated cation are as defined above.

The term "oligo" as used in oligoamide, oligoether, oligothioether, oligoester, oligothioester, oligourea, oligo (ether-amide), oligo(thioether-amide), oligo(ester-amide), oligo(thioester-amide), oligo(urea-amide), oligo(ether-thioether), oligo(ether-ester), oligo(ether-thioester), oligo(ether-urea), oligo(thioether-ester), oligo(thioether-thioester), oligo (thioether-urea), oligo(ester-thioester), oligo(ester-urea), and oligo(thioester-urea) is preferably to be understood as referring to a group wherein 2 to 20, more preferably wherein 2 to 10 subunits are linked by the type of bonds specified in the same terms. As will be understood by the skilled reader, where two different types of bonds are indicated in brackets, both types of bonds are contained in the concerned group (e.g. in "oligo (ester-amide)", ester bonds and amide bonds are contained).

It is preferred that $L^1$ comprises a total of 1 to 5, more preferably a total of 1 to 3, and most preferably a total of 1 or 2 amide and/or ester bonds, preferably amide bonds, within its backbone.

The term oligoamide therefore describes a moiety having a chain of $CH_2$ or CHR groups interspersed with groups selected from NHCO or CONH. Each occurrence of the R moiety is an optional substituent selected from —OH, —$OCH_3$, —COOH, —$COOCH_3$, —$NH_2$, and —NHC(NH)$NH_2$.

It is also preferred that —$X^1$-$L^1$-$X^2$— represents one of the following structures (L-1) and (L-2):

$$—NH—C(O)—R^6—C(O)—NH—R^7—NH—C(O)— \quad (L\text{-}1)$$

$$—C(O)—NH—R^8—NH—C(O)—R^9—C(O)—NH—R^{10}—NH—C(O)— \quad (L\text{-}2)$$

wherein $R^6$ to $R^{10}$ are independently selected from C2 to C10 alkylene, preferably linear C2 to C10 alkylene, which alkylene groups may each be substituted by one or more substitutents independently selected from —OH, —$OCH_3$, —COOH, —$COOCH_3$, —$NH_2$, and —NHC(NH)$NH_2$.

Especially preferred is that the total number of carbon atoms in $R^6$ and $R^7$ is 4 to 20, more preferably 4 to 16, without carbon atoms contained in optional substituents. Especially preferred is that the total number of carbon atoms in $R^8$ to $R^{10}$, is 6 to 20, more preferably 6 to 16, without carbon atoms contained in optional substituents.

It is particularly preferred that —$X^1$-$L^1$-$X^2$— represents one of the following structures (L-3) and (L-4):

—NH—C(O)—$R^{11}$—C(O)—NH—$R^{12}$—CH(COOH)—NH—C(O)— (L-3)

—C(O)—NH—CH(COOH)—$R^{13}$—NH—C(O)—$R^{14}$—C(O)—NH—$R^{15}$—CH(COOH)—NH—C(O)— (L-4)

wherein $R^{11}$ to $R^{15}$ are independently selected from C2 to C8 alkylene, preferably linear C2 to C8 alkylene.

Especially preferred is that the total number of carbon atoms in $R^{11}$ and $R^{12}$ or $R^{13}$ to $R^{15}$, respectively, is 8 to 18, more preferably 8 to 12, yet more preferably 9 or 10.

Preferably, $R^B$ has the structure represented by formula (IV):

(IV)

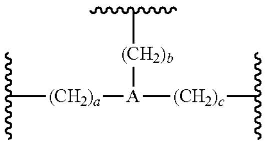

wherein: A is selected from N, $CR^{16}$, wherein $R^{16}$ is H or C1-C6 alkyl, and a 5 to 7 membered carbocyclic or heterocyclic group; preferably A is selected from N and CH, and more preferably A is CH; the bond marked by $(CH_2)_a$ is formed with $X^2$, and a is an integer of 0 to 4, preferably 0 or 1, and most preferably 0; the bond marked by $(CH_2)_b$ is formed with $X^3$, and b is an integer of 0 to 4, preferably of 0 to 2, and more preferably 0 or 1; and the bond marked by at $(CH_2)_c$ is formed with $X^4$, and c is an integer of 0 to 4, preferably of 0 to 2, and more preferably 0 or 1.

Even more preferred as a conjugate in accordance with the invention is a compound of formula (IIIa):

(IIIa)

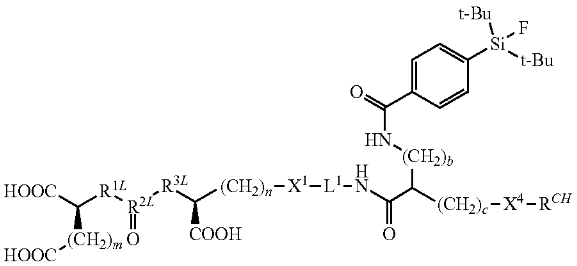

or a pharmaceutically acceptable salt thereof, wherein m, n, $R^{1L}$, $R^{2L}$, $R^{3L}$, $X^1$, $L^1$, b, c, $X^4$ and $R^{CH}$ are as defined above, including all preferred embodiments thereof.

It is preferred for the compound of formula (IIIa) that b+c≥1.

It is also preferred for the compound of formula (IIIa) that b+c≤3.

It is more preferred for the compound of formula (IIIa) that b is 1 and c is 0.

It is also preferred for the compound of formula (III) that —$X^4$—$R^{CH}$ represents a residue of a chelating agent selected from DOTA and DOTAGA bound with one of its carboxylic groups via an amide bond to the remainder of the conjugate.

In a preferred embodiment of the compound of formula (III), said compound is a compound of formula (IIIb):

(IIIb)

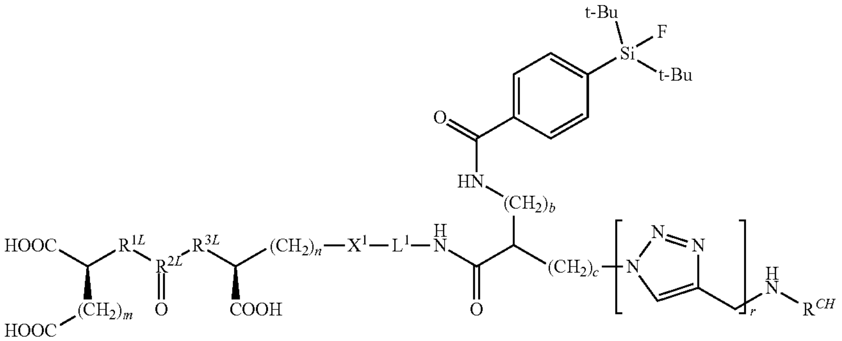

or a pharmaceutically acceptable salt thereof, wherein m, n, $R^{1L}$, $R^{2L}$, $R^{3L}$, $X^1$, $L^1$, b, c, $X^4$ and $R^{CH}$ are as defined above; and r is 0 or 1.

Especially preferred is that —N(H)—$R^{CH}$ represents a residue of a chelating agent selected from DOTA and DOTAGA bound with one of its carboxylic groups via an amide bond to the remainder of the conjugate.

Most preferred compounds of the invention are the following:
(5)
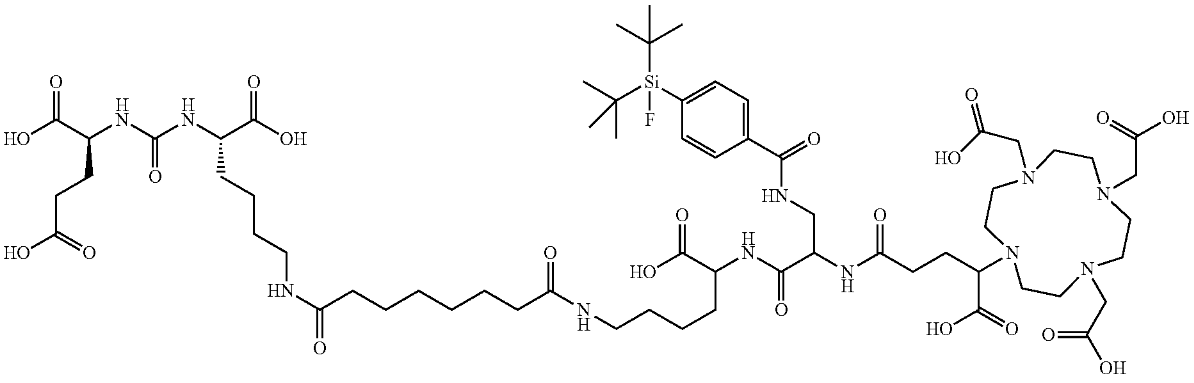
PSMA-SIFA
and isomers thereof:
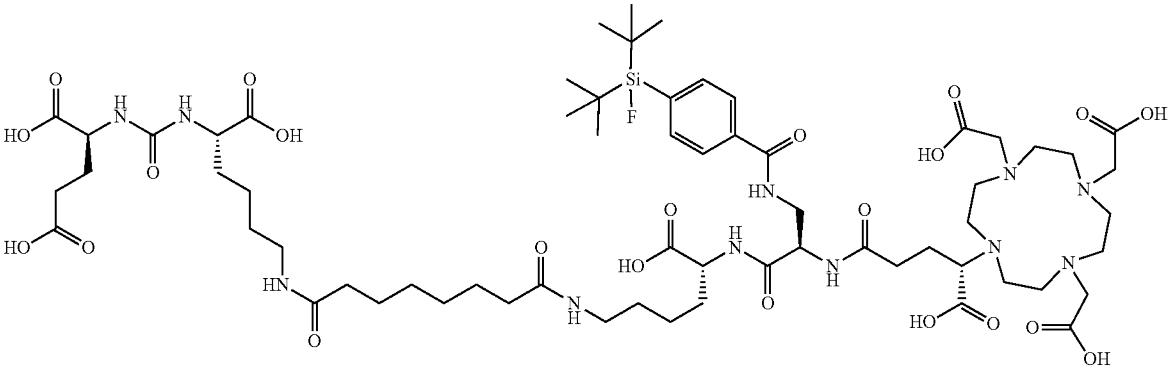
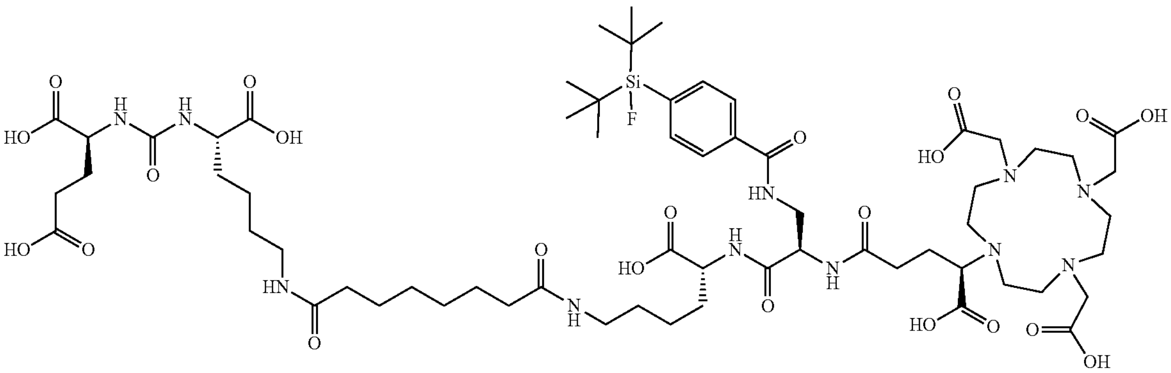

-continued
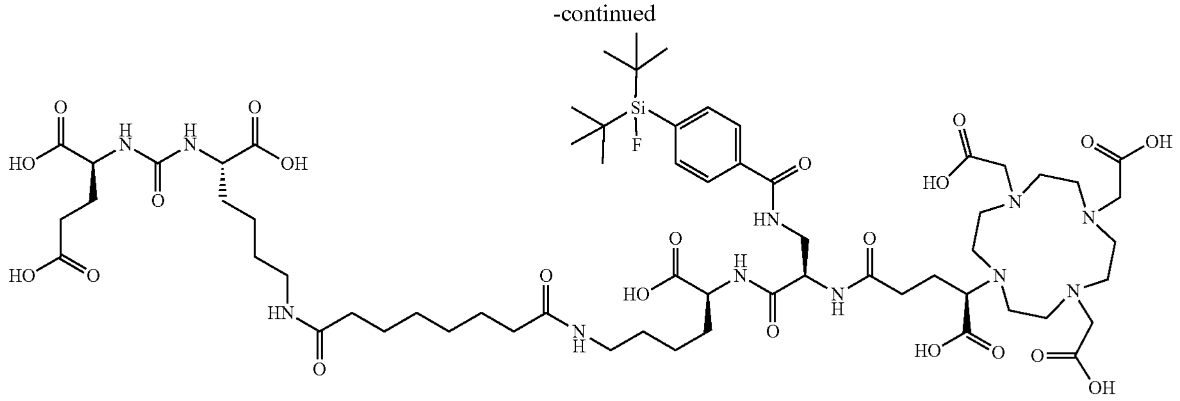
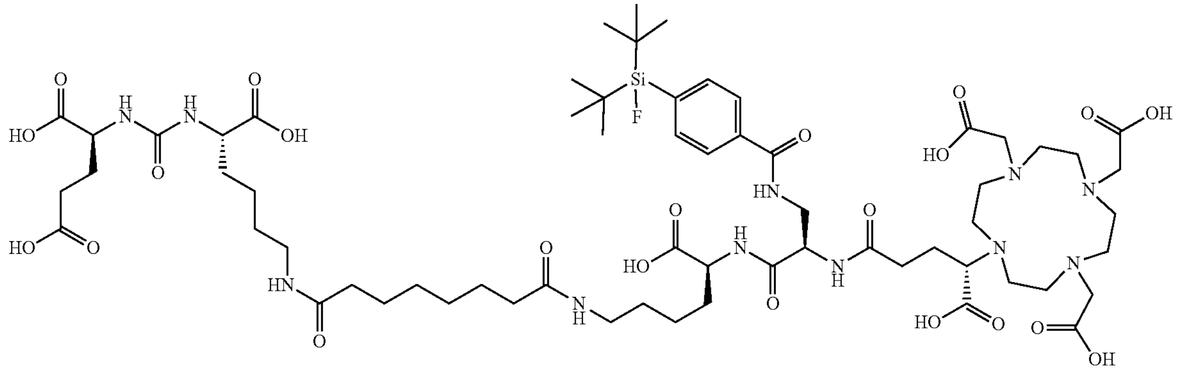
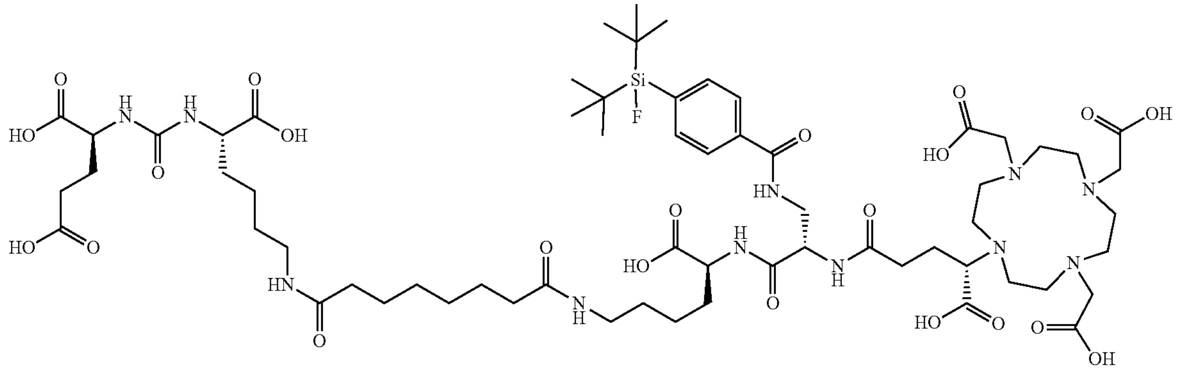
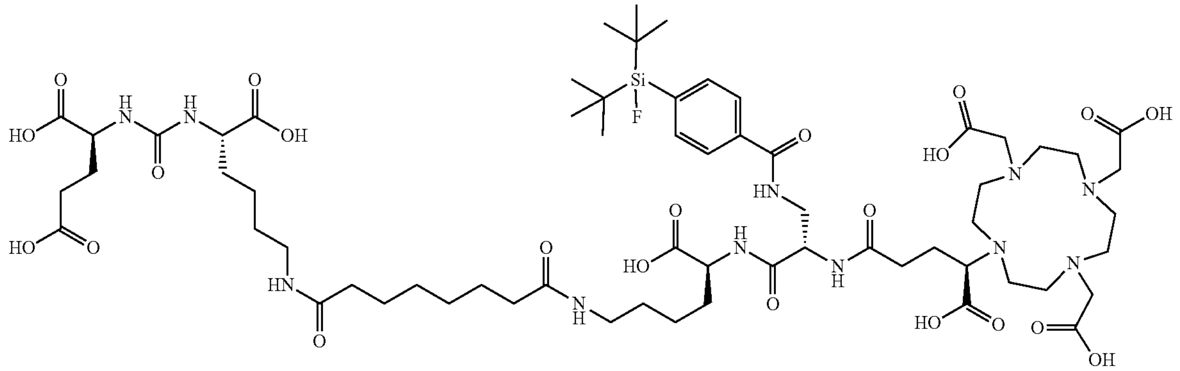

-continued
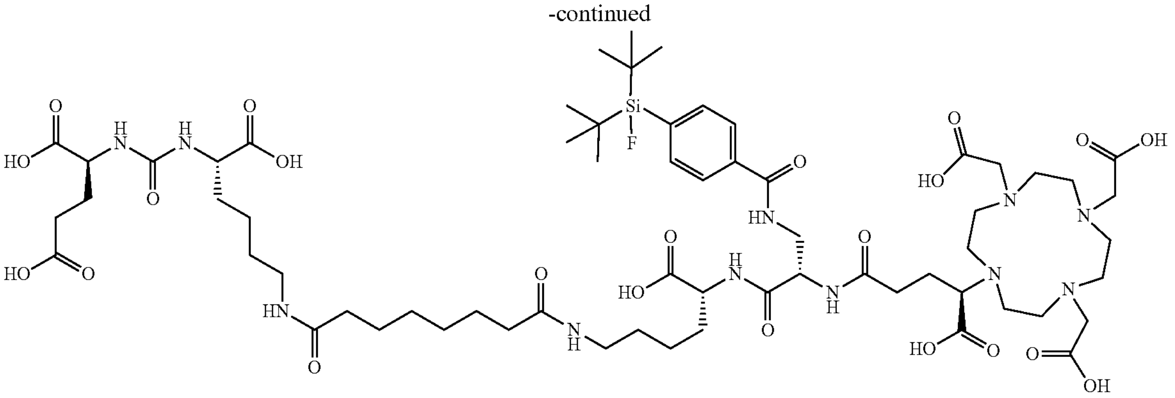
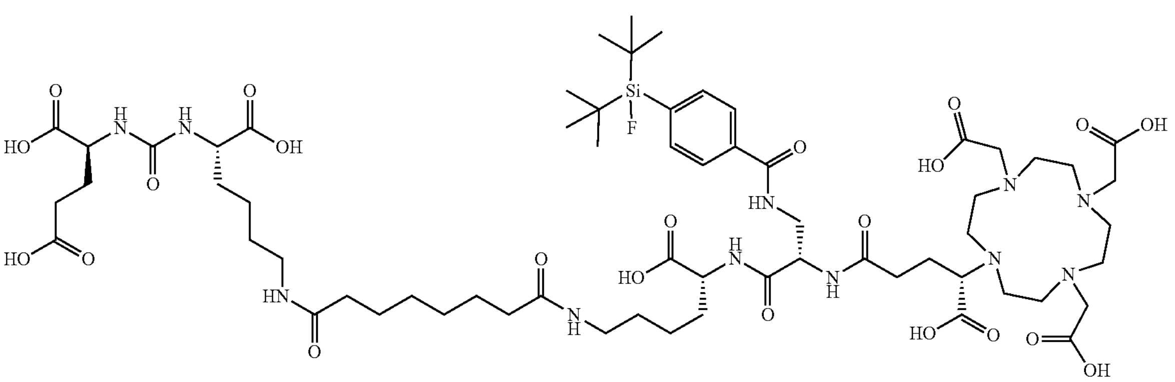
(6)
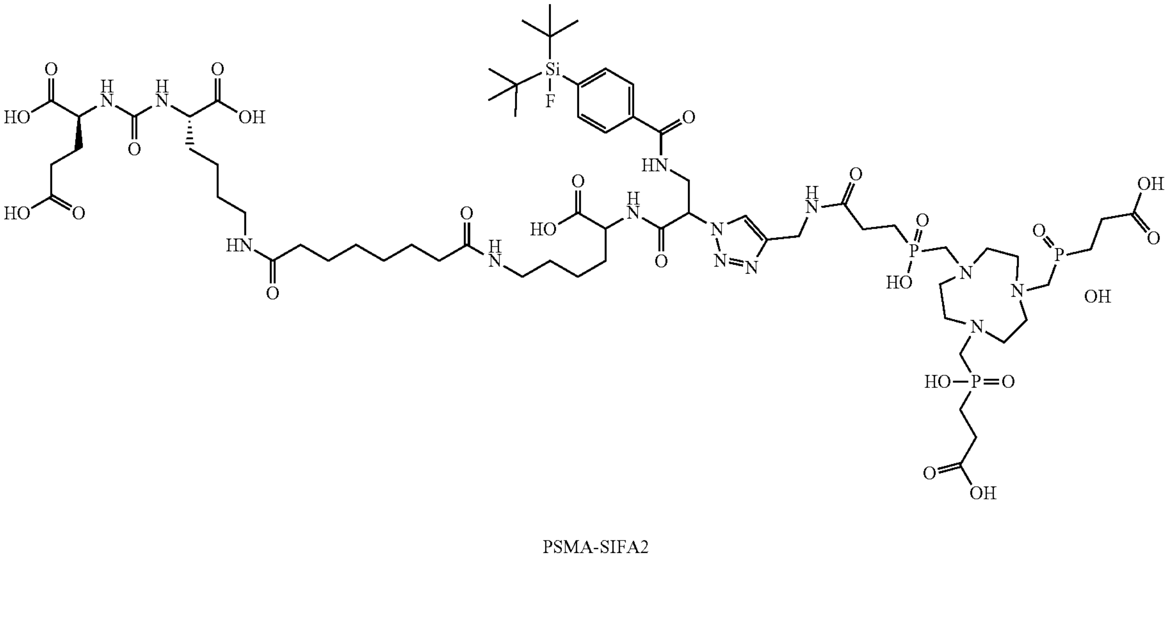
PSMA-SIFA2 and isomers thereof
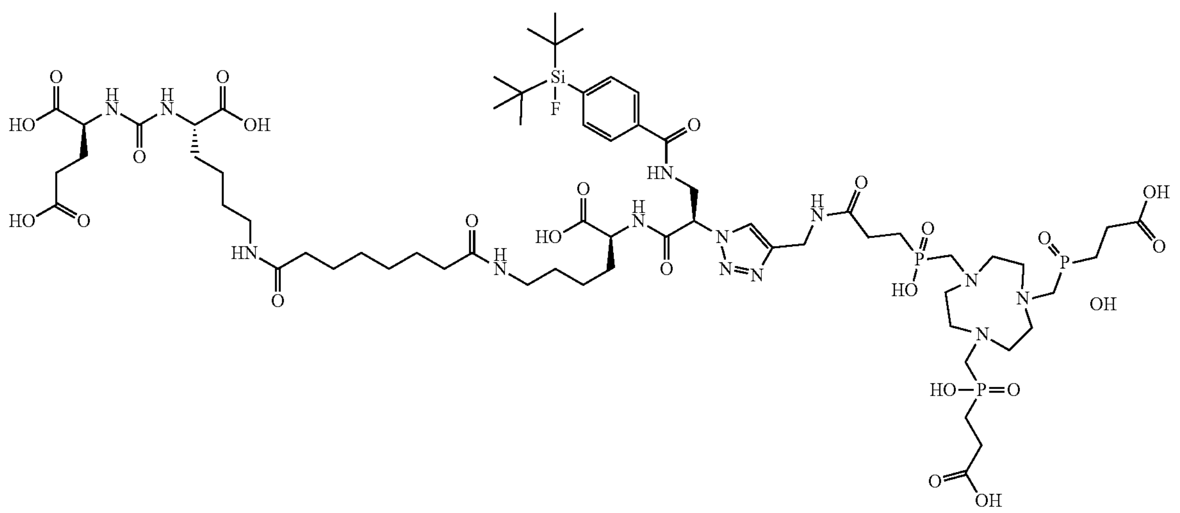
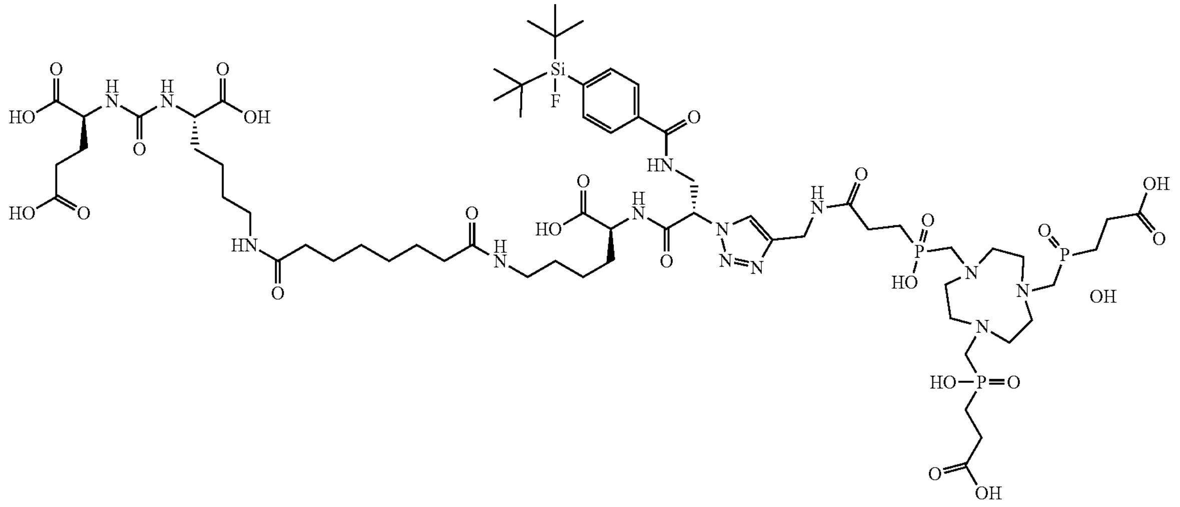
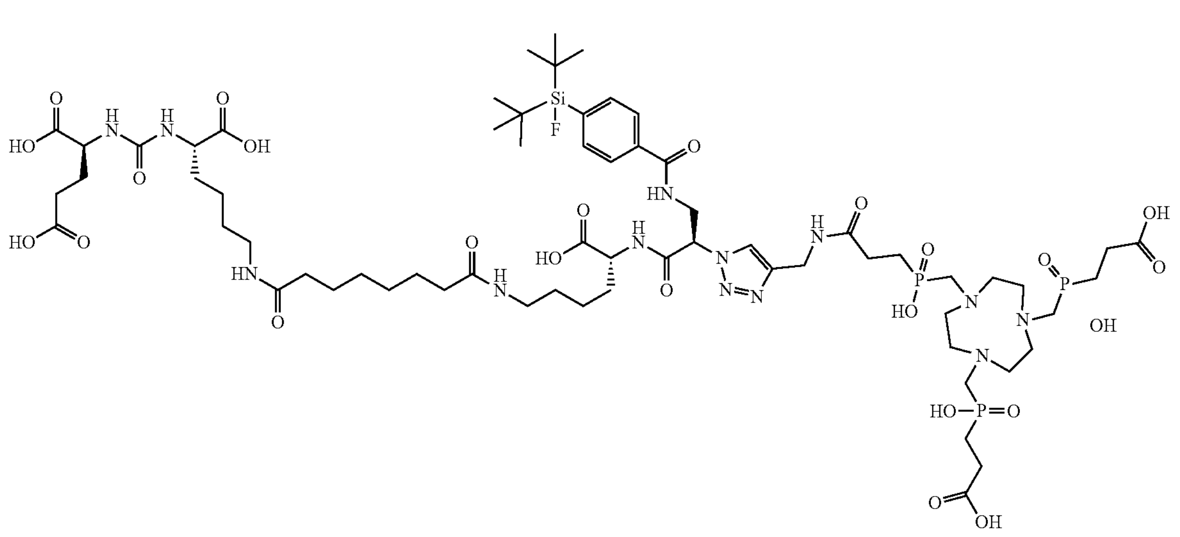

-continued
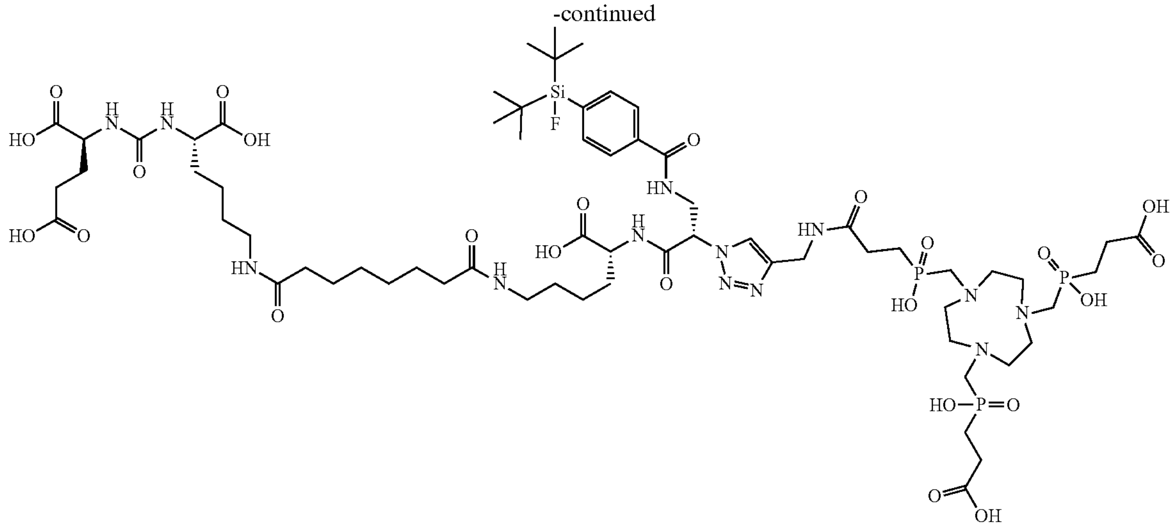
(7)
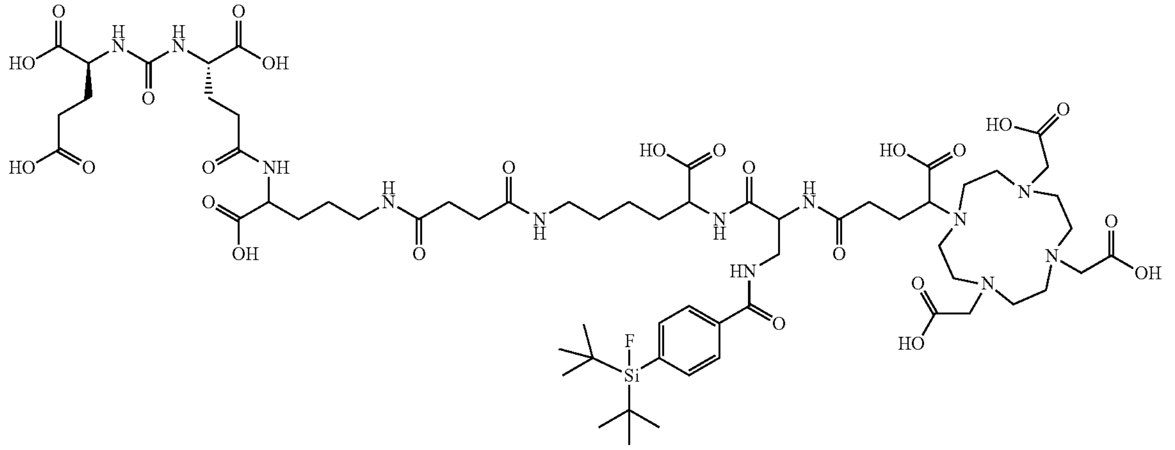
PSMA-SIFA3
and isomers thereof
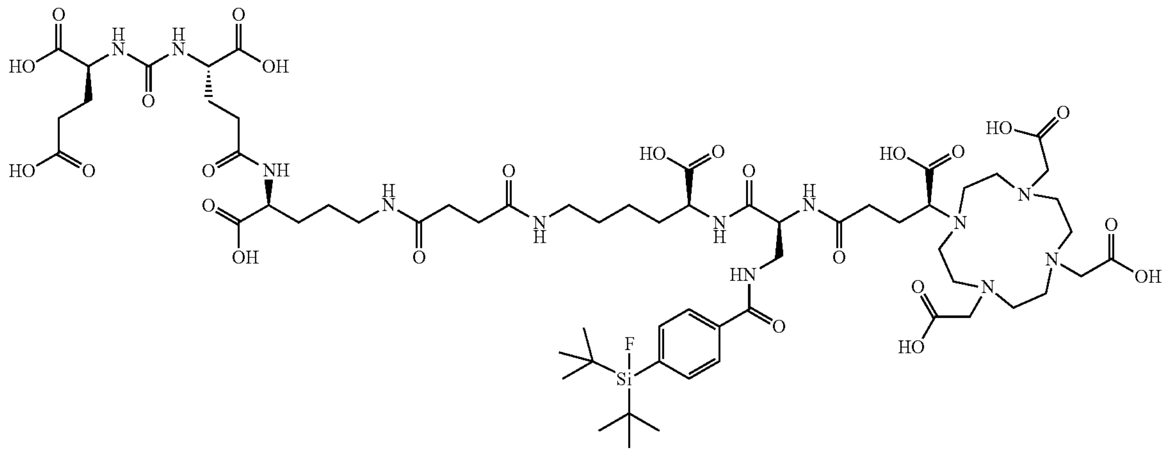

-continued
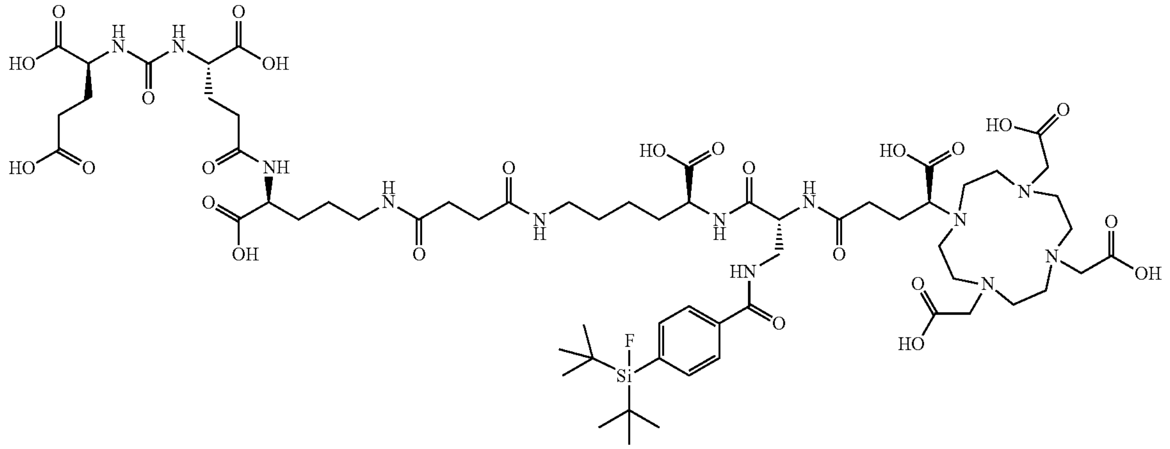
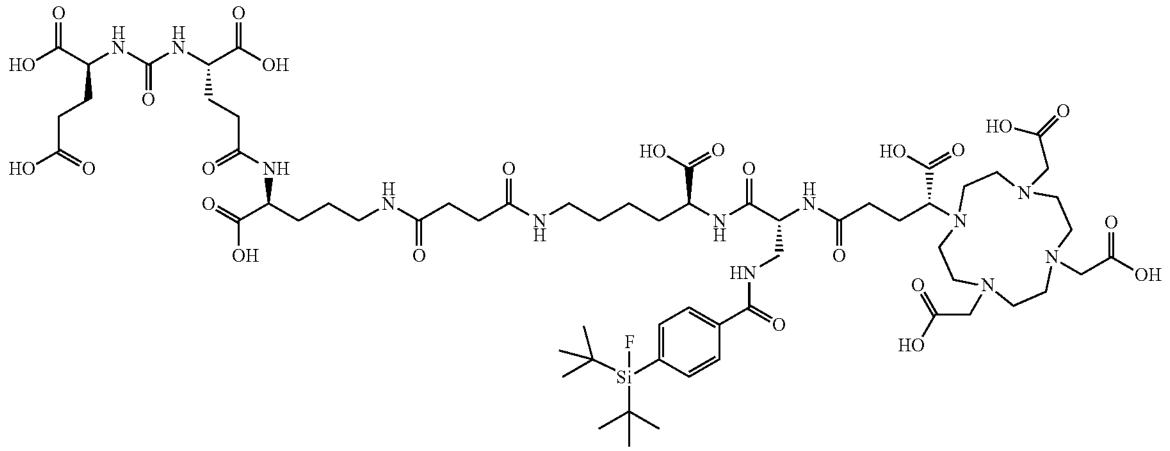
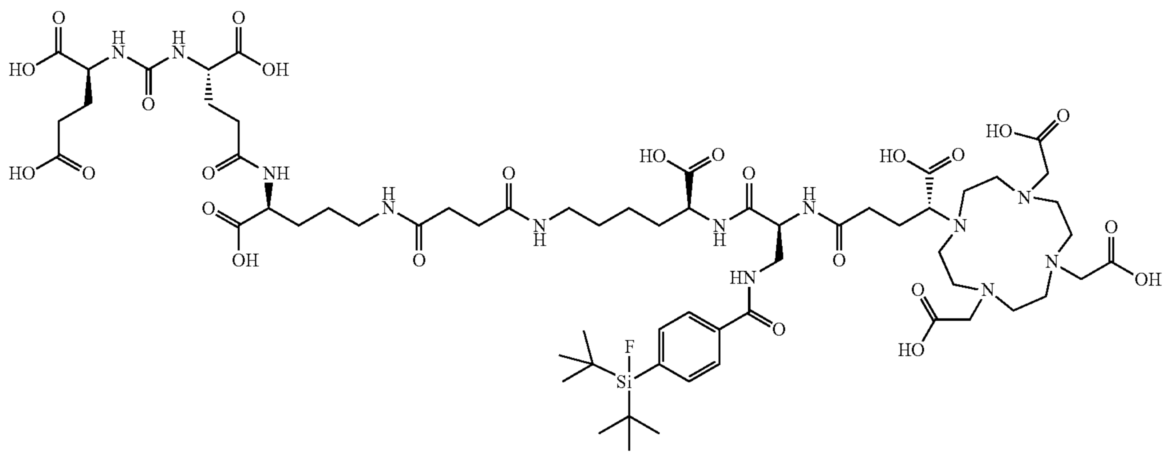

-continued
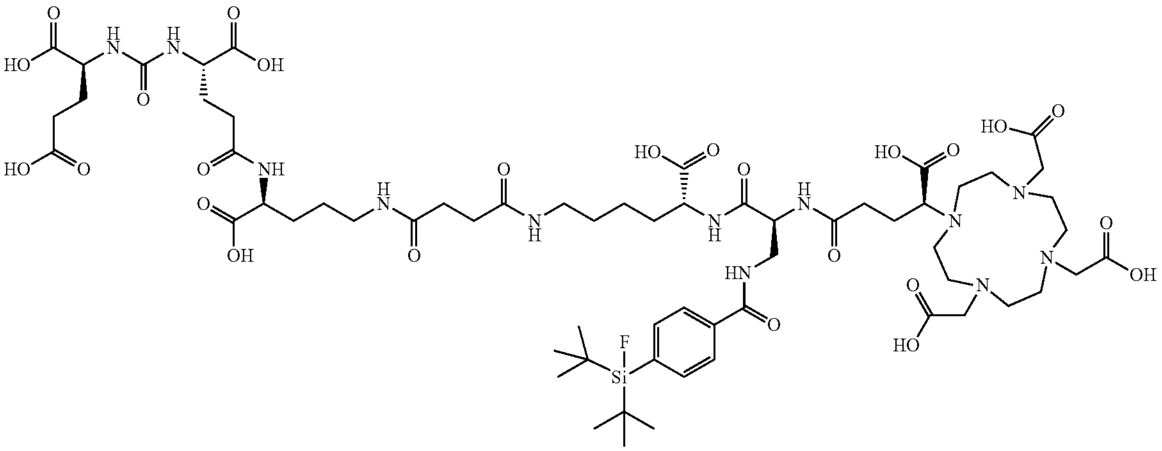
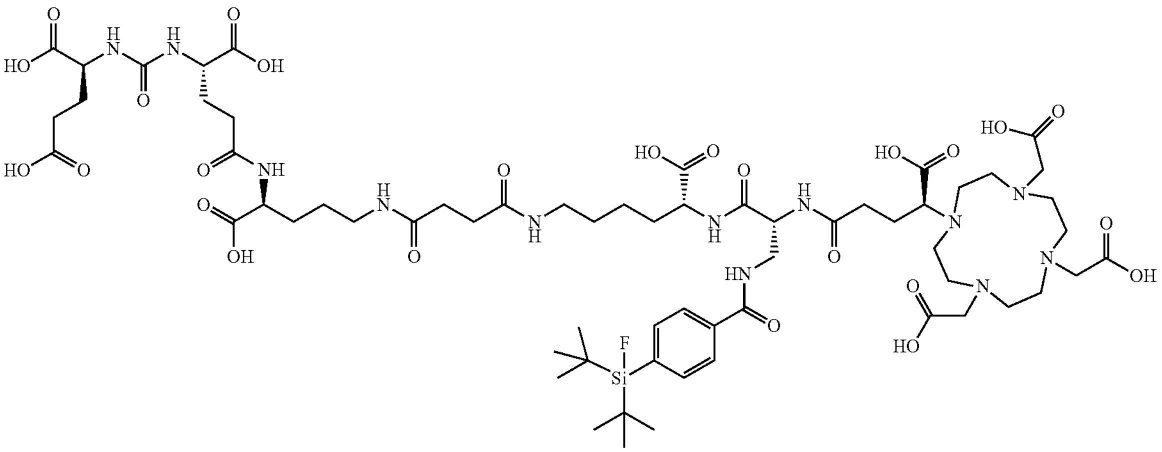
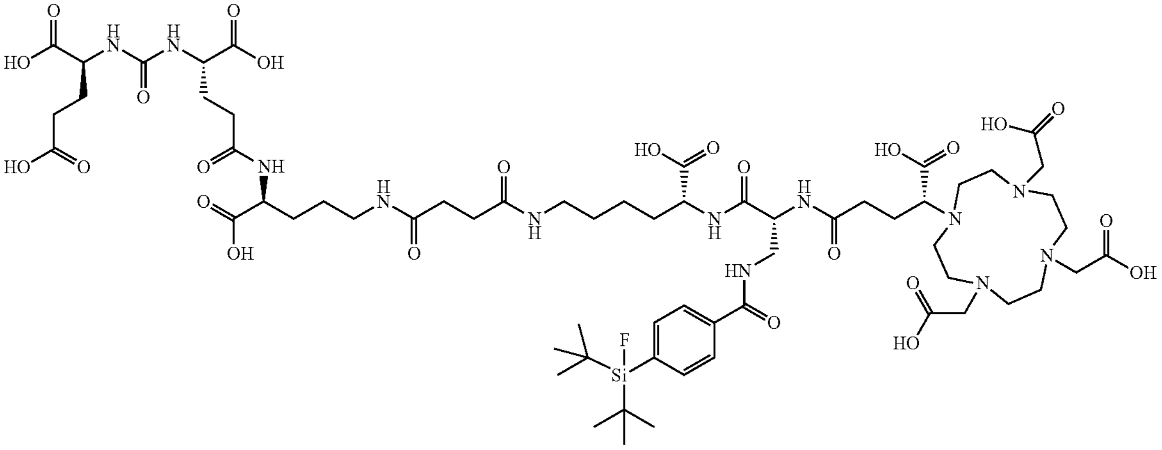

-continued
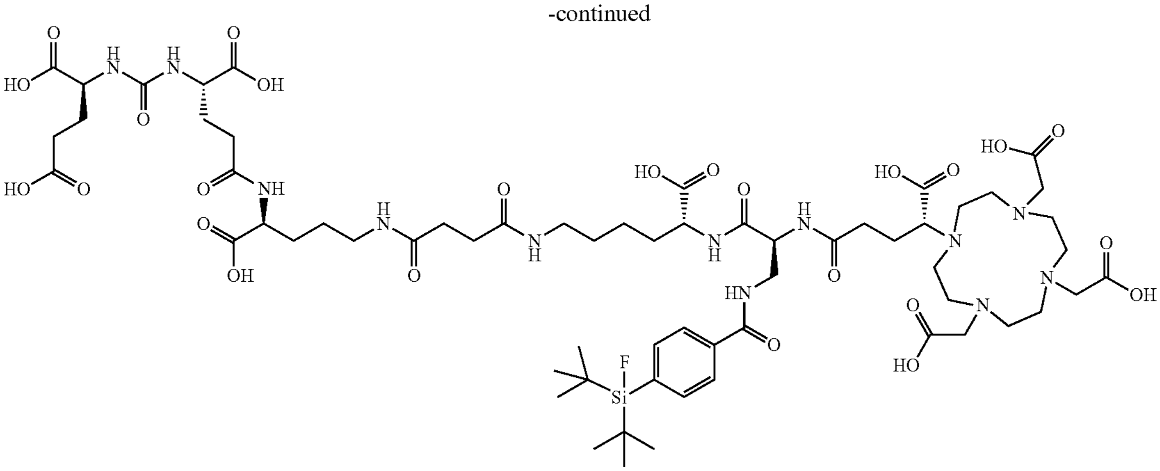
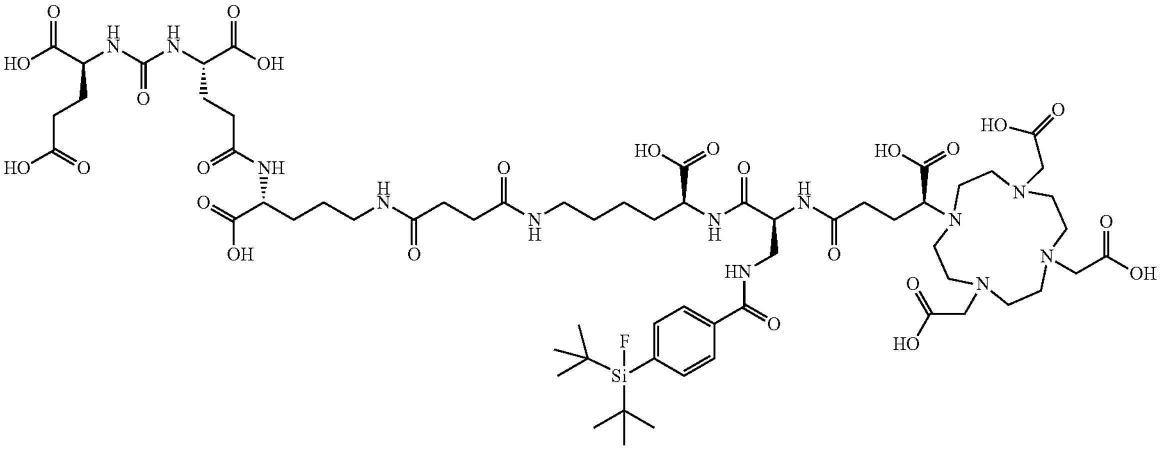
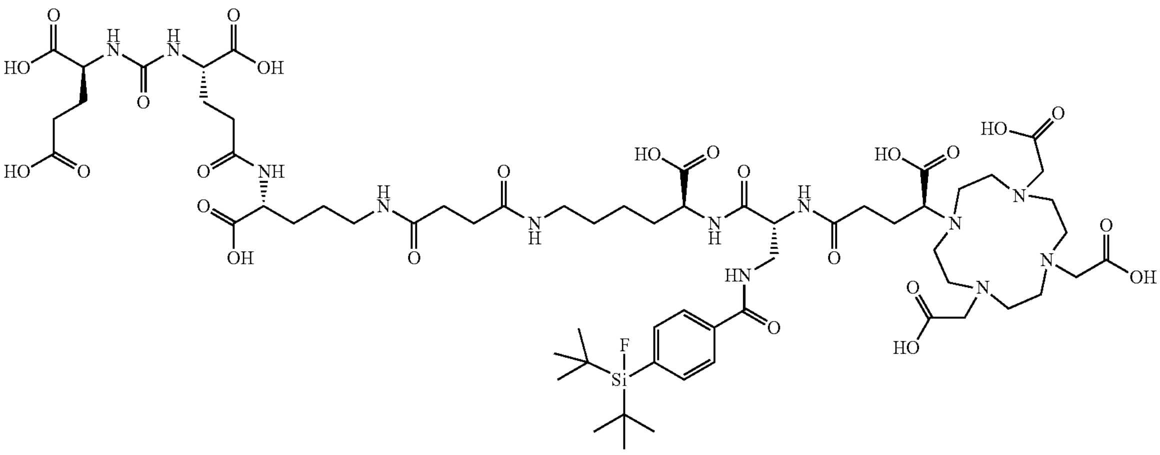

-continued
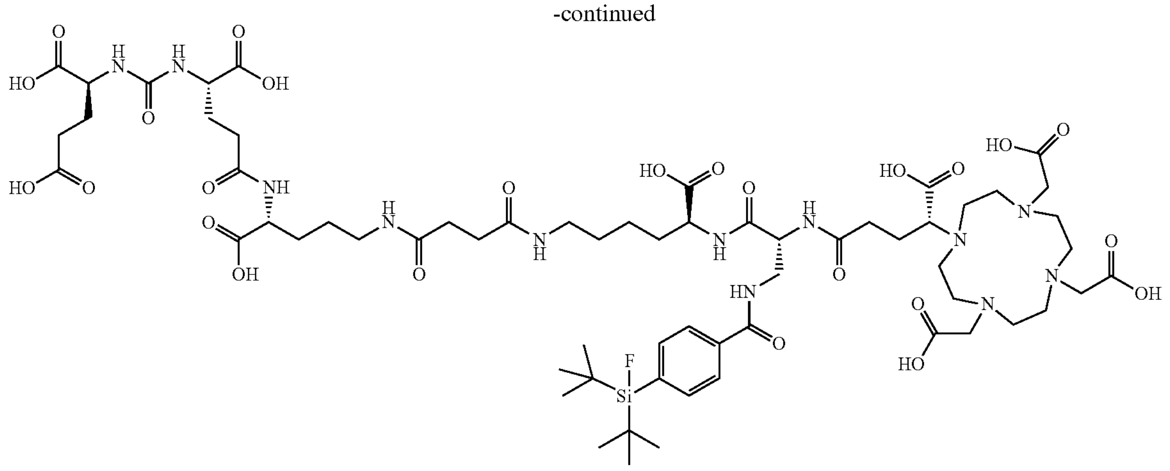
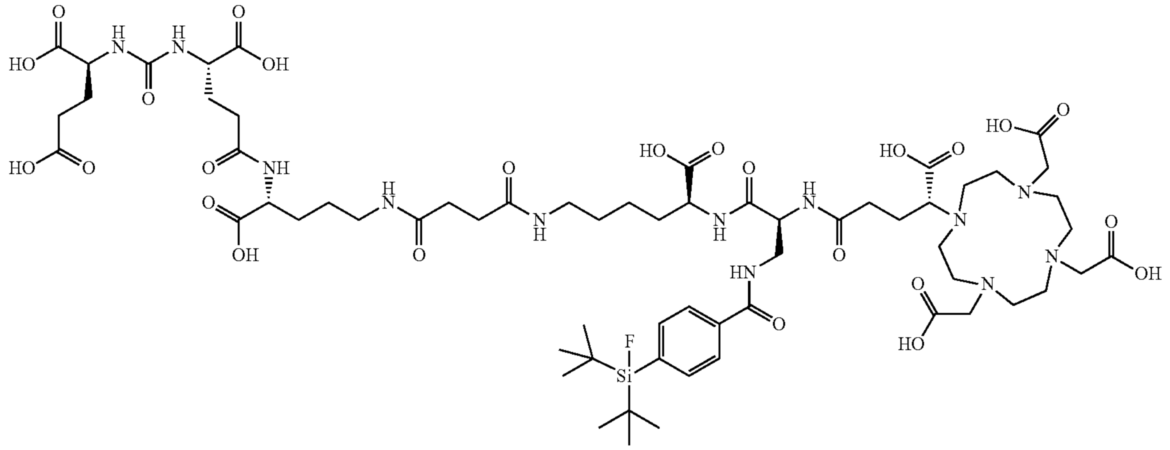
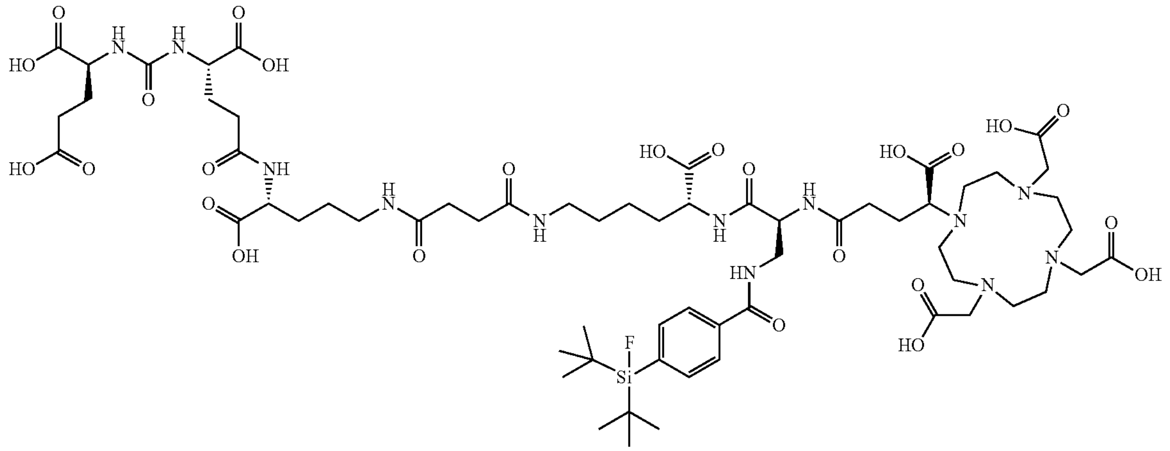

-continued
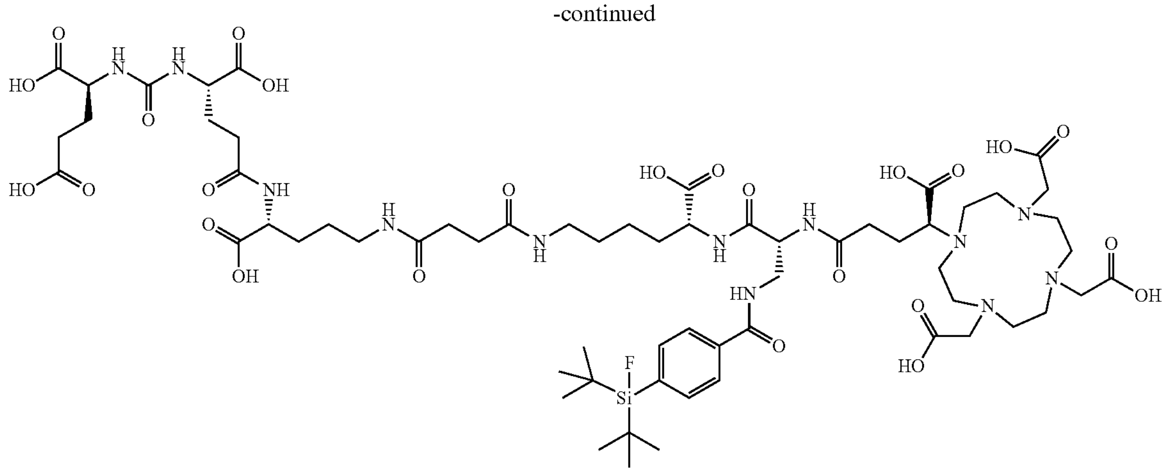
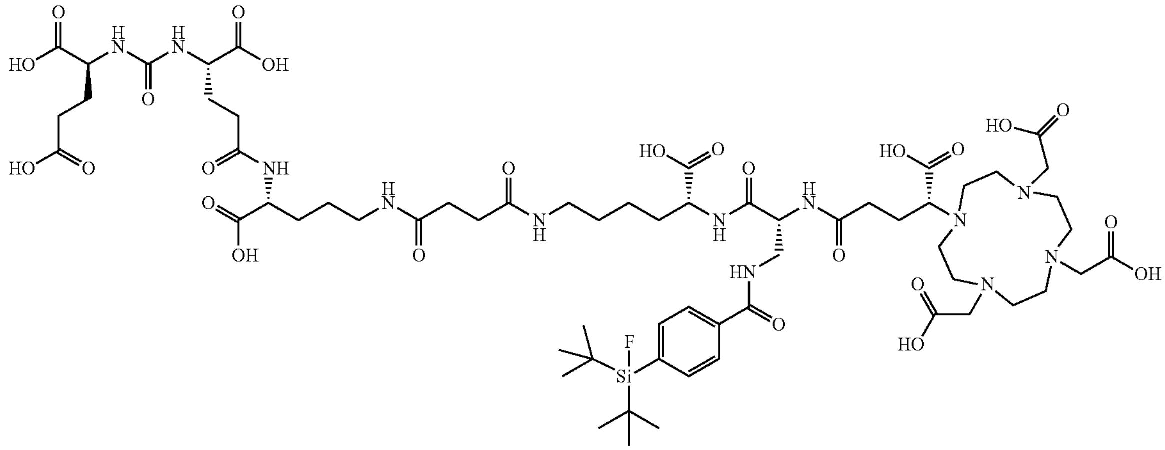
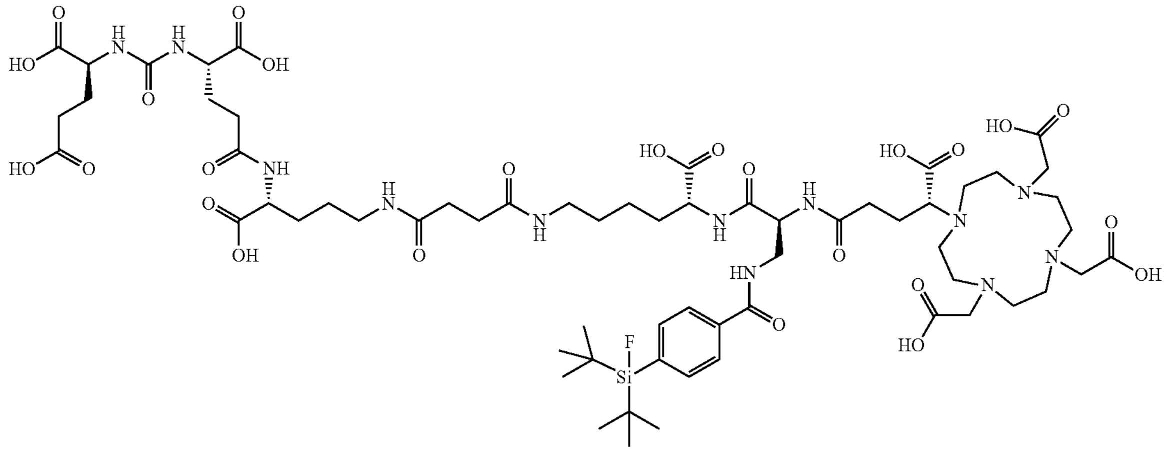

-continued
(8)
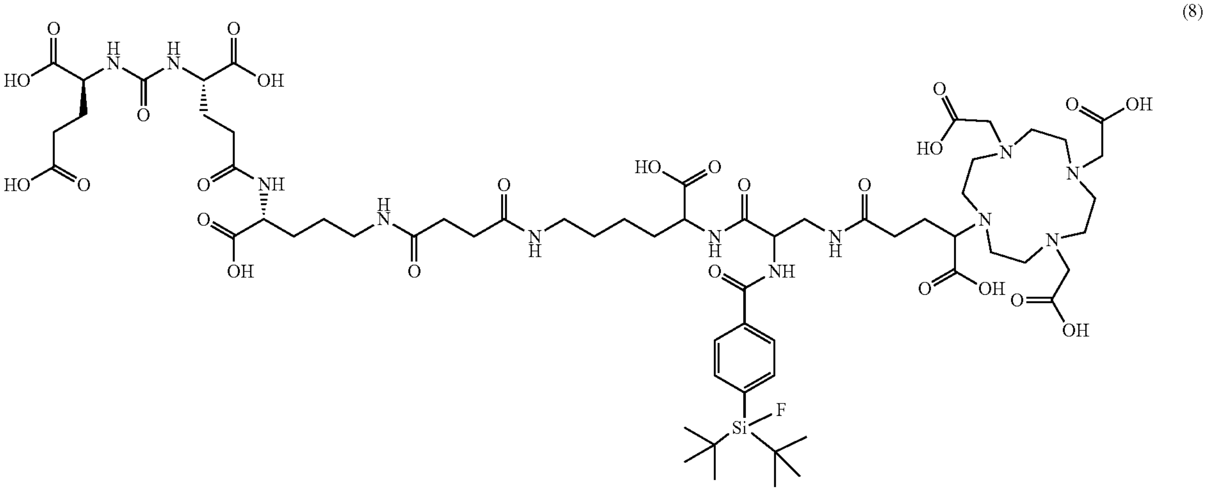
PSMA-SIFA4
and isomers thereof
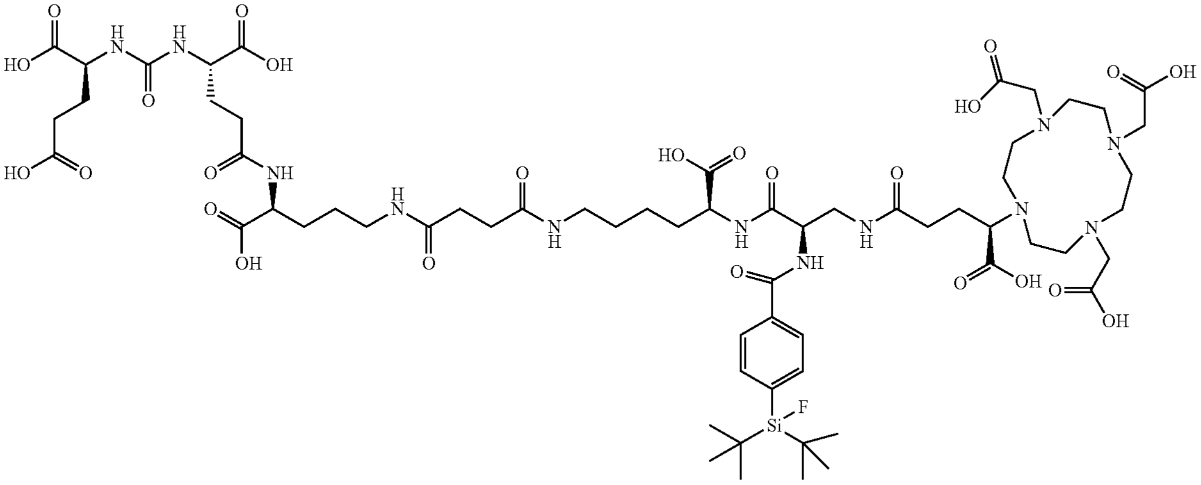
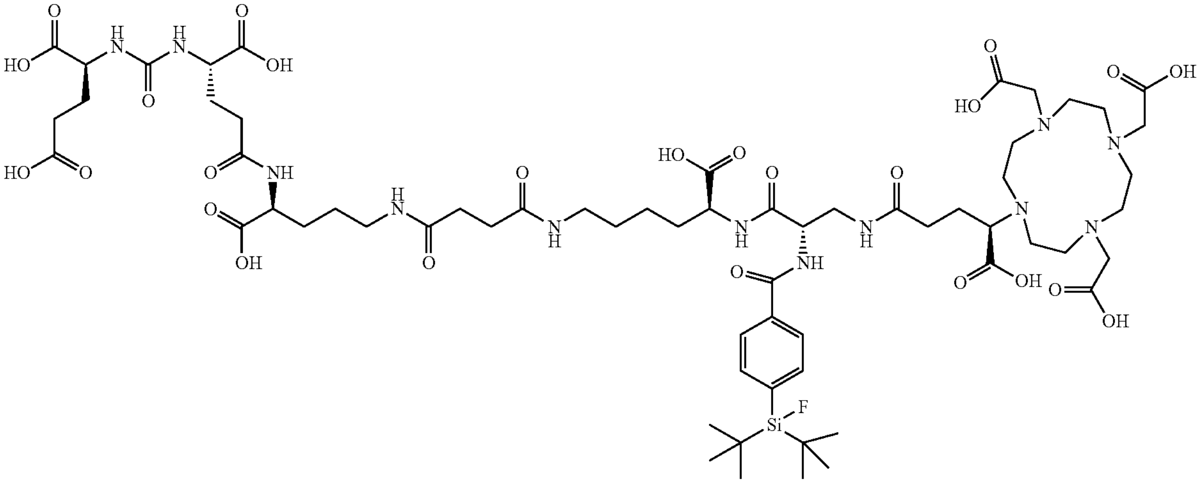

-continued
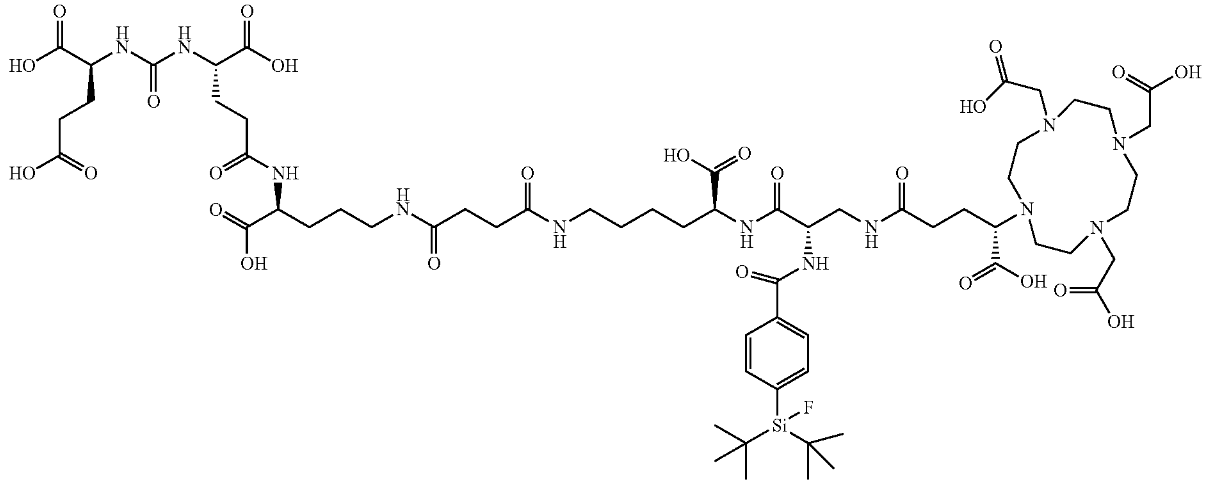
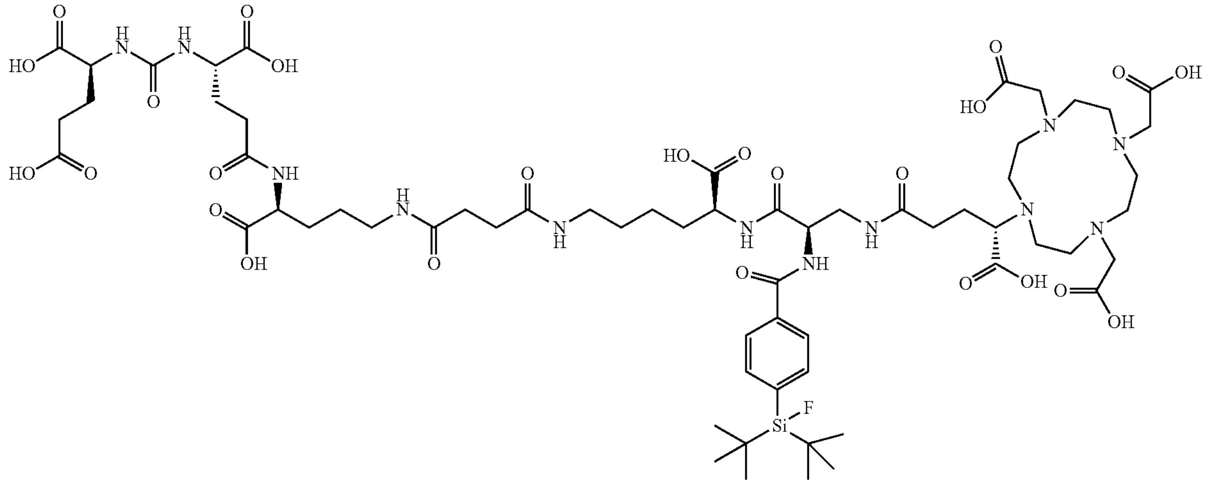
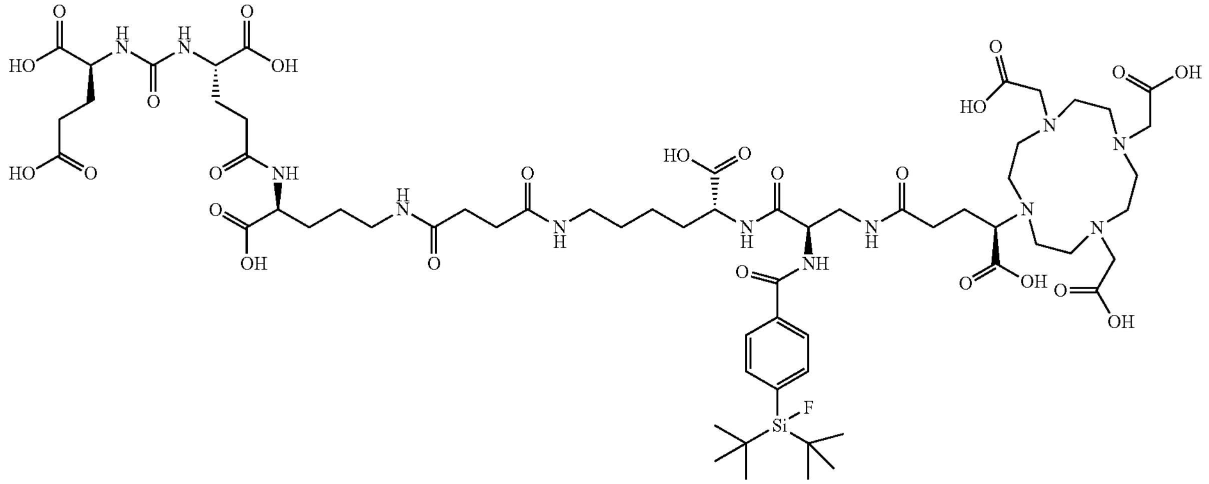

-continued
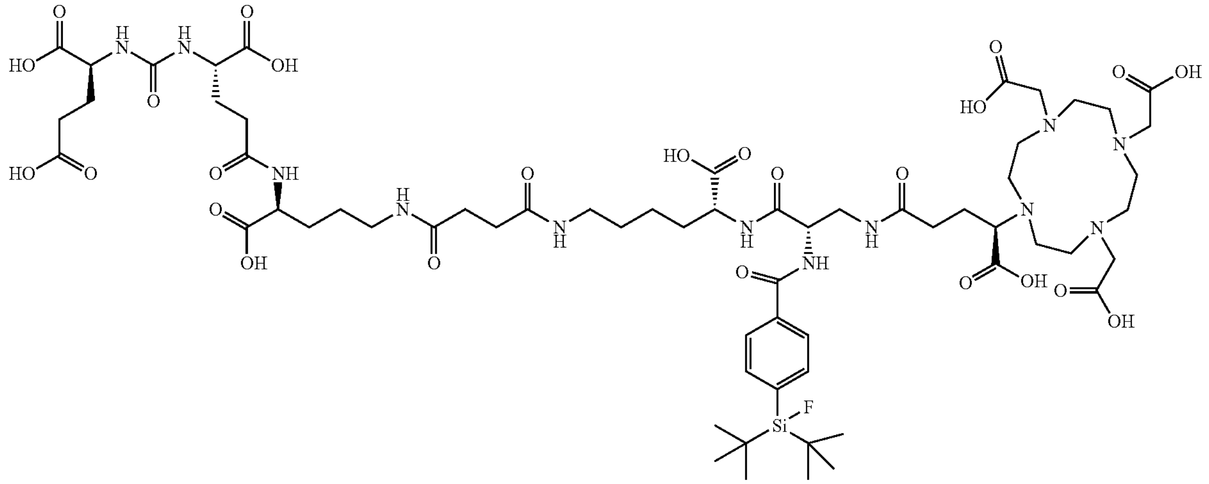
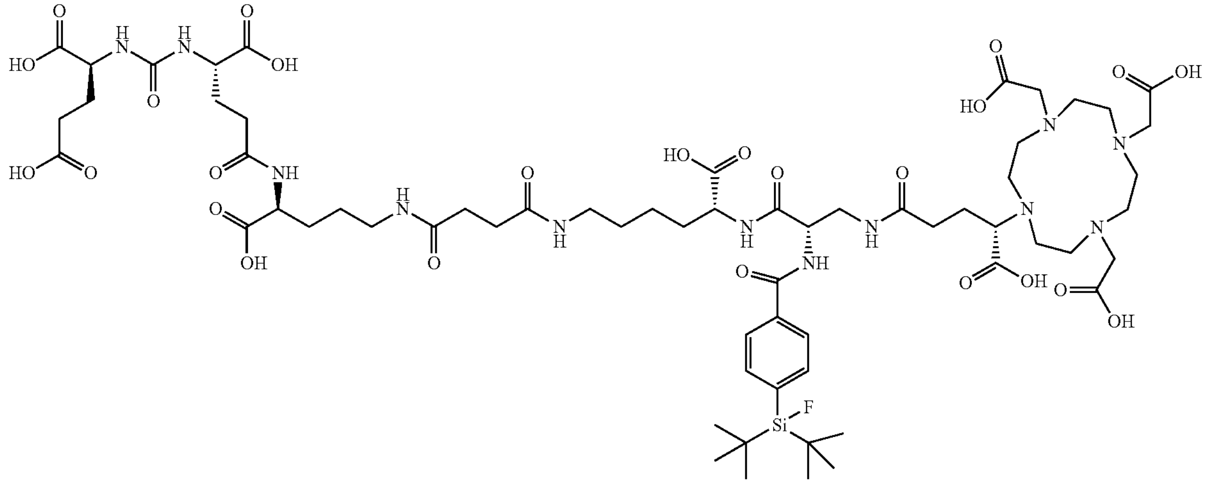
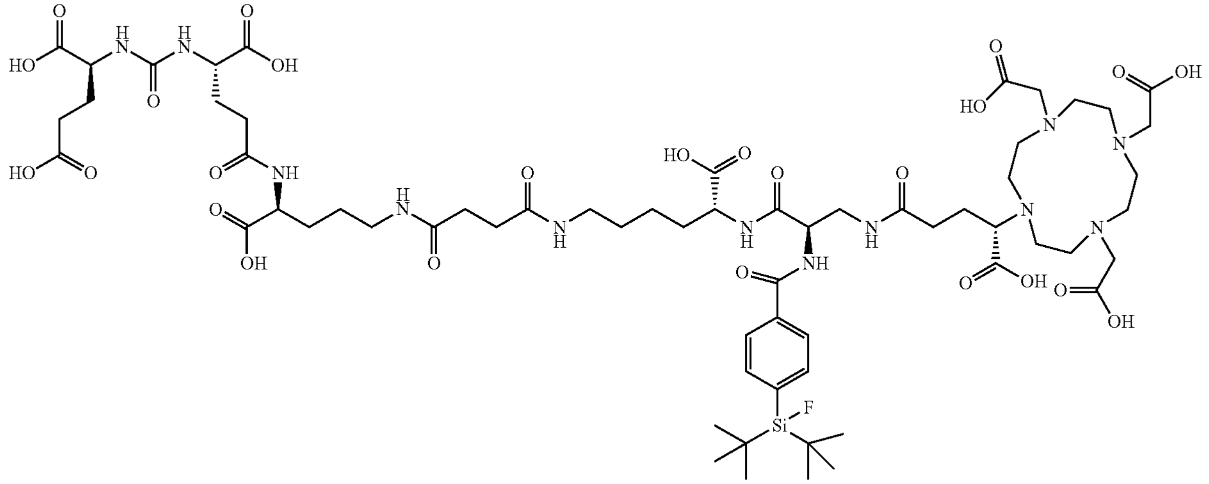

-continued
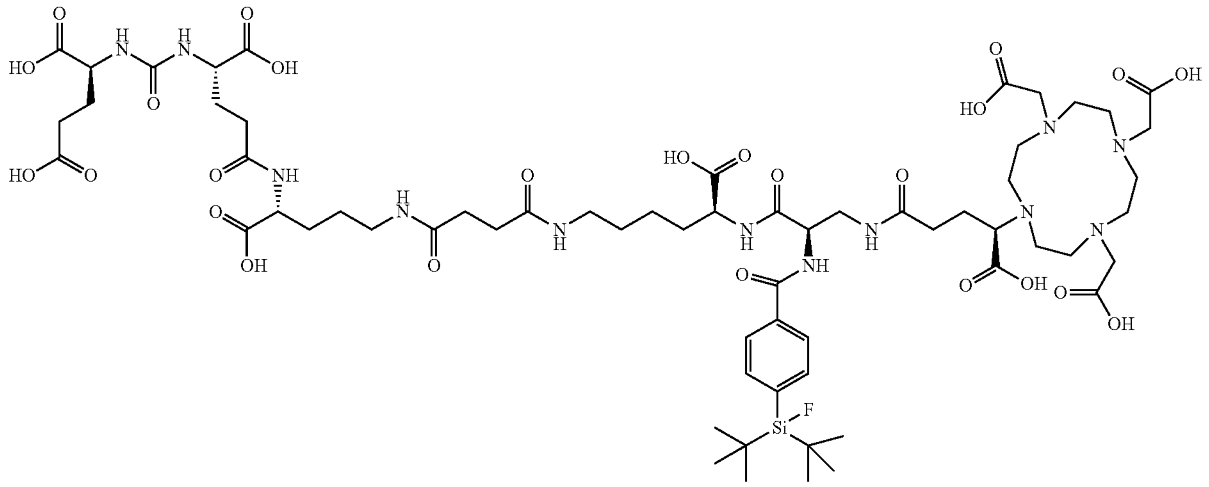
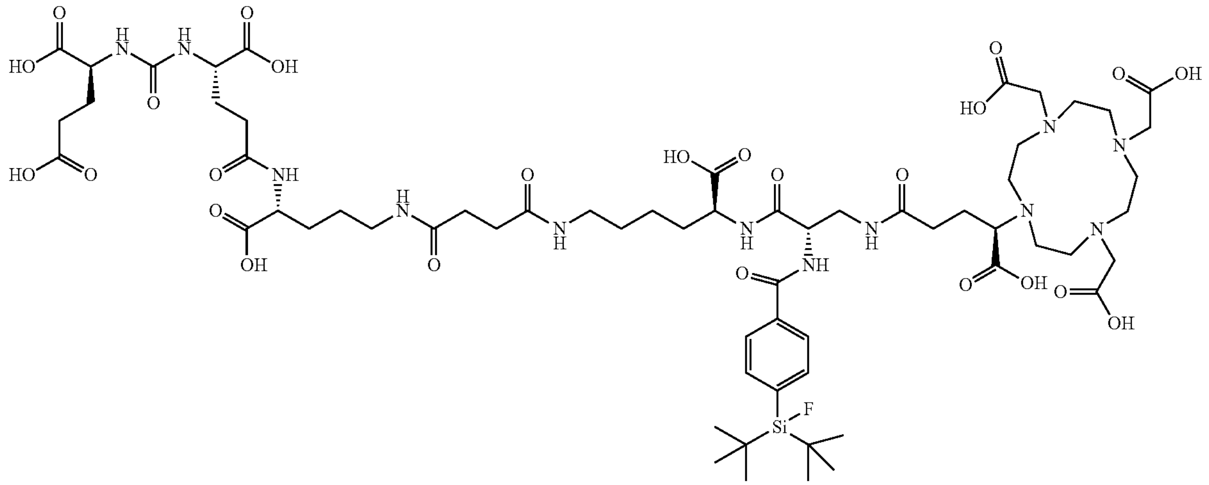
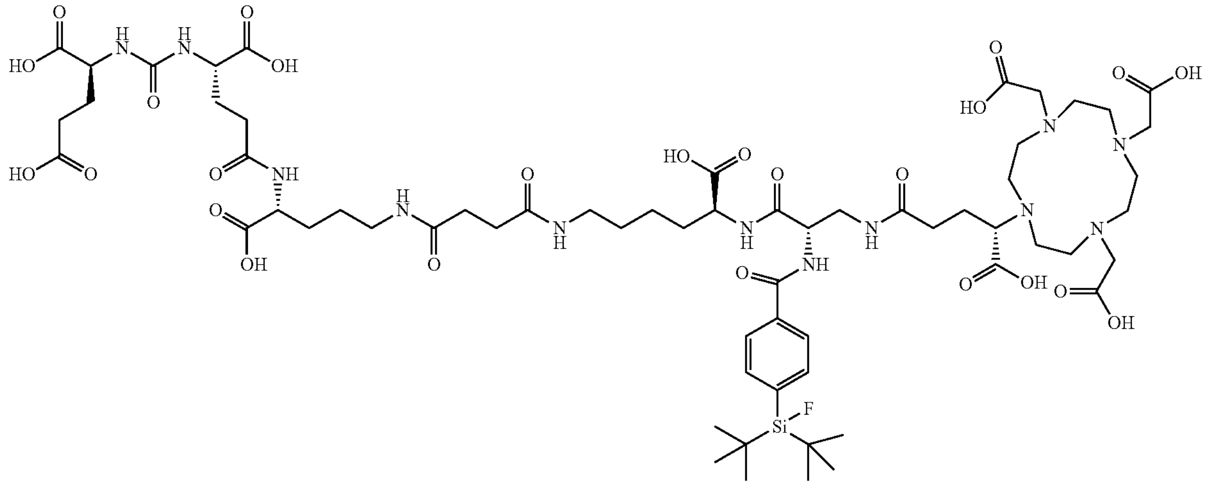

-continued
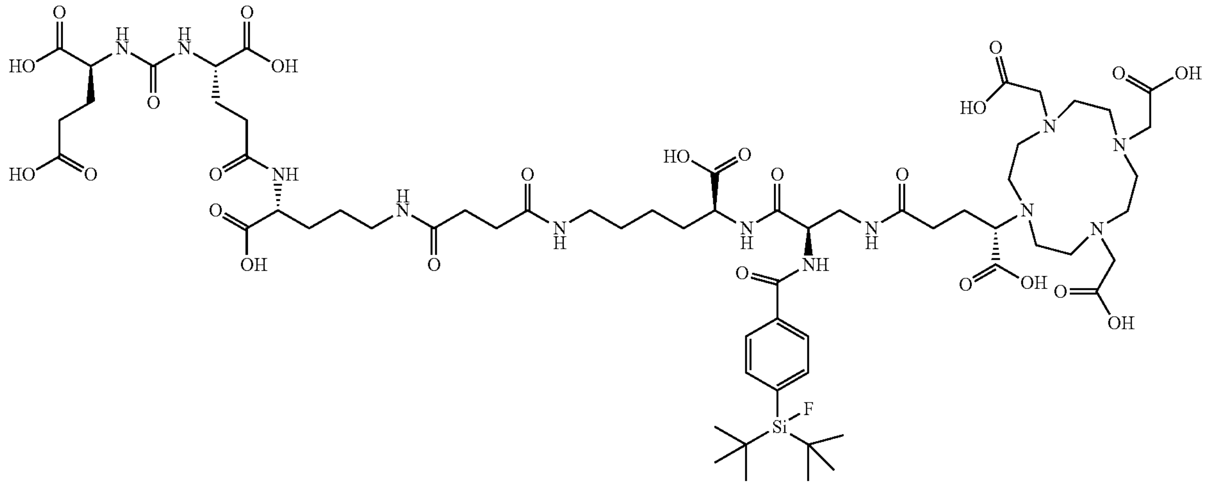
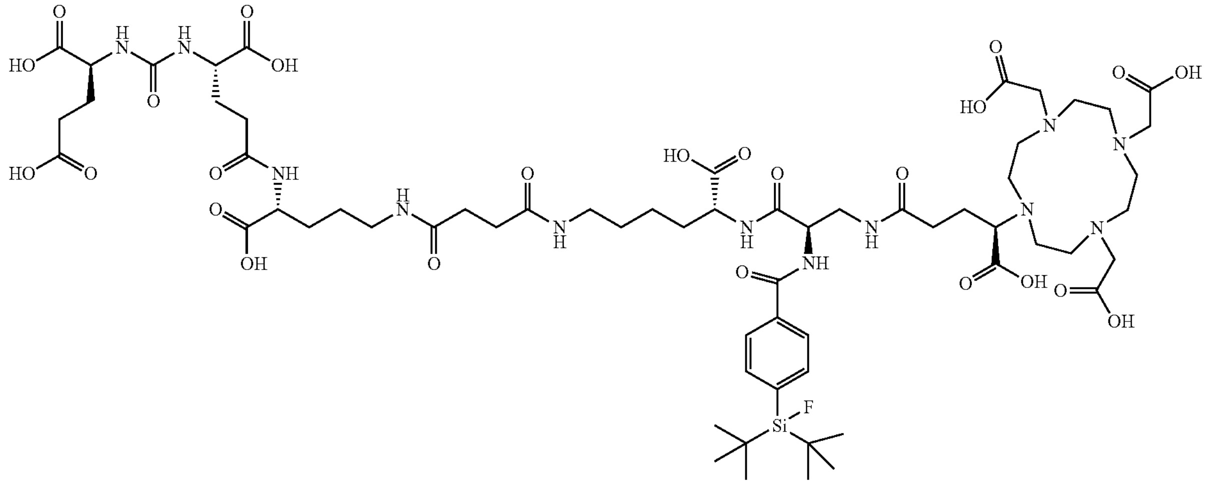
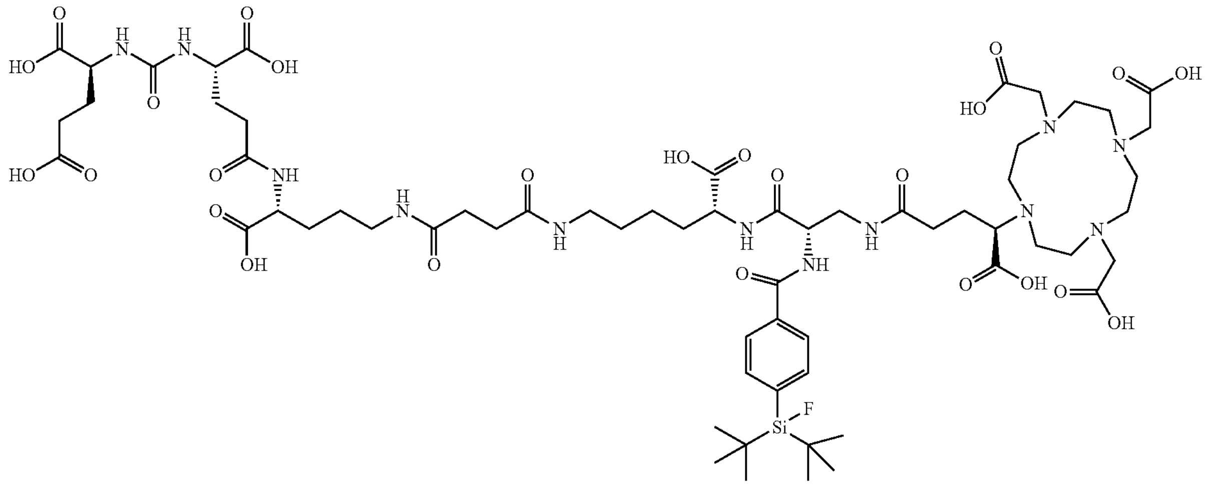

-continued
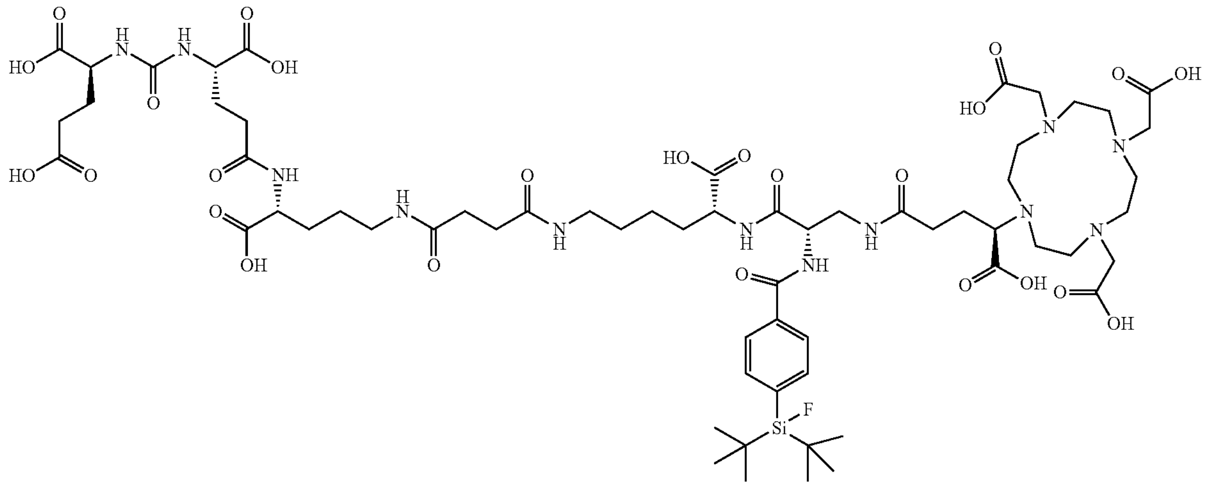
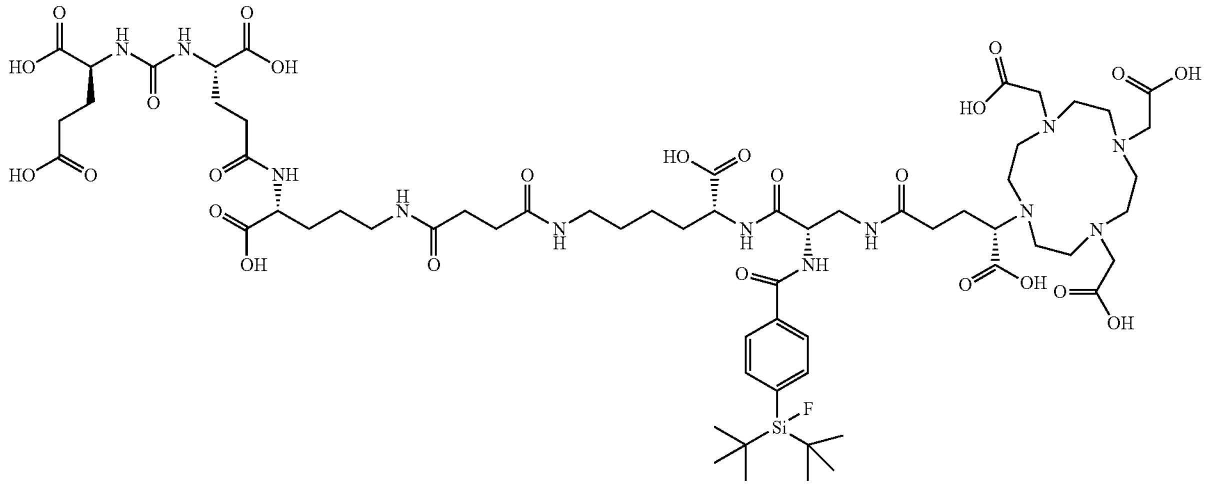
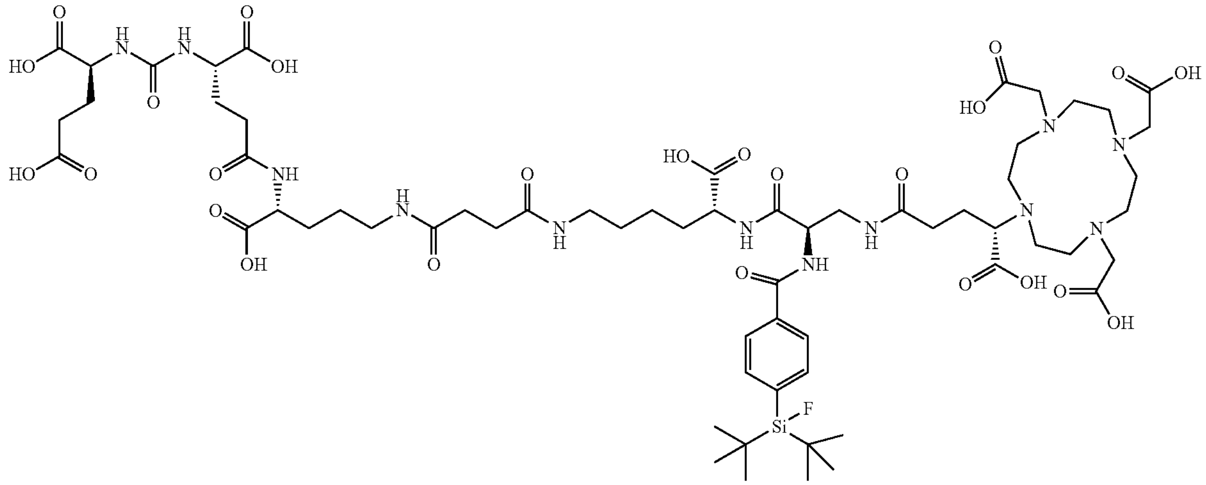

-continued
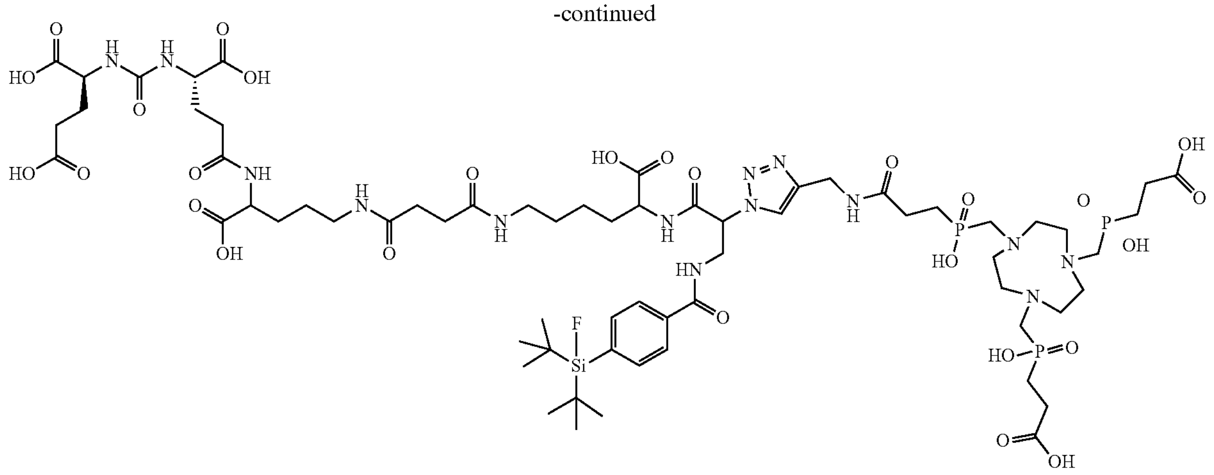
PSMA-SIFA5 (9)
and isomers thereof
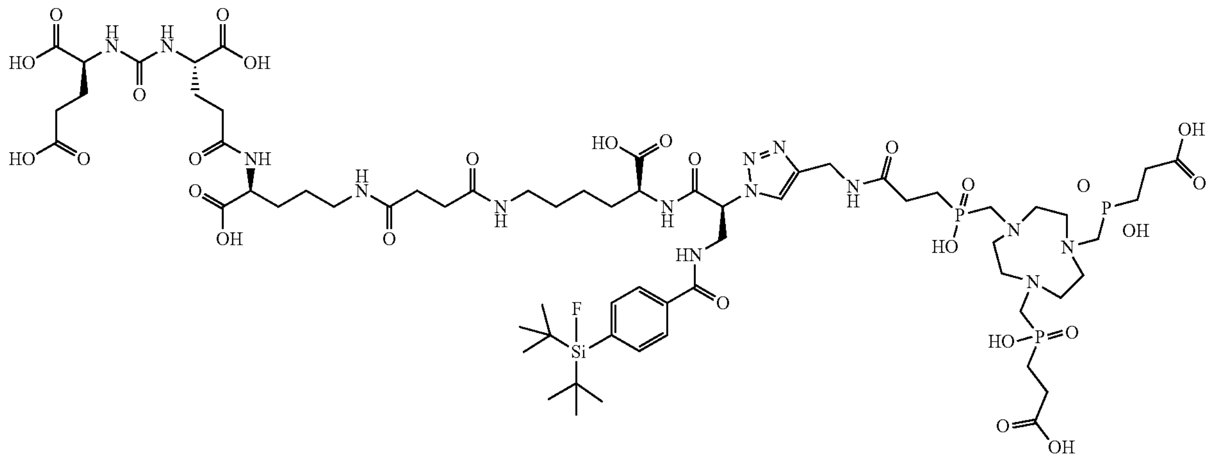
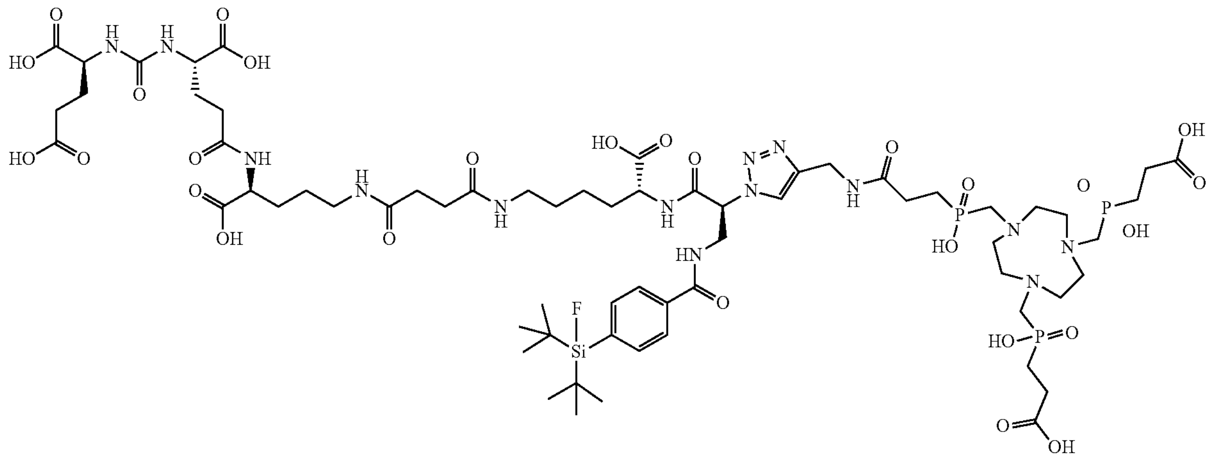

-continued
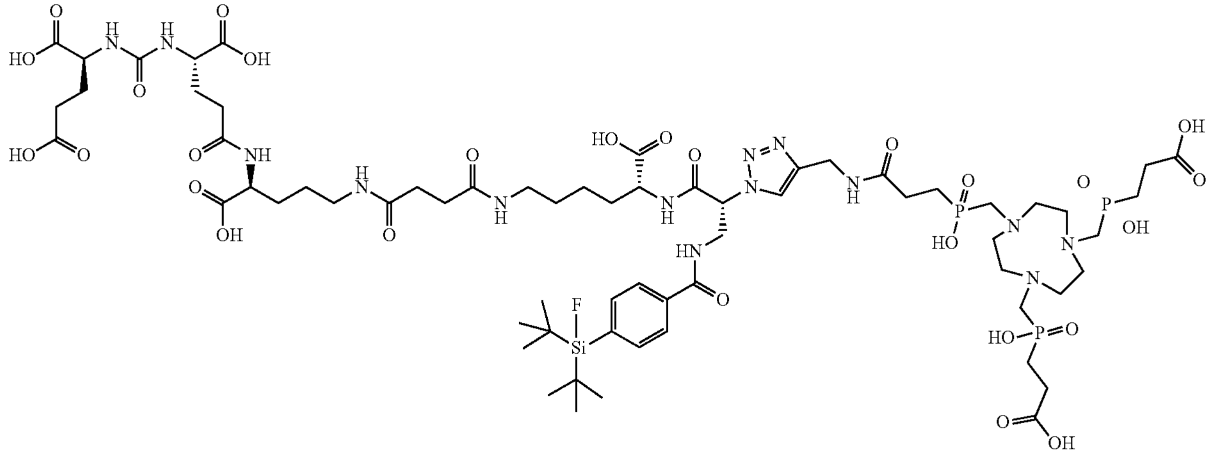
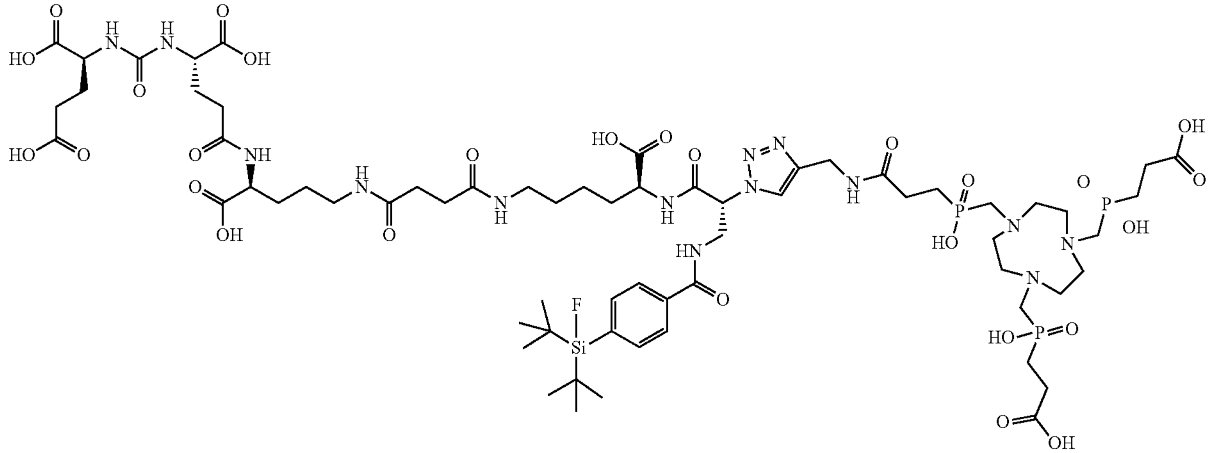
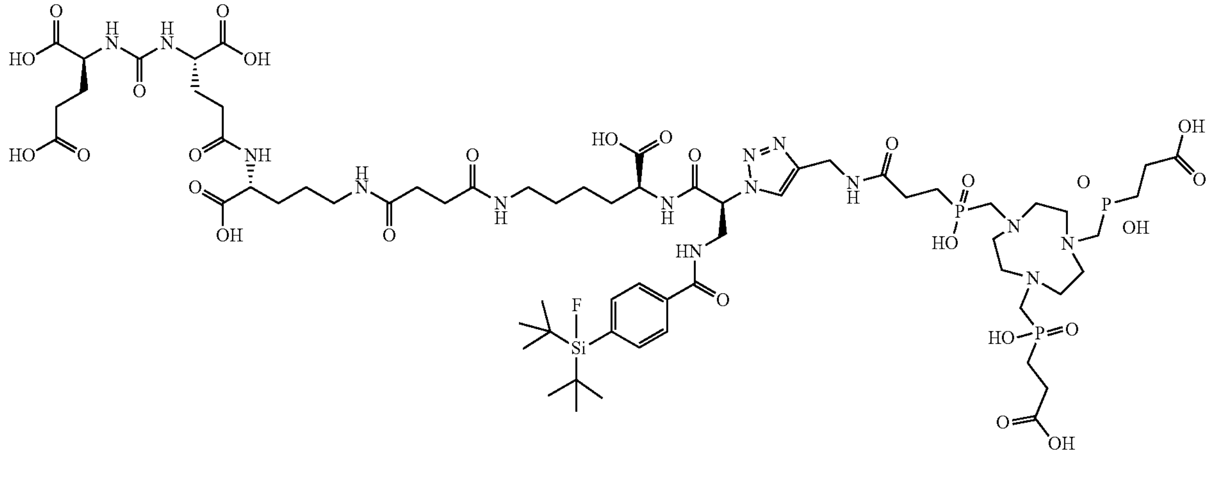

-continued
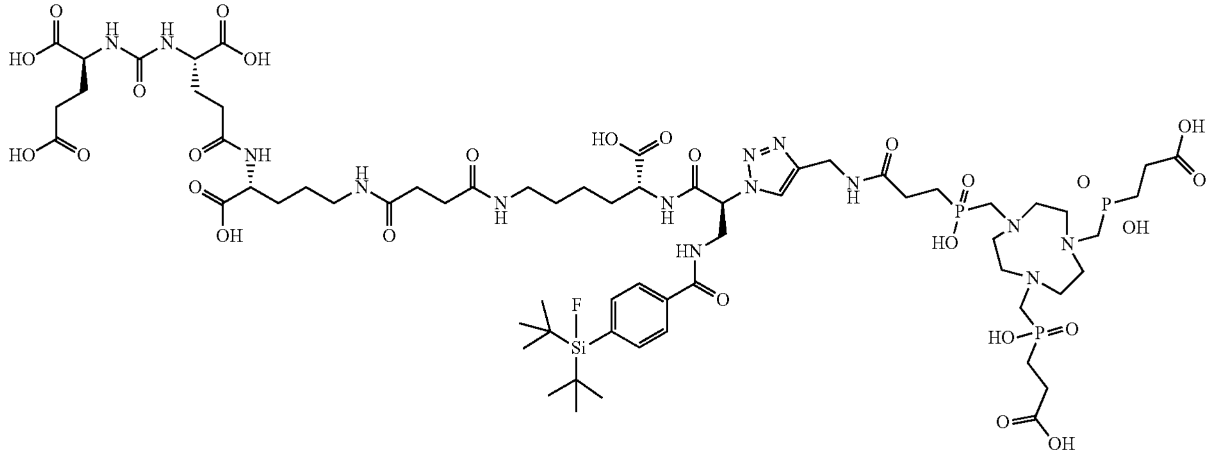
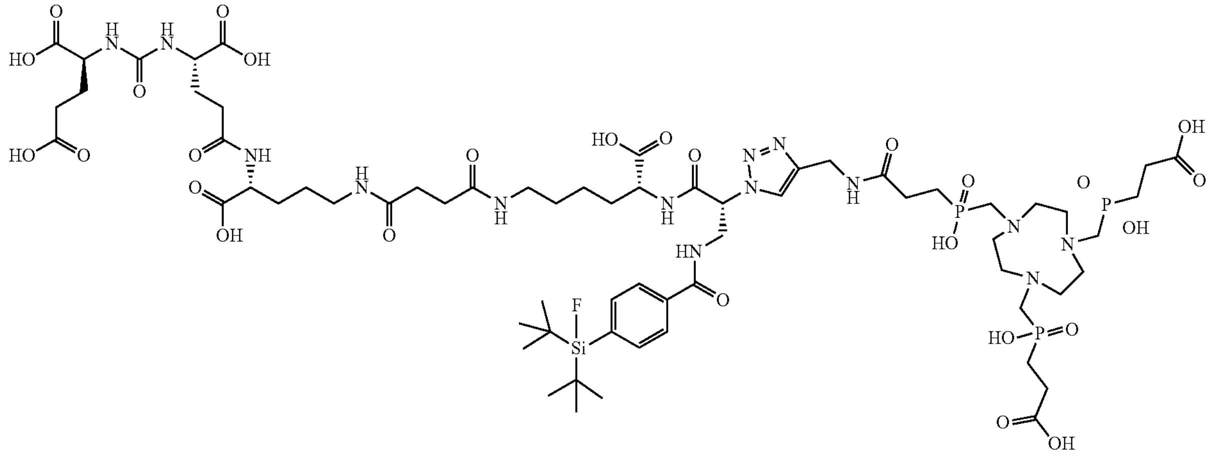
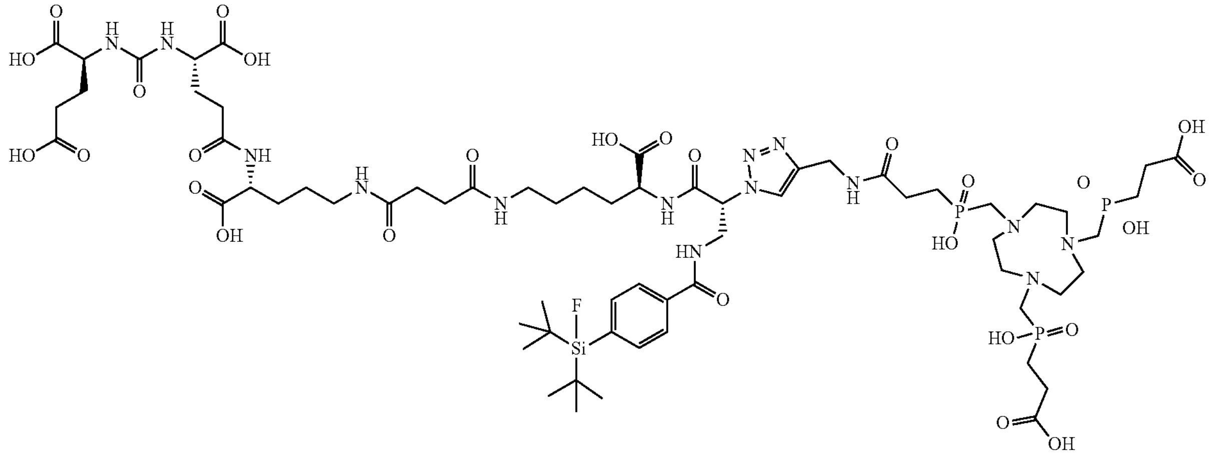

-continued
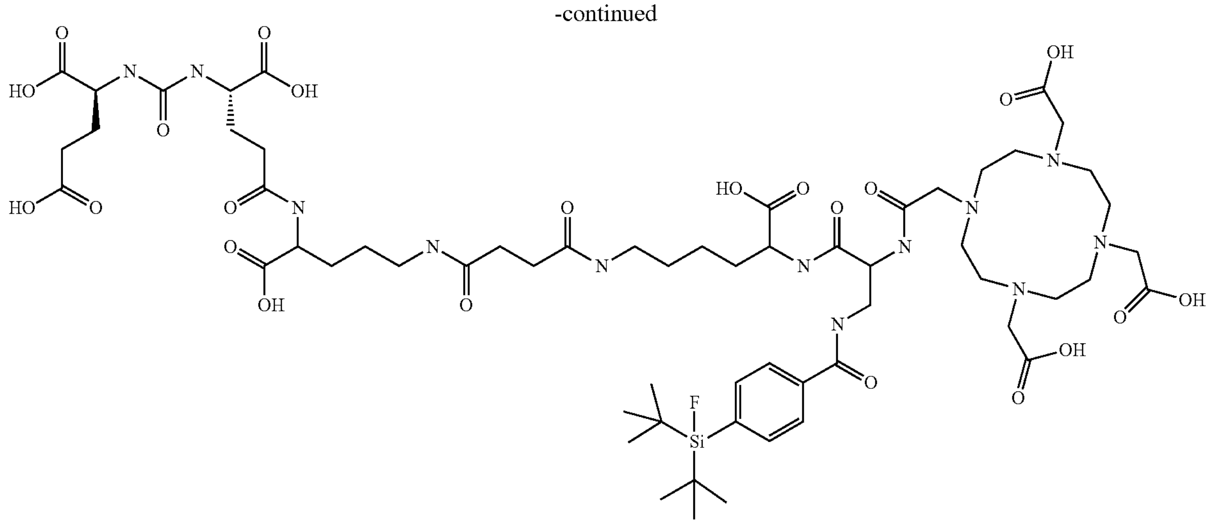
PSMA-SIFA 10
and isomers thereof:
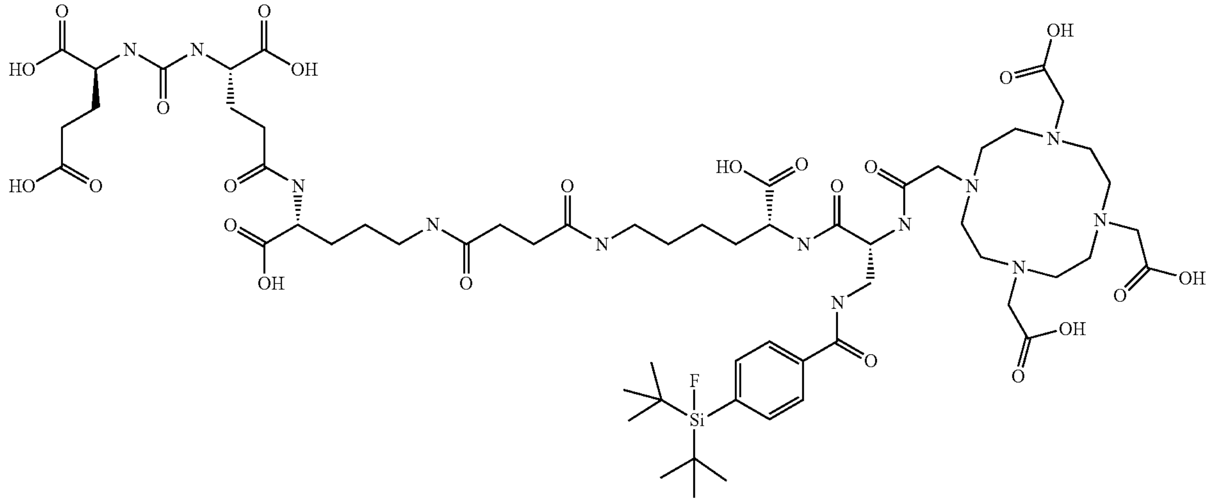
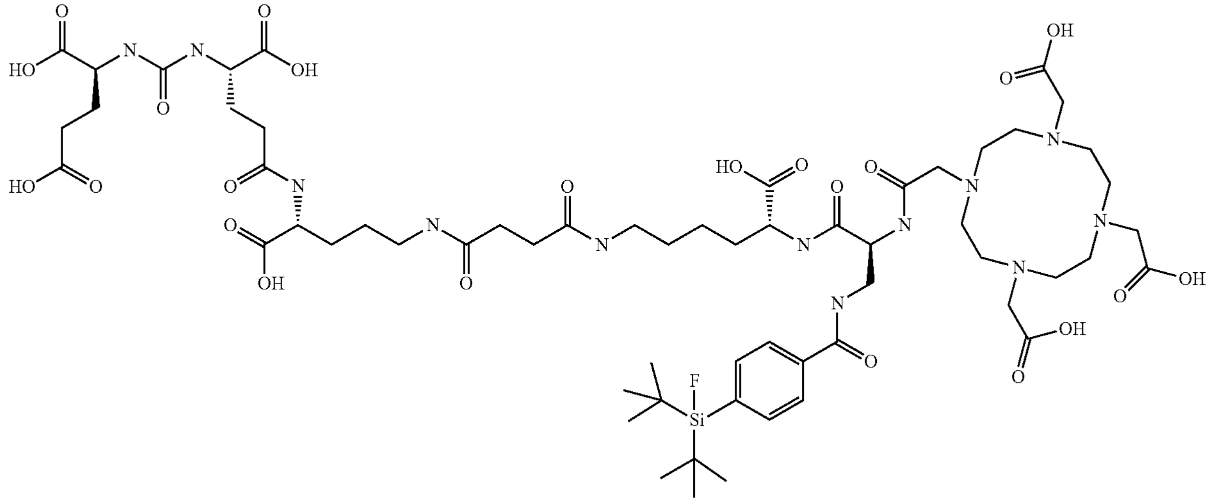

-continued
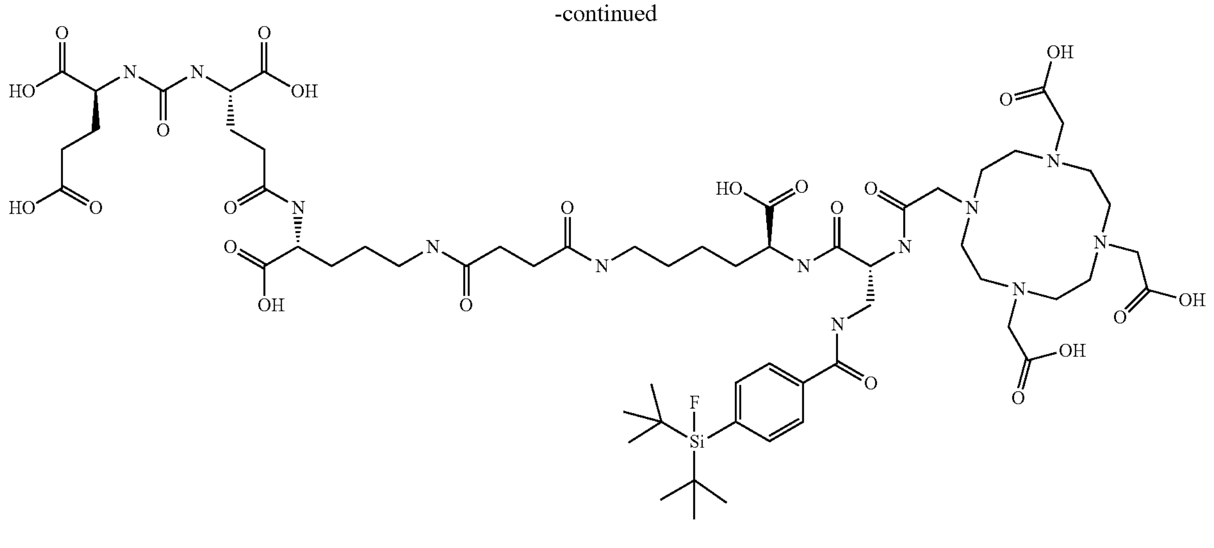
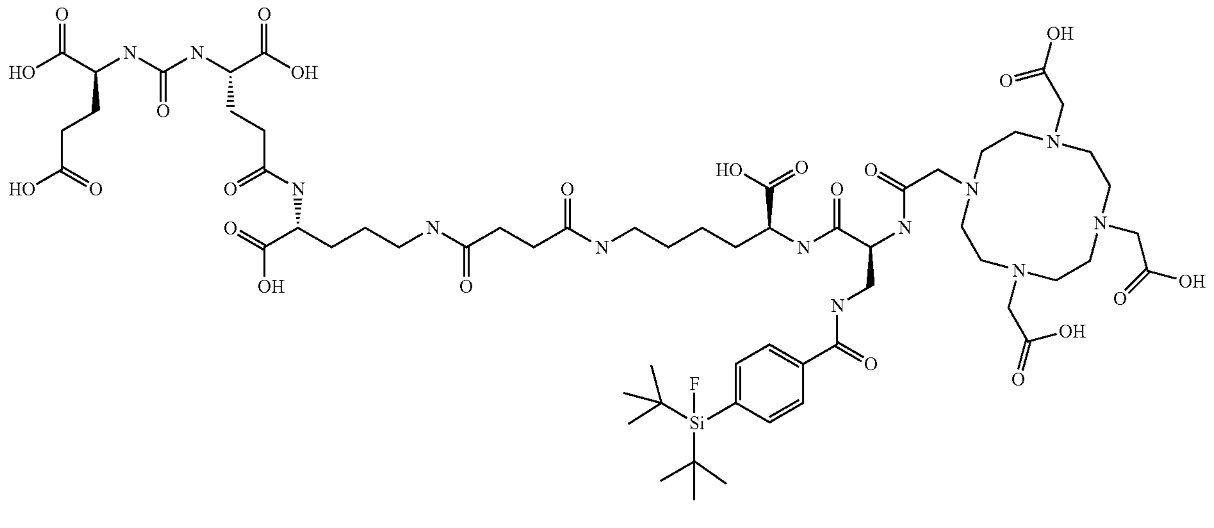
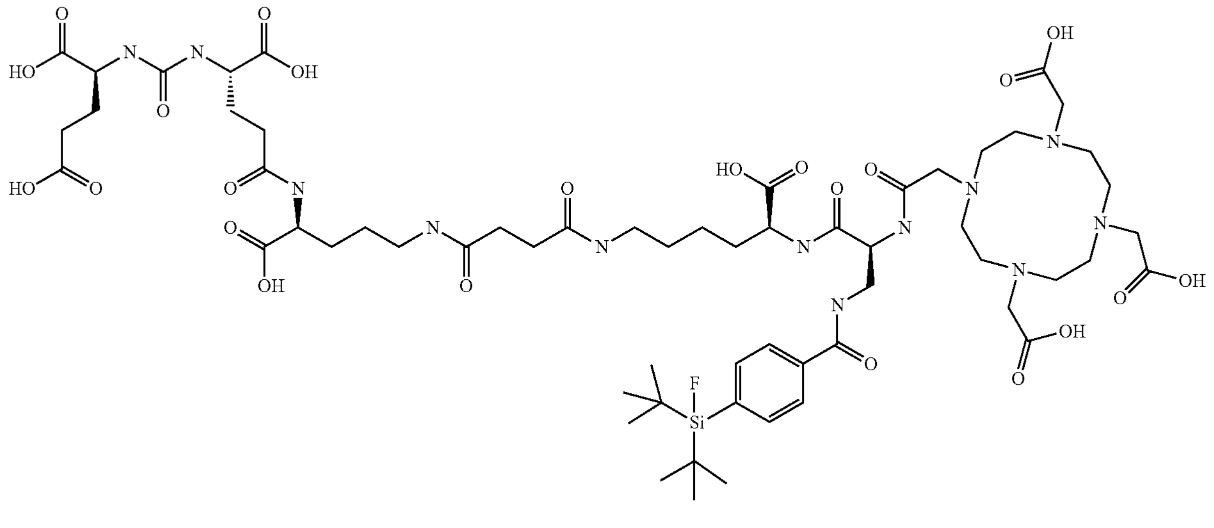

-continued
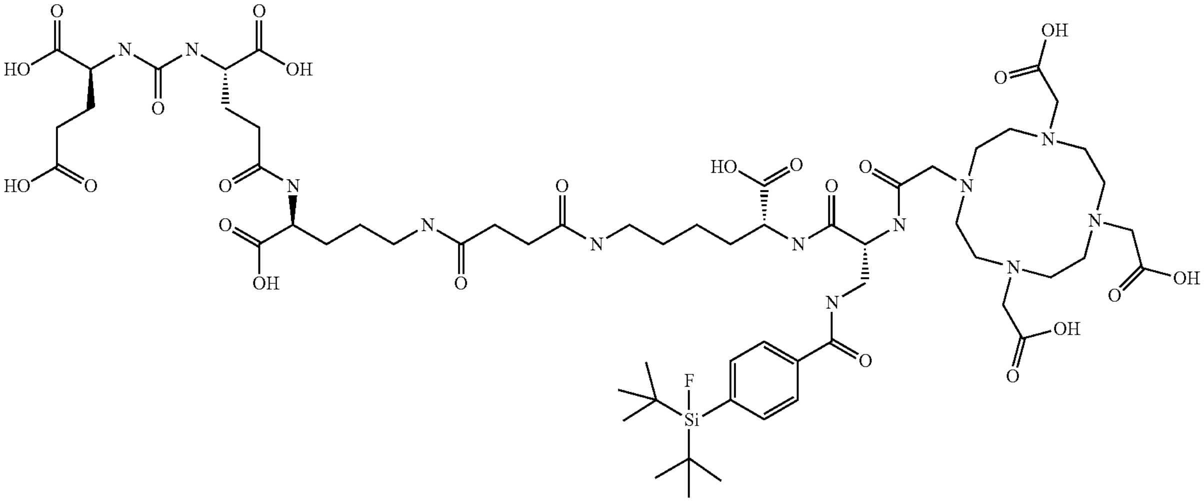
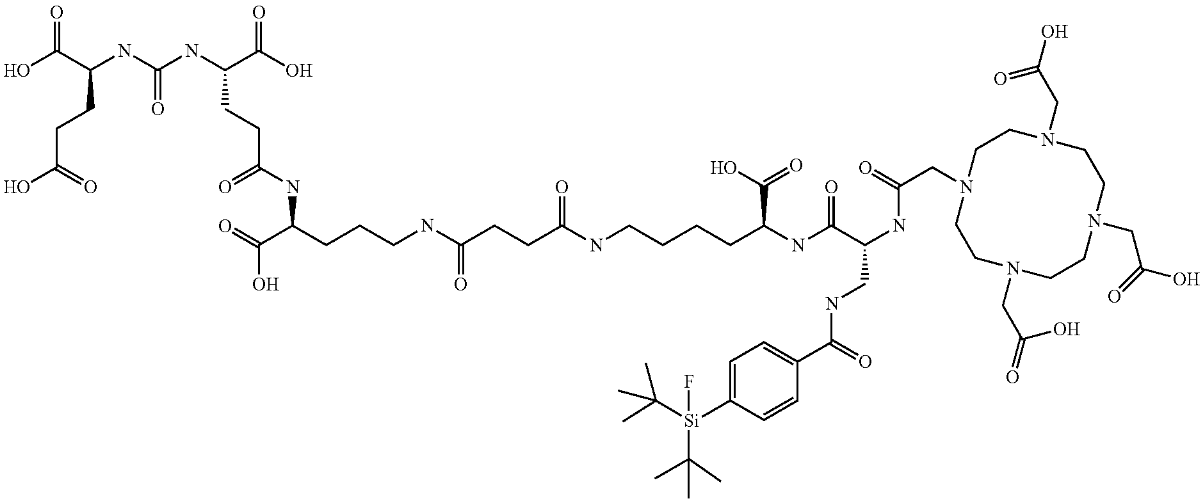
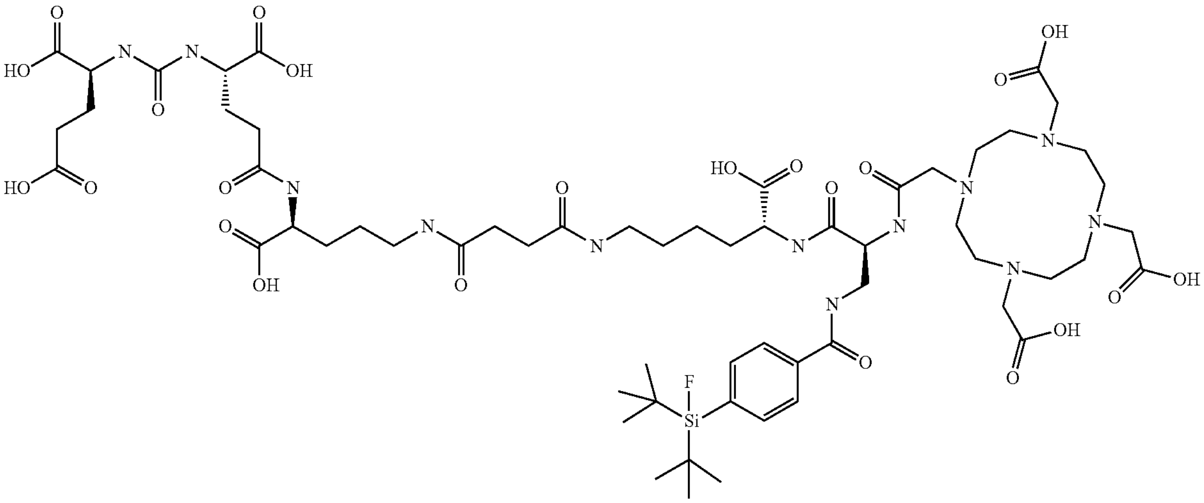

-continued
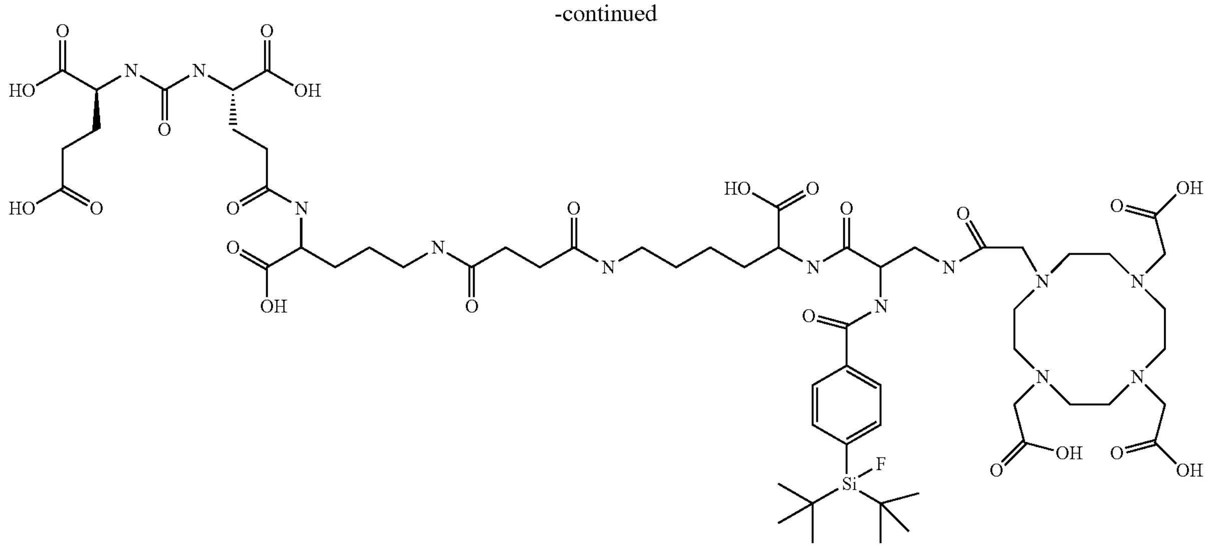
PSMA-SIFA 11
and isomers thereof:
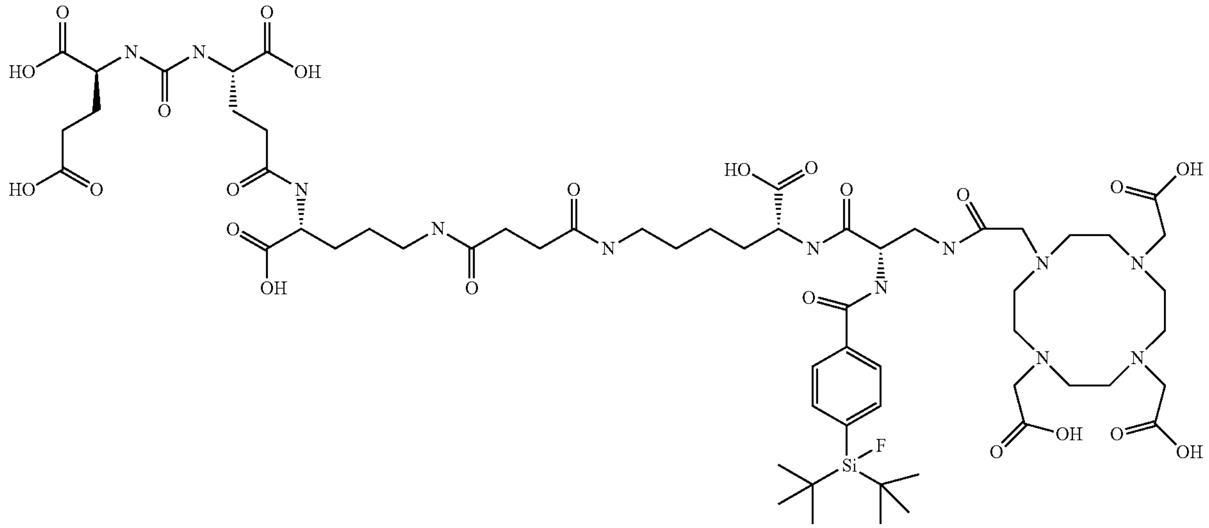
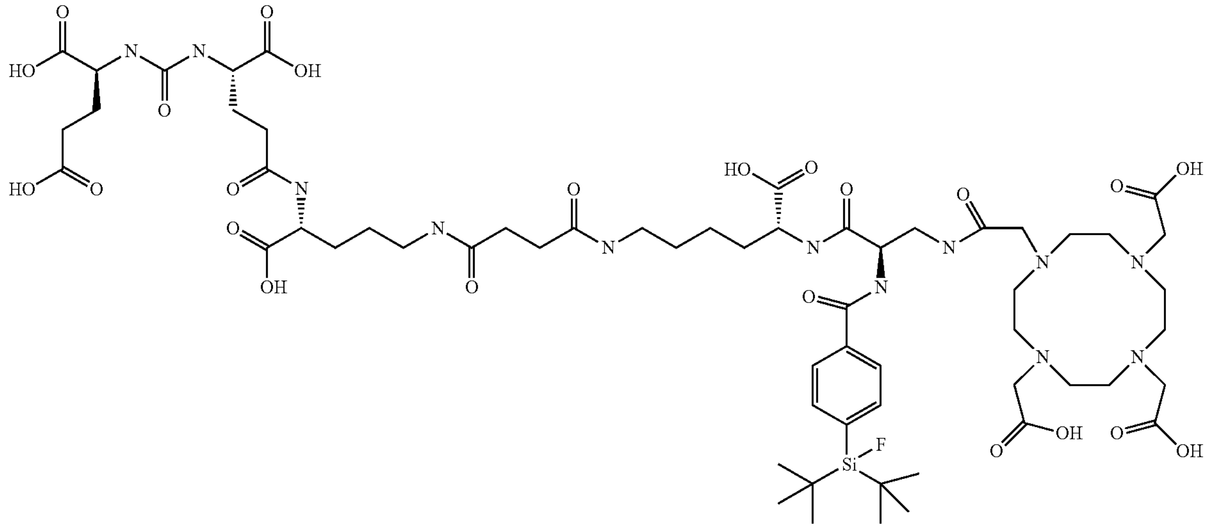

-continued
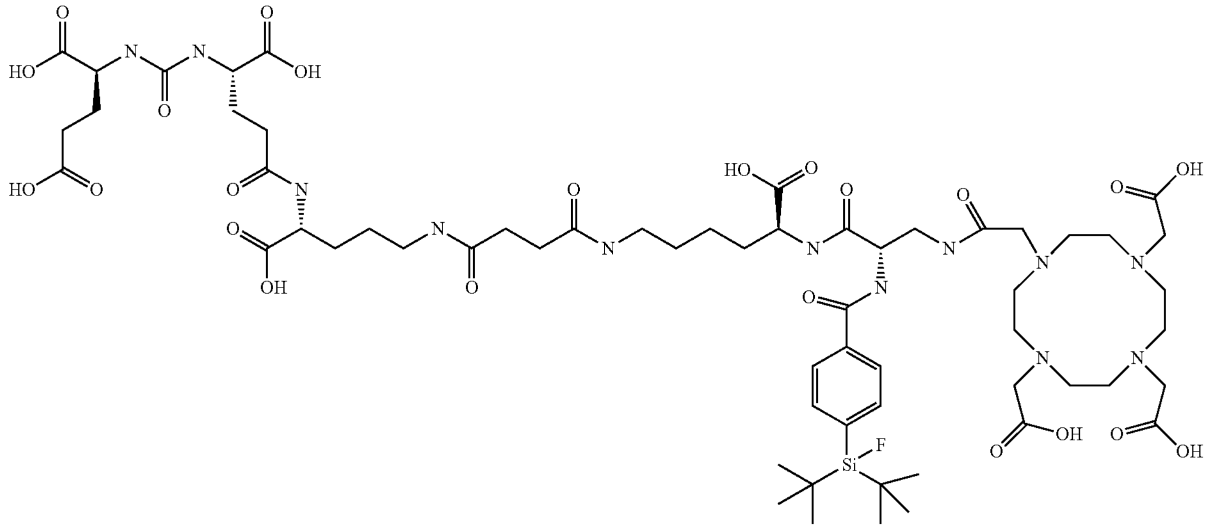
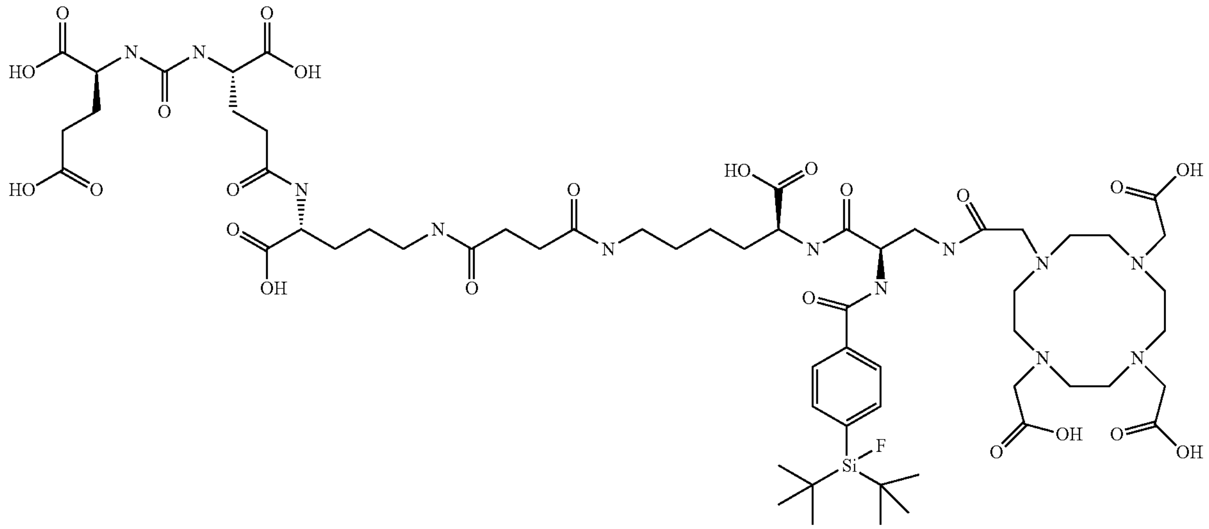
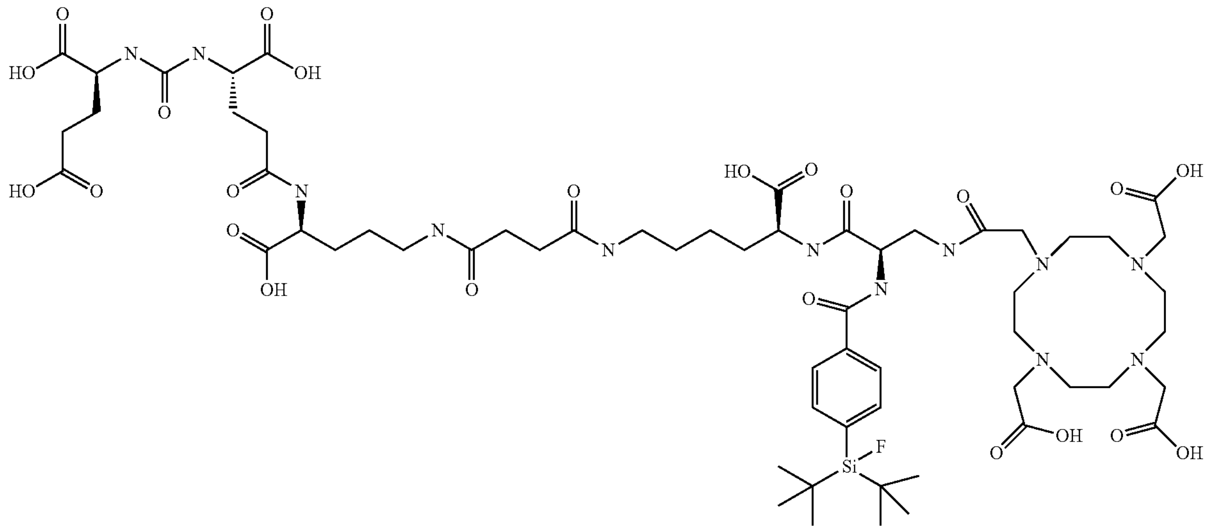

-continued
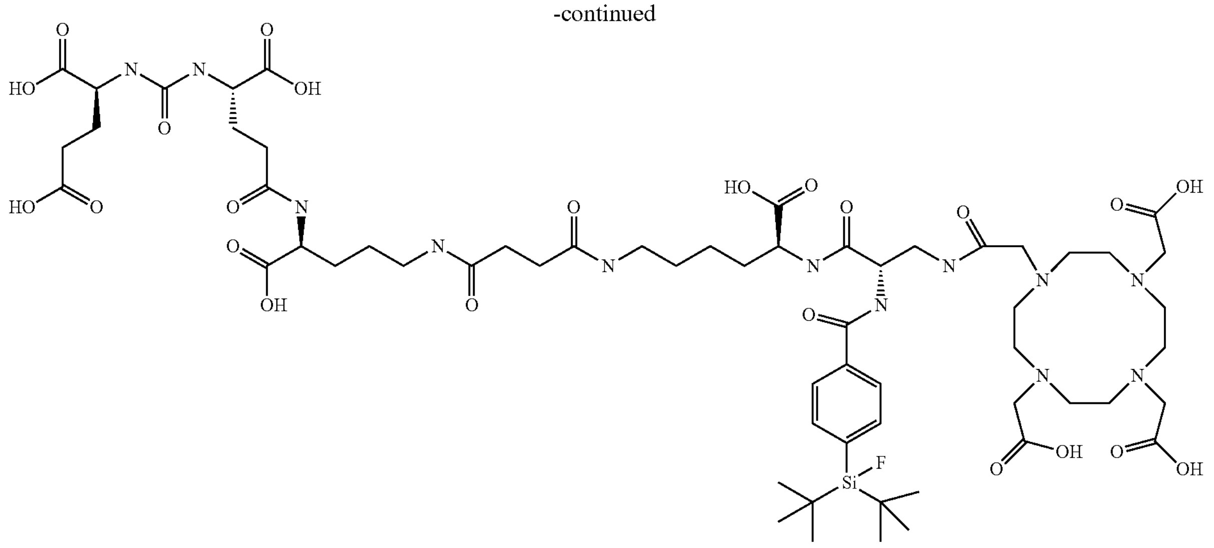
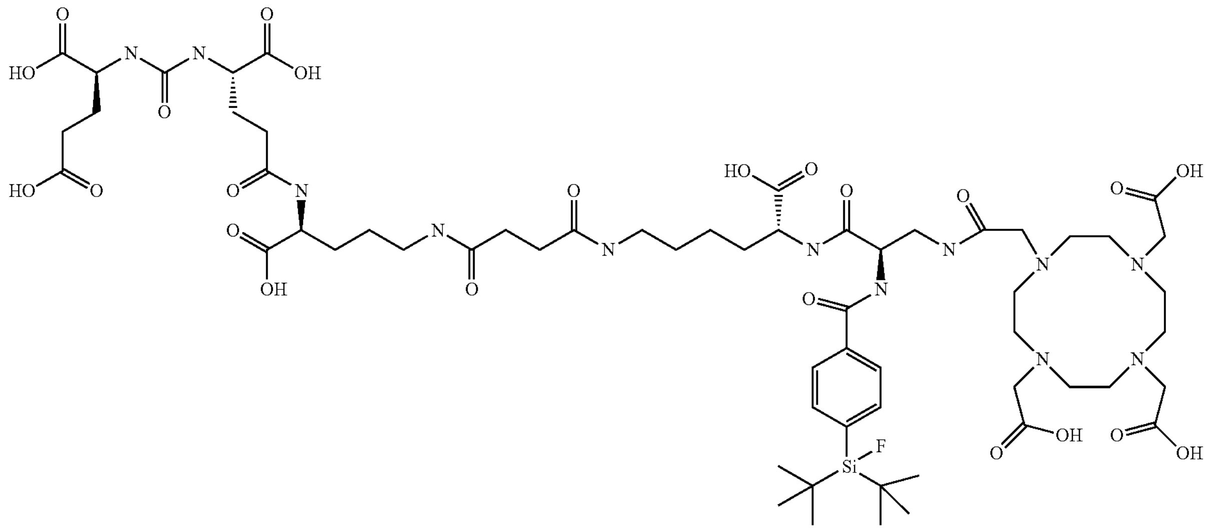
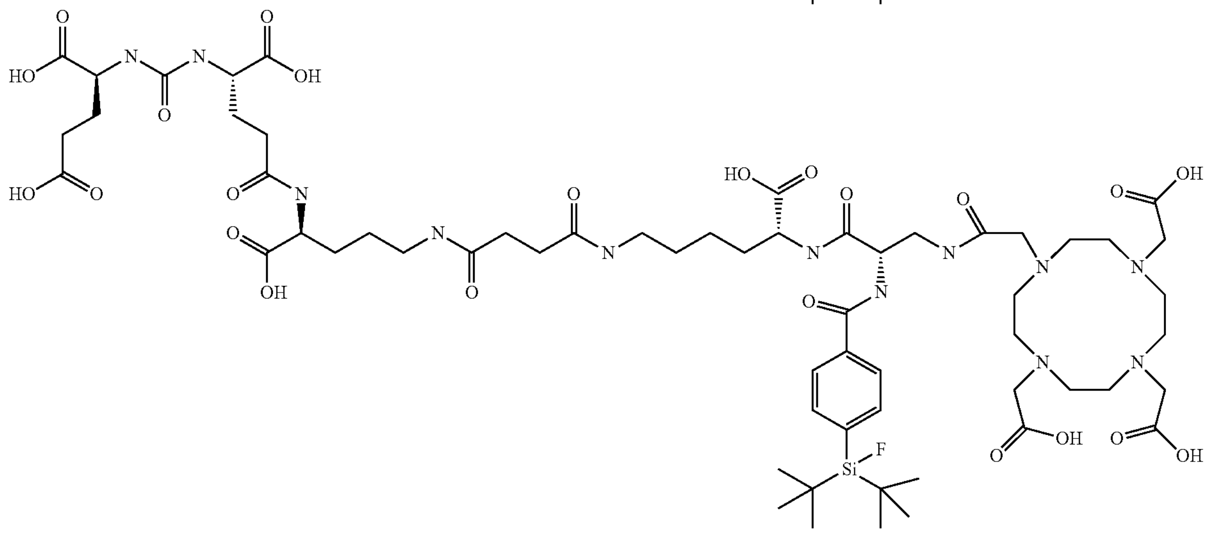
Preferred labelling schemes for these most preferred compounds are as defined herein above.
In a further aspect, the present invention provides a pharmaceutical composition comprising or consisting of one or more conjugates or compounds of the invention as disclosed herein above.

In a further aspect, the present invention provides a diagnostic composition comprising or consisting of one or more conjugates or compounds of the invention as disclosed herein above.

In a further aspect, the present invention provides a therapeutic composition comprising or consisting of one or more conjugates or compounds of the invention as disclosed herein above.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 0, 1 ng and 10 mg/kg body weight per dose; however, doses below or above this exemplary range are envisioned, especially considering the aforementioned factors.

In a further aspect, the present invention provides one or more compounds of the invention as disclosed herein above for use in medicine.

Preferred uses in medicine are in nuclear medicine such as nuclear diagnostic imaging, also named nuclear molecular imaging, and/or targeted radiotherapy of diseases associated with an overexpression, preferably of PSMA on the diseased tissue.

In a further aspect, the present invention provides a compound of the invention as defined herein above for use in a method of diagnosing and/or staging cancer, preferably prostate cancer. Prostate cancer is not the only cancer to express PSMA. Nonprostate cancers to demonstrate PSMA expression include breast, lung, colorectal, and renal cell carcinoma. Thus any compound described herein having a PSMA binding moiety can be used in the diagnosis, imaging or treatment of a cancer having PSMA expression.

Preferred indications are the detection or staging of cancer, such as, but not limited high grade gliomas, lung cancer and especially prostate cancer and metastasized prostate cancer, the detection of metastatic disease in patients with primary prostate cancer of intermediate-risk to high-risk, and the detection of metastatic sites, even at low serum PSA values in patients with biochemically recurrent prostate cancer. Another preferred indication is the imaging and visualization of neoangiogensis.

In terms of medical indications to be subjected to therapy, especially radiotherapy, cancer is a preferred indication. Prostate cancer is a particularly preferred indication.

In a further aspect, the present invention provides a conjugate or compound of the invention as defined herein above for use in a method of diagnosing and/or staging cancer, preferably prostate cancer.

The present disclosure furthermore relates to the following items.

1. A ligand-SIFA-chelator conjugate, comprising, within in a single molecule:
   (a) one or more ligands which are capable of binding to a disease-relevant target molecule,
   (b) a silicon-fluoride acceptor (SIFA) moiety which comprises a covalent bond between a silicon and a fluorine atom and which can be labeled with $^{18}F$ by isotopic exchange of $^{19}F$ by $^{18}F$ or which is labeled with $^{18}F$, and
   (c) one or more chelating groups, optionally containing a chelated nonradioactive or radioactive cation.
2. The conjugate in accordance with item 1, wherein the silicon-fluoride acceptor (SIFA) moiety has the structure represented by formula (I):

(I)

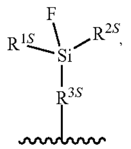

wherein $R^{1S}$ and $R^{2S}$ are independently a linear or branched C3 to C10 alkyl group, preferably $R^{1S}$ and $R^{2S}$ are selected from isopropyl and tert-butyl, and are more preferably $R^{1S}$ and $R^{2S}$ are tert-butyl;

$R^{3S}$ is a C1 to C20 hydrocarbon group which may comprise one or more aromatic and one or more aliphatic units and/or up to 3 heteroatoms selected from O and S, preferably $R^{3S}$ is a C6 to C10 hydrocarbon group which comprises an aromatic ring and which may comprise one or more aliphatic units; more preferably $R^{3S}$ is a phenyl ring, and most preferably, $R^{3S}$ is a phenyl ring wherein the Si-containing substituent and the bond marked by ∿∿∿ are in a para-position, and wherein the SIFA moiety is attached to the remainder of the conjugate via the bond marked by ∿∿∿ .

3. The conjugate in accordance with item 2, wherein the silicon-fluoride acceptor (SIFA) moiety has the structure represented by formula (Ia):

(Ia)

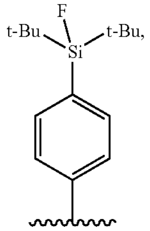

wherein t-Bu indicates a tert-butyl group.

4. The conjugate in accordance with any of items 1 to 3, wherein the chelating group comprises at least one of
   (i) a macrocyclic ring structure with 8 to 20 ring atoms of which 2 or more, preferably 3 or more, are selected from oxygen atoms and nitrogen atoms; and
   (ii) an acyclic, open chain chelating structure with 8 to 20 main chain atoms of which 2 or more, preferably 3 or more are heteroatoms selected from oxygen atoms and nitrogen atoms.
5. The conjugate in accordance with any of items 1 to 3, wherein the chelating group is a residue of a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecan (DO2A) 1,4,7,10-tetracyclododecan-N,N',N",N"'-tetraacetic acid (DOTA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N",N"'-tetraacetic acid (TRITA), and triethylenetetraaminehexaacetic acid (TTHA); which residue is provided by covalently binding a carboxyl group contained in the chelating agent to the remainder of the conjugate via an ester or an amide bond, preferably via an amide bond.
6. The conjugate in accordance with item 5, wherein the chelating agent is selected from DOTA and DOTAGA.
7. The conjugate in accordance with any of items 1 to 6, wherein the chelating group comprises a chelated cation, preferably a chelated radioactive cation selected from $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, <Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At., $^{212}$Bi, $^{213}$Bi, $^{223}$Ra, $^{225}$Ac, $^{227}$Th, a cationic molecule comprising $^{18}$F or a cation such as $^{18}$F-$[AlF]^{2+}$; more preferably the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.
8. The conjugate in accordance with any of items 1 to 8, wherein the ligand is capable of binding to PSMA.
9. The conjugate in accordance with any of items 1 to 8, wherein the ligand has the structure represented by formula (II):

(II)

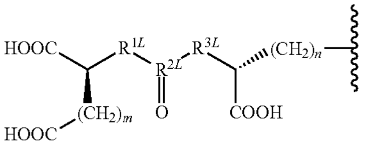

wherein:

m is an integer of 2 to 6, preferably 2 to 4, more preferably 2;

n is an integer of 2 to 6, preferably 2 to 4, more preferably 2 or 3;

$R^{1L}$ is $CH_2$, NH or O, preferably NH;

$R^{3L}$ is $CH_2$, NH or O, preferably NH;

$R^{2L}$ is C or P(OH), preferably C;

and wherein the ligand is attached to the remainder of the conjugate via the bond marked by ∿∿∿.

10. The conjugate in accordance with any of items 1 to 9, which is a compound of formula (III):

(III)

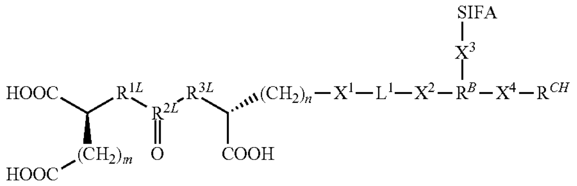

or a pharmaceutically acceptable salt thereof, wherein:

SIFA is a silicon-fluoride acceptor (SIFA) moiety which comprises a covalent bond between a silicon and a fluorine atom and which can be labeled with $^{18}$F by isotopic exchange between $^{19}$F and $^{18}$F or which is labeled with $^{18}$F; preferably SIFA is the SIFA moiety defined in claim 2;

m is an integer of 2 to 6, preferably 2 to 4, more preferably 2;

n is an integer of 2 to 6, preferably 2 to 4, more preferably 2 or 3;

$R^{1L}$ is $CH_2$, NH or O, preferably NH;

$R^{3L}$ is $CH_2$, NH or O, preferably NH;

$R^{2L}$ is C or P(OH), preferably C;

$X^1$ is selected from an amide bond, an ether bond, a thioether bond, an ester bond, a thioester bond, an urea bridge, and an amine bond, preferably an amide bond;

$X^2$ is selected from an amide bond, an ether bond, a thioether bond, an ester bond, a thioester bond, an urea bridge, and an amine bond, preferably an amide bond;

$L^1$ is a divalent linking group with a structure selected from an oligoamide, an oligoether, an oligothioether, an oligoester, an oligothioester, an oligourea, an oligo(ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo ether-urea), an oligo(thioether-ester), an oligo(thioether-thioester), an oligo(thioether-urea), an oligo(ester-thioester), an oligo(ester-urea), and an oligo(thioester-urea); preferably with a structure selected from and oligoamide and an oligo(ester-amide);

$X^3$ is selected from an amide bond, an ester bond, an ether, an amine, and a linking group of the formula:

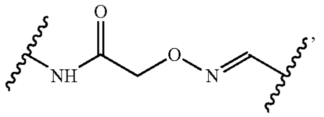 [SMILES: */C=N/OCC(=O)N*]

wherein the bond marked by ∿∿∿ at the NH group is bound to $R^B$ and the other bond marked by ∿∿∿ is bound to SIFA; preferably $X^3$ is an amide bond;

$R^B$ is a trivalent coupling group;

$X^4$ is selected from an amide bond, an ether bond, a thioether bond, an ester bond, a thioester bond, an urea bridge, an amine bond, and a linking group of the formula:

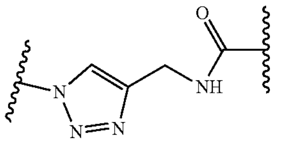 [SMILES: *C(=O)NCc1cn(*)nn1]

wherein the amide bond marked by ∿∿∿ is formed with the chelating group, and the other bond marked by ∿∿∿ is bound to $R^B$; preferably $X^4$ is an amide bond;

$R^{CH}$ is chelating group optionally containing a chelated radioactive or nonradioactive cation, preferably a radioactive or nonradioactive metal cation, preferably a chelating group as defined in item 4, more preferably a chelating group as defined in item 5, and most preferably a chelating group as defined in item 6.

11. The conjugate in accordance with item 10, wherein $L^1$ comprises a total of 1 to 5, more preferably a total of 1 to 3, and most preferably a total of 1 or 2 amide and/or ester bonds, preferably amide bonds, within its backbone.

12. The conjugate in accordance with item 10, wherein $-X^1-L^1-X^2-$represents one of the following structures (L-1) and (L-2):

$$-NH-C(O)-R^6-C(O)-NH-R^7-NH-C(O)- \quad (L\text{-}1)$$

$$-C(O)-NH-R^8-NH-C(O)-R^9-C(O)-NH-R^{10}-NH-C(O)- \quad (L\text{-}2)$$

wherein $R^6$ to $R^{10}$ are independently selected from C2 to C10 alkylene, preferably linear C2 to C10 alkylene, which alkylene groups may each be substituted by one or more substitutents independently selected from —OH, $-OCH_3$, —COOH, $-COOCH_3$, $-NH_2$, and $-NHC(NH)NH_2$.

13. The conjugate in accordance with item 12, wherein the total number of carbon atoms in $R^6$ and $R^7$ or $R^8$ to $R^{10}$, respectively, is 8 to 20, more preferably 8 to 14, without carbon atoms contained in optional substituents.

14. The conjugate in accordance with 10, wherein $-X^1-L^1-X^2-$ represents one of the following structures (L-3) and (L-4):

$$-NH-C(O)-R^{11}-C(O)-NH-R^{12}-CH(COOH)-NH-C(O)- \quad (L\text{-}3)$$

$$-C(O)-NH-CH(COOH)-R^{13}-NH-C(O)-R^{14}-C(O)-NH-R^{15}-CH(COOH)-NH-C(O)- \quad (L\text{-}4)$$

wherein $R^{11}$ to $R^{15}$ are independently selected from C2 to C8 alkylene, preferably linear C2 to C8 alkylene.

15. The conjugate in accordance with item 14, wherein the total number of carbon atoms in $R^{11}$ and $R^{12}$ or $R^{13}$ to $R^{15}$, respectively, is 8 to 18, more preferably 8 to 12, yet more preferably 9 or 10.

16. The conjugate in accordance with any of items 10 to 15, wherein Re has the structure represented by formula (IV):

(IV)

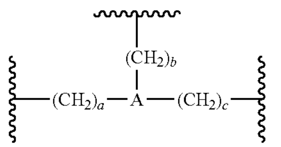

wherein:

A is selected from N, $CR^{16}$, wherein $R^{16}$ is H or C1-C6 alkyl, and a 5 to 7 membered carbocyclic or heterocyclic group; preferably A is selected from N and CH, and more preferably A is CH;

the bond marked by ∿∿∿ at $(CH_2)_a$ is formed with $X^2$, and a is an integer of 0 to 4, preferably 0 or 1, and most preferably 0;

the bond marked by ∿∿∿ at $(CH_2)_b$ is formed with $X^3$, and b is an integer of 0 to 4, preferably of 0 to 2, and more preferably 0 or 1; and the bond marked by ∿∿∿ at $(CH_2)_c$ is formed with $X^4$, and c is an integer of 0 to 4, preferably of 0 to 2, and more preferably 0 or 1.

17. The conjugate in accordance with any of items 10 to 16, which is a compound of formula (IIIa):

(IIIa)

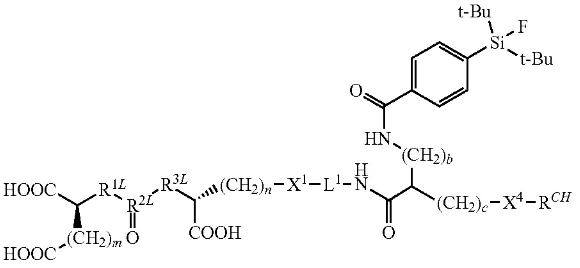

or a pharmaceutically acceptable salt thereof, wherein m, n, $R^{1L}$, $R^{2L}$, $R^{3L}$, $X^1$, $L^1$, b, c, $X^4$ and $R^{CH}$ are as defined in items 10 to 16.

18. The conjugate in accordance with item 17, wherein b+c≥1.

19. The conjugate in accordance with any of items 17 to 18, wherein b+c≤3.

20. The conjugate in accordance with any of items 17 to 19, wherein b is 1 and c is 0.

21. The conjugate in accordance with any of items 10 to 20, wherein $-X^4-R^{CH}$ represents a residue of a chelating agent selected from DOTA and DOTAGA bound with one of its carboxylic groups via an amide bond to the remainder of the conjugate.

22. The conjugate in accordance with any of items 10 to 20, which is a compound of formula (IIIb):

(IIIb)

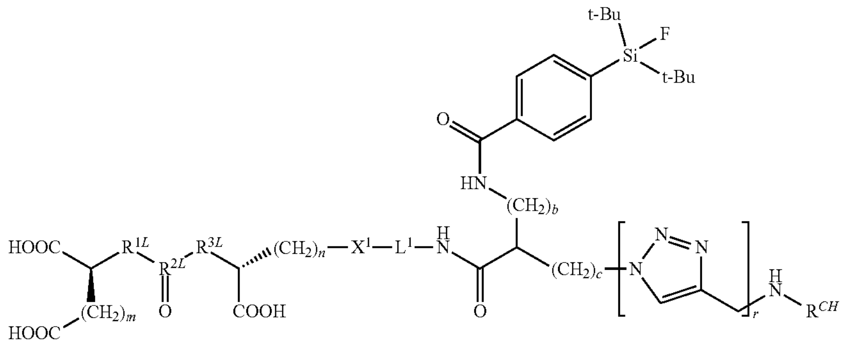

or a pharmaceutically acceptable salt thereof, wherein m, n, $R^{1L}$, $R^{2L}$, $R^{3L}$, $X^1$, $L^1$, b, c, $X^4$ and $R^{CH}$ are as defined in items 10 to 20; and r is 0 or 1.

23. The conjugate in accordance with item 22, wherein —N(H)—$R^{CH}$ represents a residue of a chelating agent selected from DOTA and DOTAGA bound with one of its carboxylic groups via an amide bond to the remainder of the conjugate.

The Figures illustrate:

FIG. 1: Exemplary correlation of the determination of the binding of nine reference substances to Human Serum Albumin (OriginPro 2016G)

Figure 2:
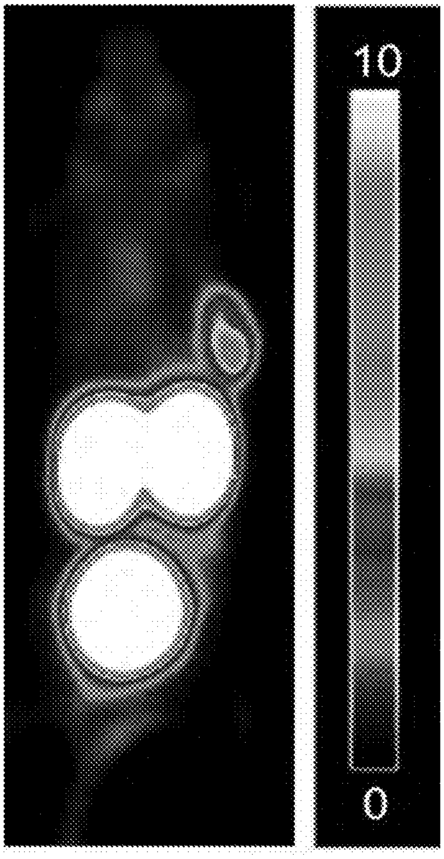

FIG. 2: Representative PET-image (maximum intensity projection, dorsal frame) of $^{68}$Ga-$^{nat}$F-5 in a LNCaP tumor-bearing SCID mouse (1 h p.i., 15 min acquisition time) and ROI quantification of selected organs. Data are expressed as mean±SD (n=4). % ID/mL=% injected dose per mL. Tumor position is indicated by an arrow.

Figure 3:
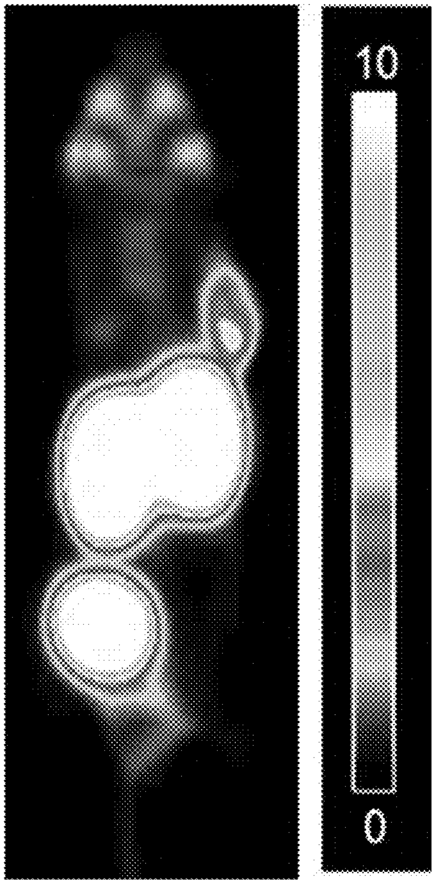

FIG. 3: Representative PET-image (maximum intensity projection, dorsal frame) of $^{68}$Ga-$^{nat}$F-6 in a LNCaP tumor-bearing SCID mouse (1 h p.i., 15 min acquisition time) and ROI quantification of selected organs. Data are expressed as mean±SD (n=4). % ID/mL=% injected dose per mL. Tumor position is indicated by an arrow.

Figure 4:
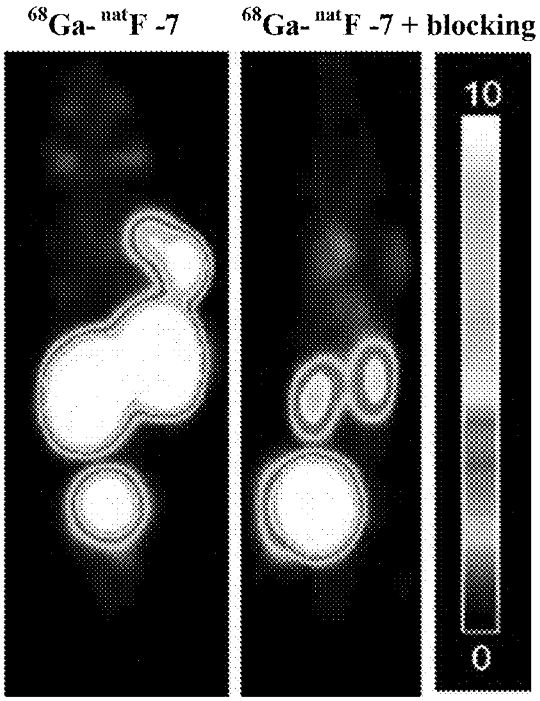

FIG. 4: Representative PET-images (maximum intensity projection, dorsal frame) of $^{68}$Ga-$^{nat}$F-7 and $^{68}$Ga-$^{nat}$F-7 co-injected with PMPA (8 mg/kg) in LNCaP tumor-bearing SCID mice (1 h p.i., 15 min acquisition time) and ROI quantification of selected organs of the PET scan without blocking. Data are expressed as mean±SD (n=2). % ID/mL=% injected dose per mL. Tumor positions are indicated by arrows.

Figure 5:
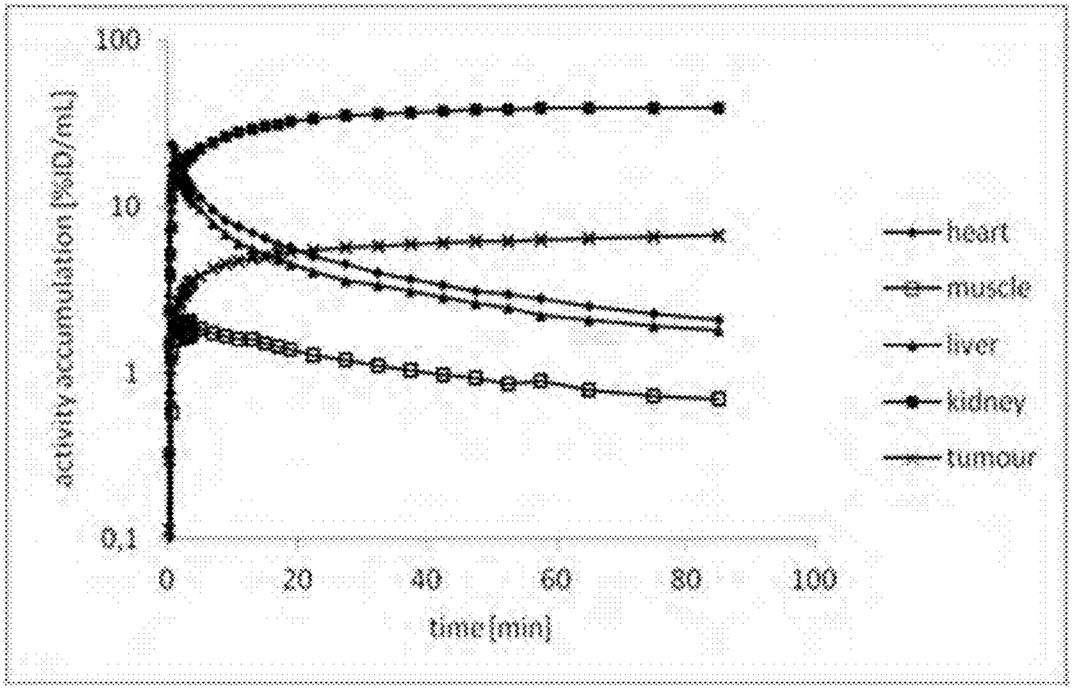

FIG. 5: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{68}$Ga-$^{nat}$F-7 in a LNCaP tumor-bearing SCID mouse.

Figure 6:
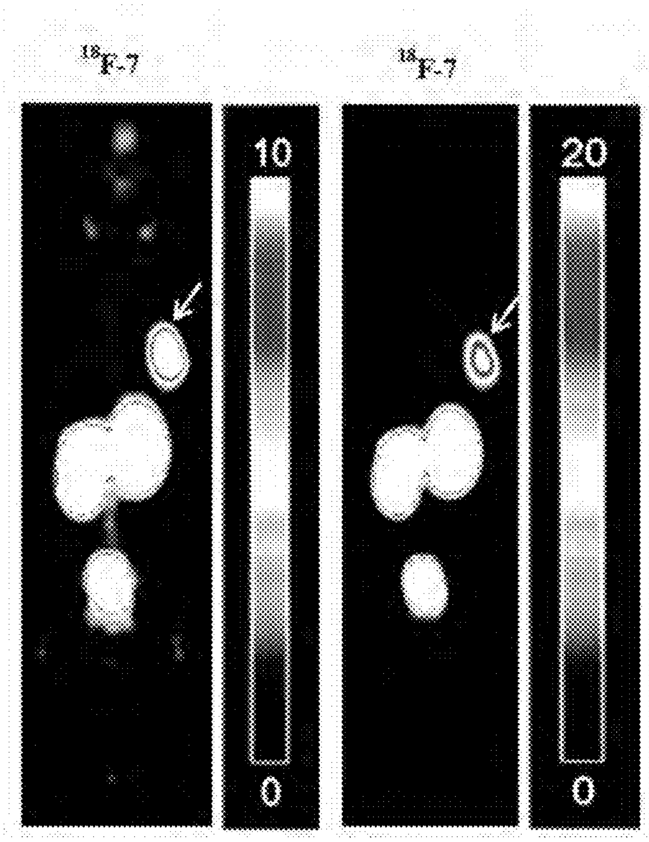

FIG. 6: Representative PET-images (maximum intensity projection, dorsal frame) of $^{18}$F-7 (with free chelate) in LNCaP tumor-bearing SCID mice (1 h p.i., 15 min acquisition time) and ROI quantification of selected organs of the PET scan without blocking. Data are expressed as mean±SD (n=3). % ID/mL=% injected dose per mL. Tumor positions are indicated by arrows.

Figure 7:
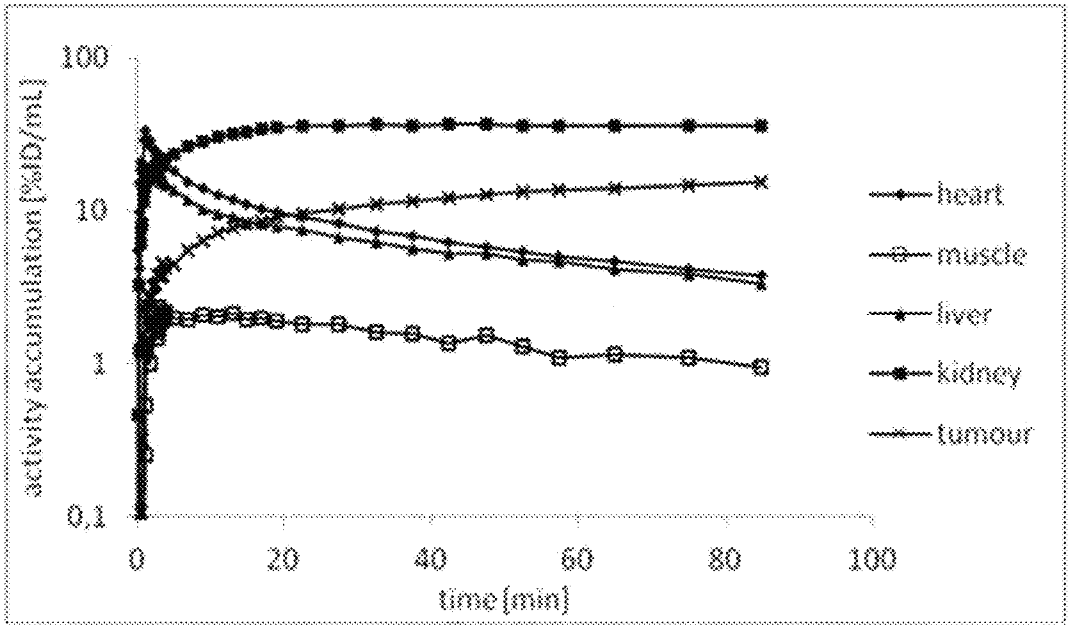

FIG. 7: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{18}$F-7 (with free chelate) in a LNCaP tumor-bearing SCID mouse.

Figure 8:
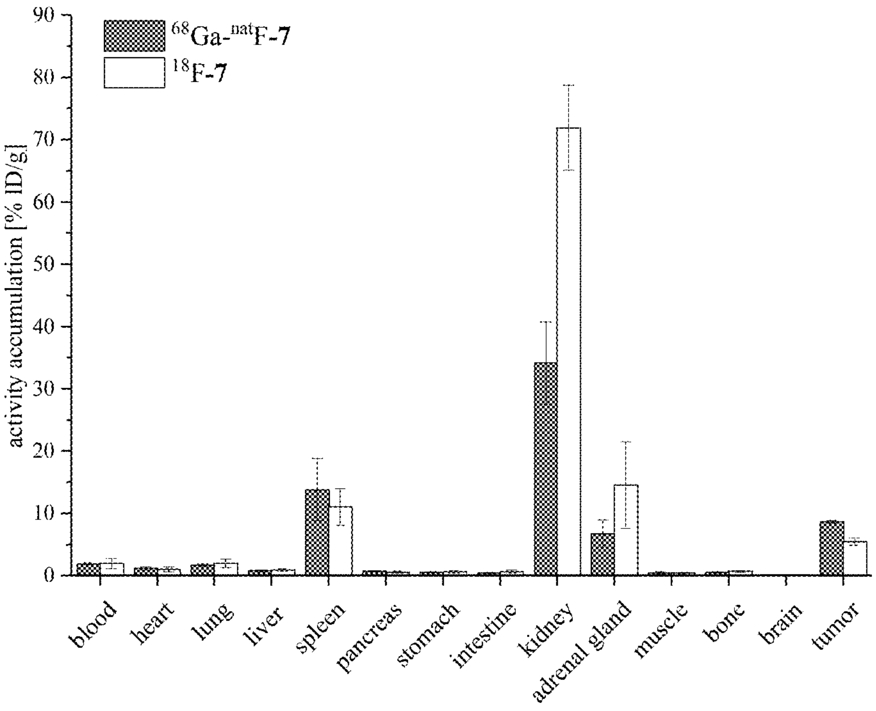

FIG. 8: Biodistribution (in % ID/g) of $^{68}$Ga-$^{nat}$F-7 (grey bars) and $^{18}$F-7 (with free chelate) (white bars) at 1 hour p.i. in LNCaP tumor-bearing SCID mice. Data are expressed as mean±SD (n=3).

Figure 9:
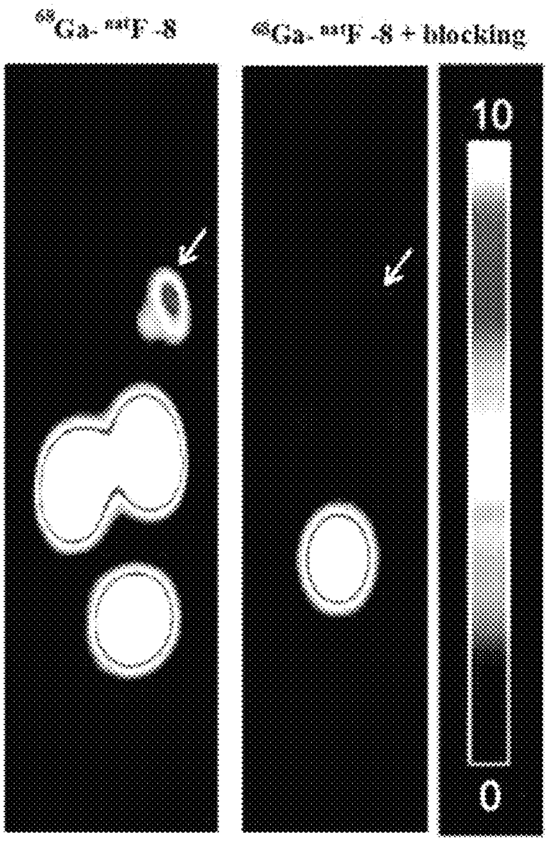

FIG. 9: Representative PET-images (maximum intensity projection, dorsal frame) of $^{68}$Ga-$^{nat}$F-8 and $^{68}$Ga-$^{nat}$F-8 co-injected with PMPA (8 mg/kg) in LNCaP tumor-bearing SCID mice (1 h p.i., 15 min acquisition time) and ROI quantification of selected organs of the PET scan without blocking. Data are expressed as mean±SD (n=2). % ID/mL=% injected dose per mL. Tumor positions are indicated by arrows.

Figure 10:
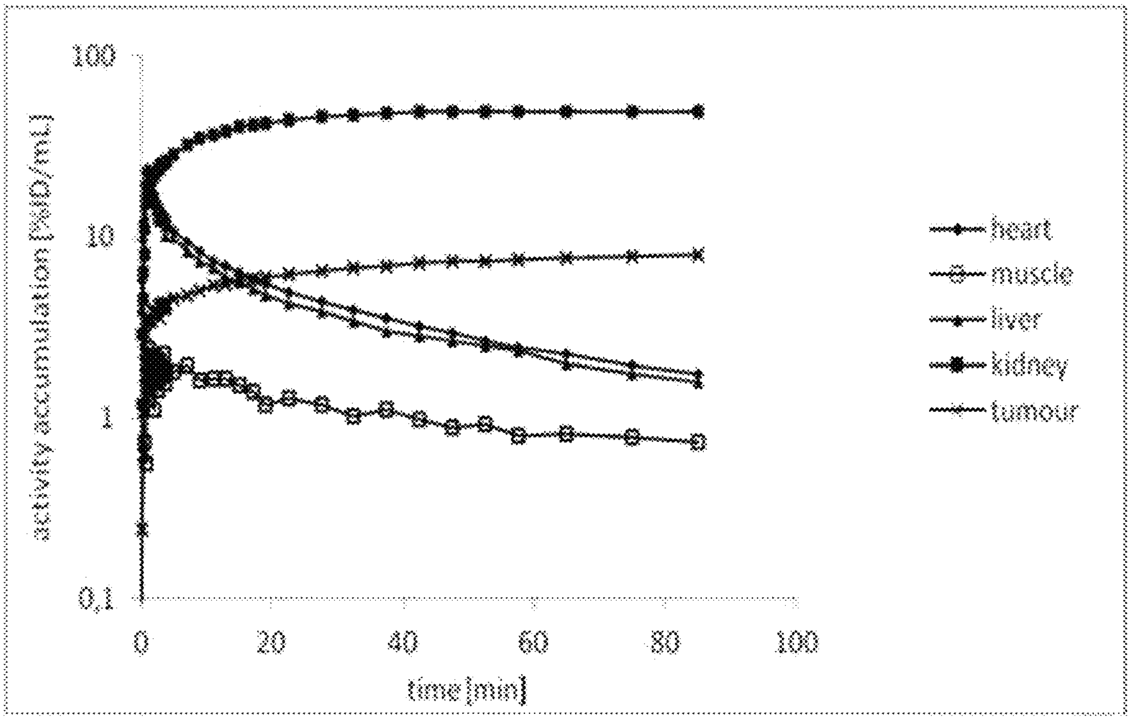

FIG. 10: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{68}$Ga-$^{nat}$F-8 in a LNCaP tumor-bearing SCID mouse.

Figure 11:
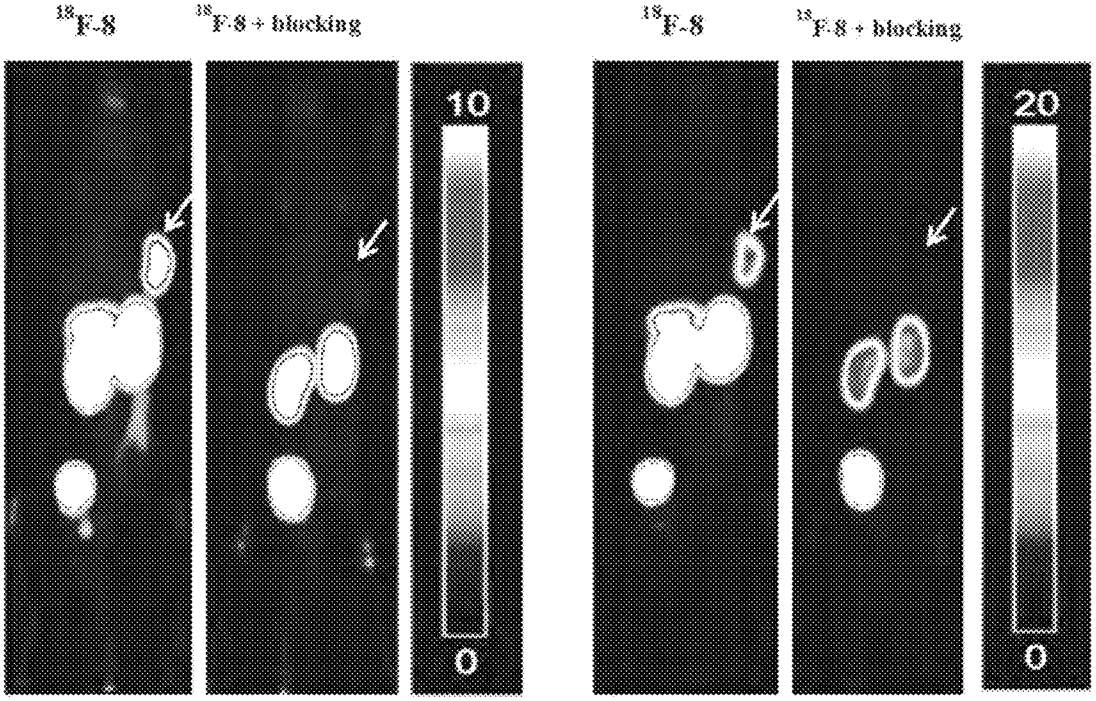

FIG. 11: Representative PET-images (maximum intensity projection, dorsal frame) of $^{18}$F-8 (free chelate) and $^{18}$F-8 (free chelate) co-injected with PMPA (8 mg/kg) in LNCaP tumor-bearing SCID mice (1 h p.i., 15 min acquisition time) and ROI quantification of selected organs of the PET scan without blocking. Data are expressed as mean±SD (n=3). % ID/mL=% injected dose per mL. Tumor positions are indicated by arrows. Note the different scaling (0-10 left; 0-20 right)

Figure 12:
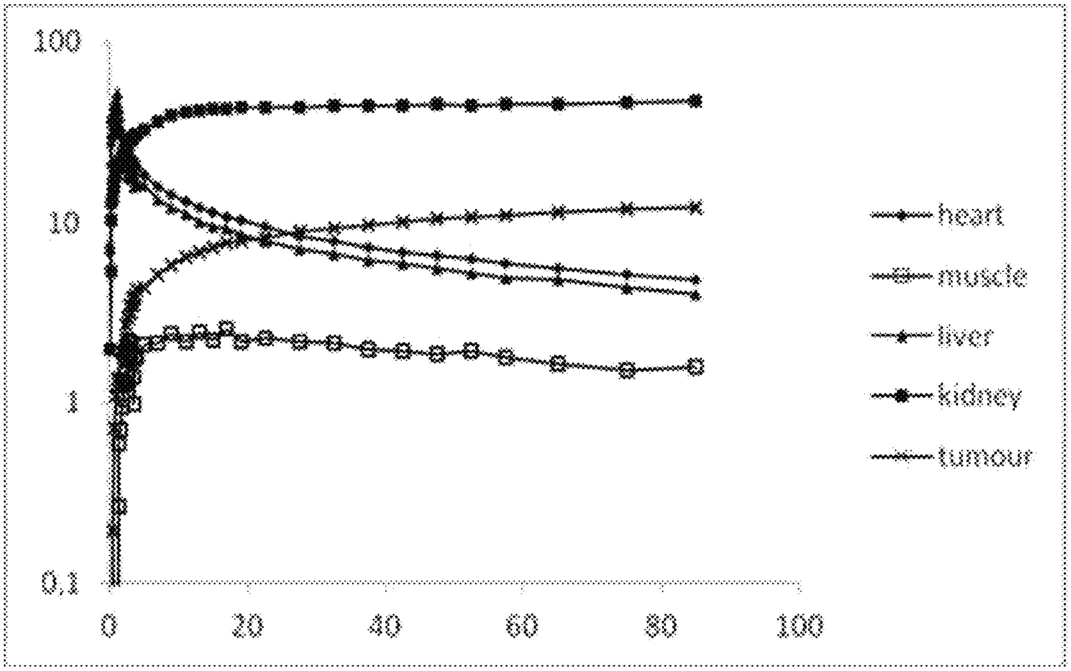

FIG. 12: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{18}$F-8 in a LNCaP tumor-bearing SCID mouse.

Figure 13:
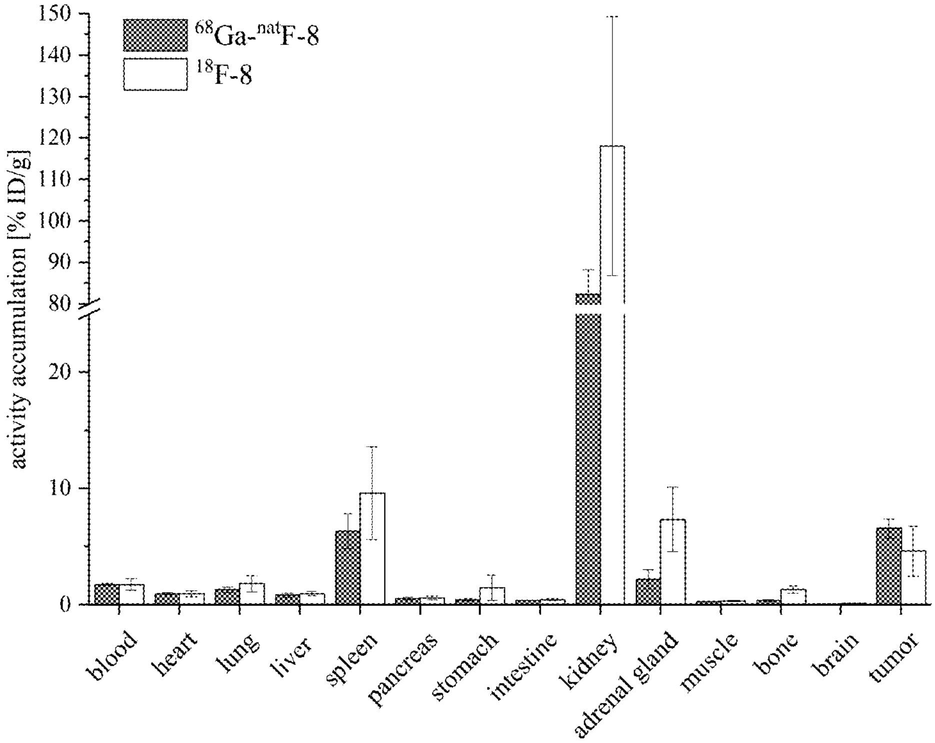

FIG. 13: Biodistribution (in % ID/g) of $^{68}$Ga-$^{nat}$F-8 (free chelate), (grey bars) and $^{18}$F-8 (white bars) at 1 hour p.i. in LNCaP tumor-bearing SCID mice. Data are expressed as mean±SD (n=3).

Figure 14:
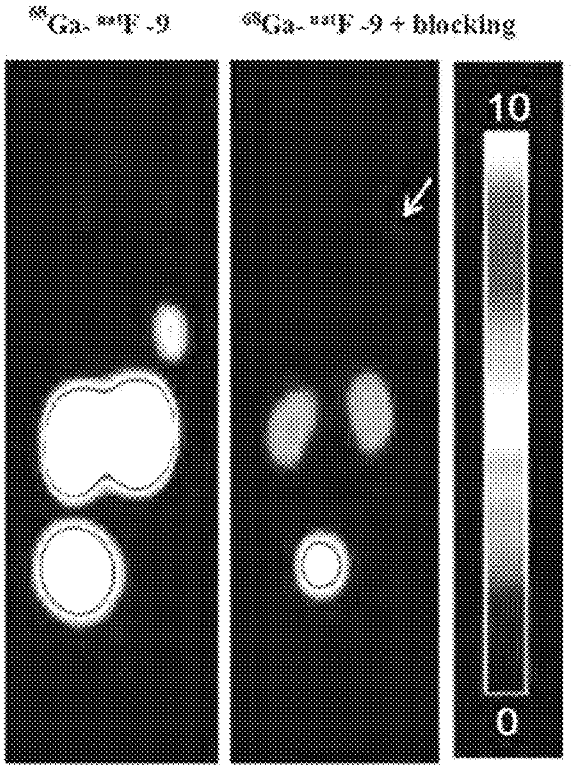

FIG. 14: Representative PET-images (maximum intensity projection, dorsal frame) of $^{68}$Ga-$^{nat}$F-9 (free chelate) and $^{68}$Ga-$^{nat}$F-9 (free chelate) co-injected with PMPA (8 mg/kg) in LNCaP tumor-bearing SCID mice (1 h p.i., 15 min acquisition time) and ROI quantification of selected organs of the PET scan without blocking. Data are expressed as mean±SD (n=3). % ID/mL=% injected dose per mL. Tumor positions are indicated by arrows.

Figure 15:
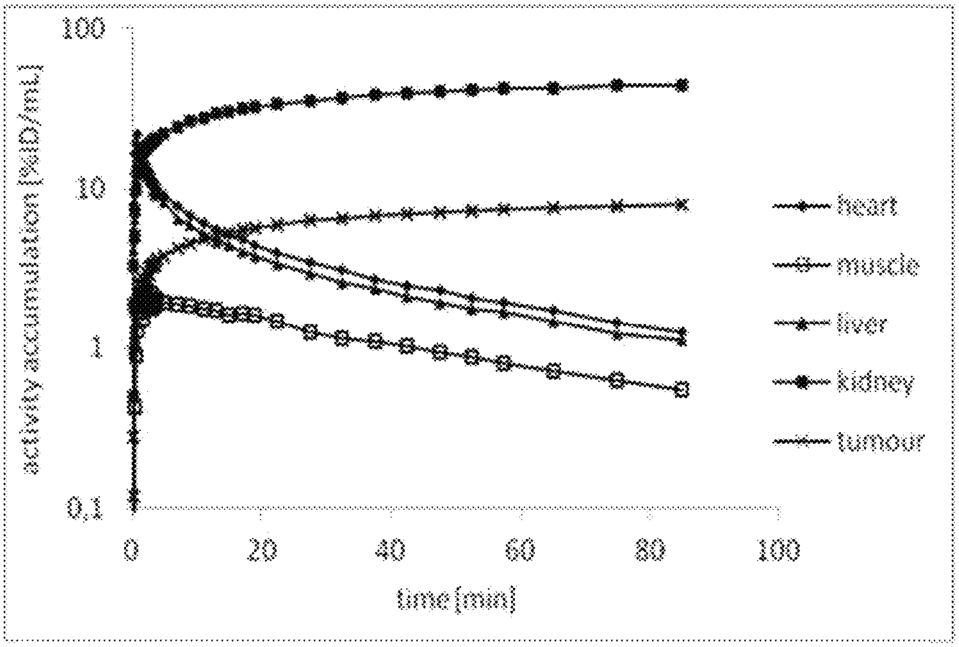

FIG. 15: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{68}$Ga-$^{nat}$F-9 in a LNCaP tumor-bearing SCID mouse.

Figure 16:
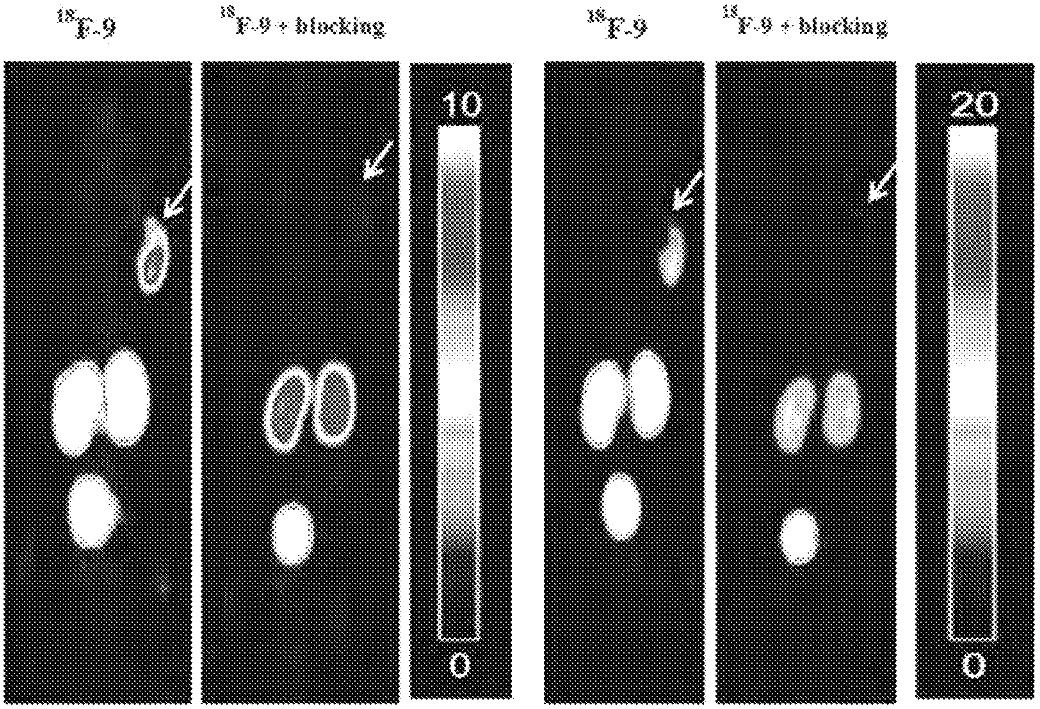

FIG. 16: Representative PET-images (maximum intensity projection, dorsal frame) of $^{18}$F-9 (free chelate) and $^{18}$F-9 (free chelate) co-injected with PMPA (8 mg/kg) in LNCaP tumor-bearing SCID mice (1 h p.i., 15 min acquisition time) and ROI quantification of selected organs of the PET scan without blocking. Data are expressed as mean±SD (n=4). % ID/mL=% injected dose per mL. Tumor positions are indicated by arrows.

Figure 17:
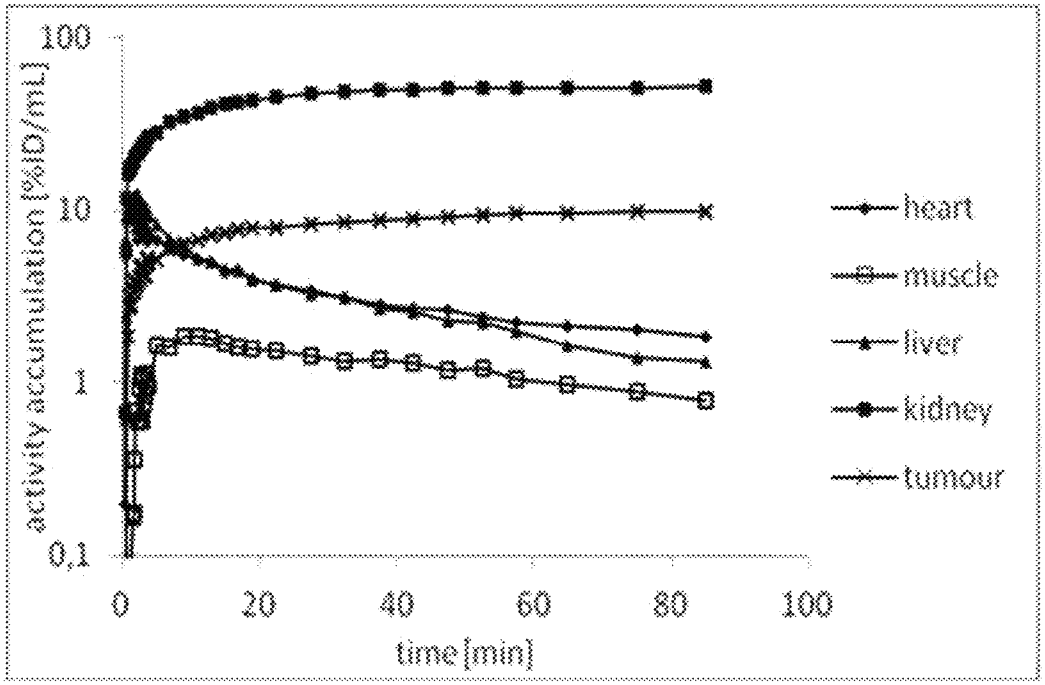

FIG. 17: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{18}$F-9 (free chelate) in a LNCaP tumor-bearing SCID mouse.

Figure 18:
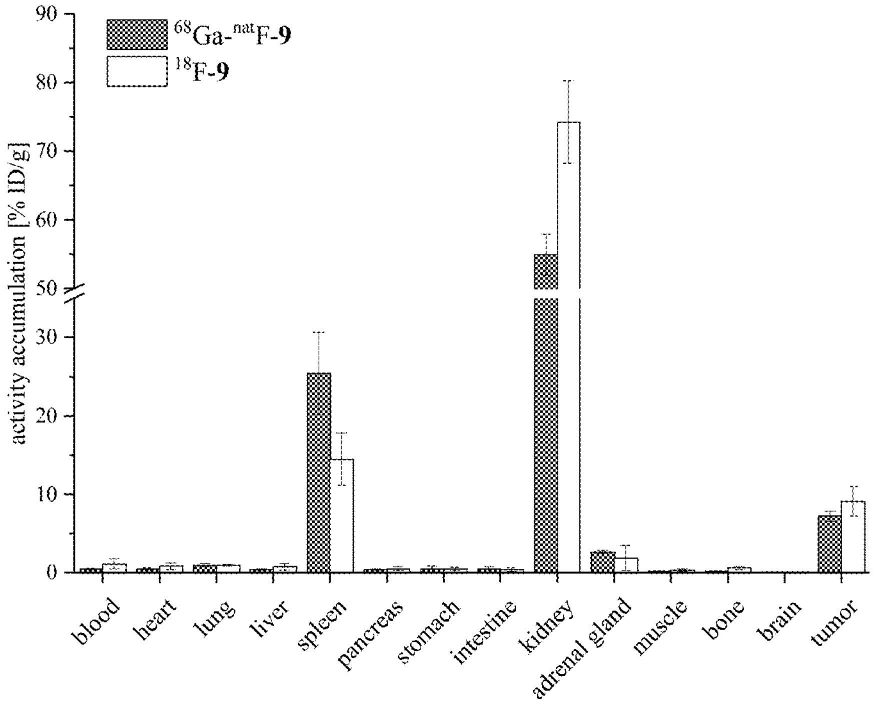

FIG. 18: Biodistribution (in % ID/g) of $^{68}$Ga-$^{nat}$F-9 (grey bars) and $^{18}$F-9 (free chelate) (white bars) at 1 hour p.i. in LNCaP tumor-bearing SCID mice. Data are expressed as mean±SD (n=3).

Figure 19:
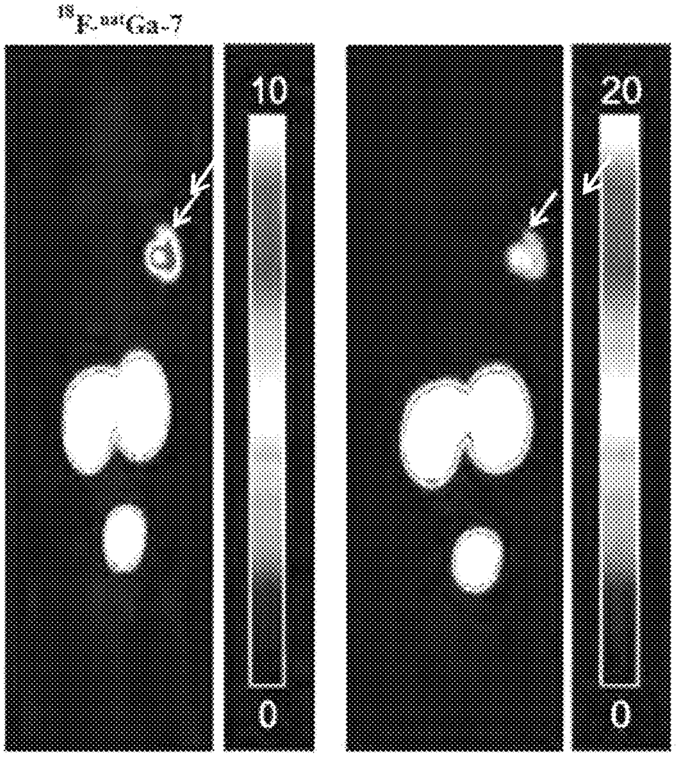

FIG. 19: Representative PET-images (maximum intensity projection, dorsal frame) of $^{18}$F-$^{nat}$Ga-7 (free chelate) and $^{18}$F-$^{nat}$Ga-7 (free chelate) co-injected with PMPA (8 mg/kg) in LNCaP tumor-bearing SCID mice (1 h p.i., 15 min acquisition time) and ROI quantification of selected organs of the PET scan without blocking. Data are expressed as mean±SD (n=3). % ID/mL=% injected dose per mL. Tumor positions are indicated by arrows.

Figure 20:
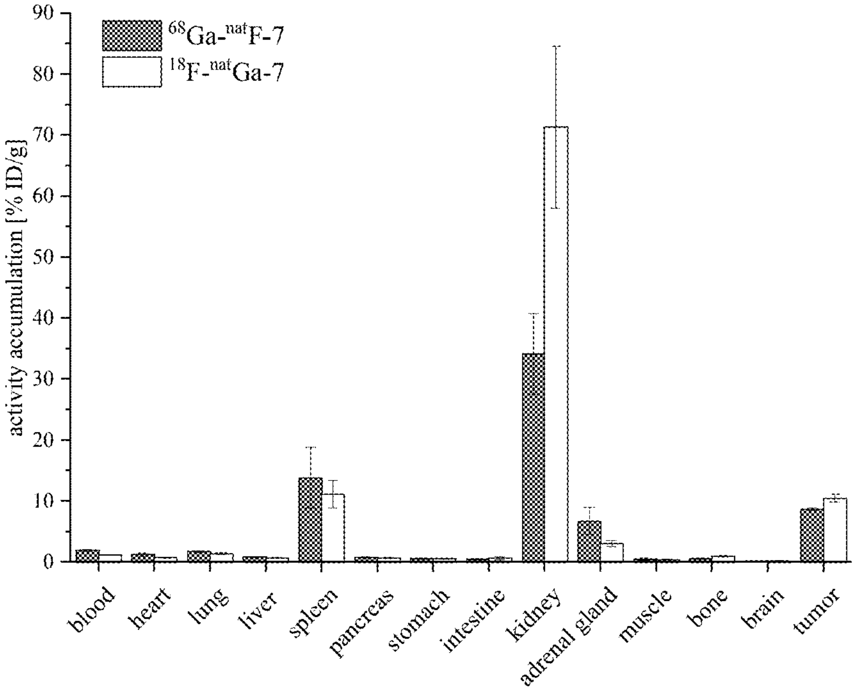

FIG. 20: Biodistribution (in % ID/g) of $^{18}$F-$^{nat}$Ga-7 (free chelate) (white bars), compared to the structurally identic compound $^{68}$Ga-$^{nat}$F-7 (free chelate) (grey bars) at 1 hour p.i. in LNCaP tumor-bearing SCID mice. Data are expressed as mean±SD (n=3).

Figure 21:
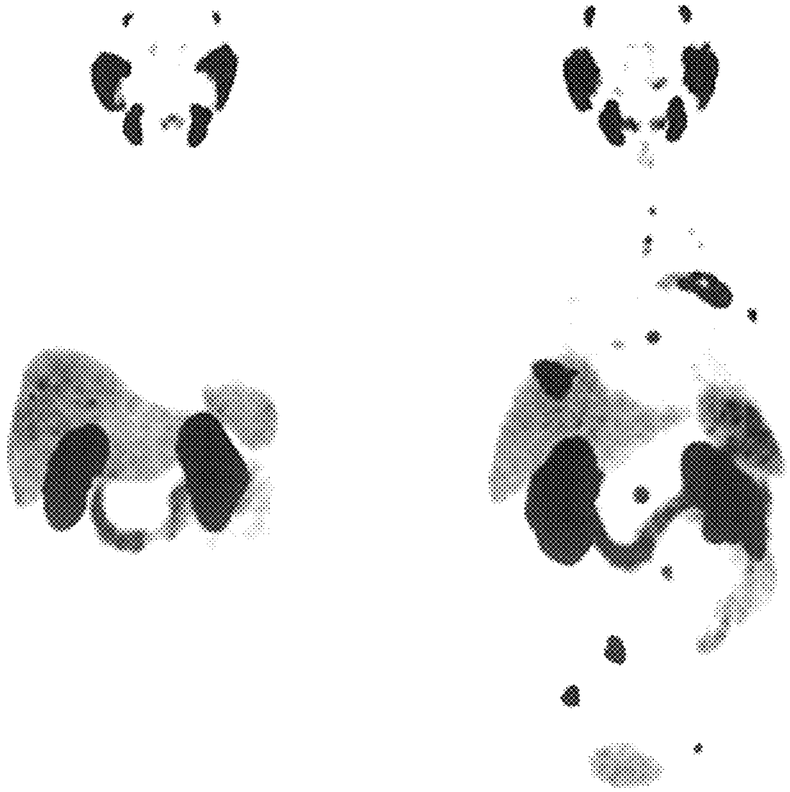

FIG. 21: left image demonstrates the maximum intensity projection (MIR) from PET of a subject with normal biodistribution (no tumor lesions detectable). Images were acquired 76 min post injection of 272 MBq 18F-labelled PSMA-SIFA3 (7). FIG. 21 right demonstrates the maximum intensity projection (MIP) from PET of a subject with moderately advanced disease exhibiting multiple tumor lesions with high lesion-to-background ratio. Images were acquired 102 min post injection of 312 MBq 18F-labelled PSMA-SIFA3 (7).

Figure 22:
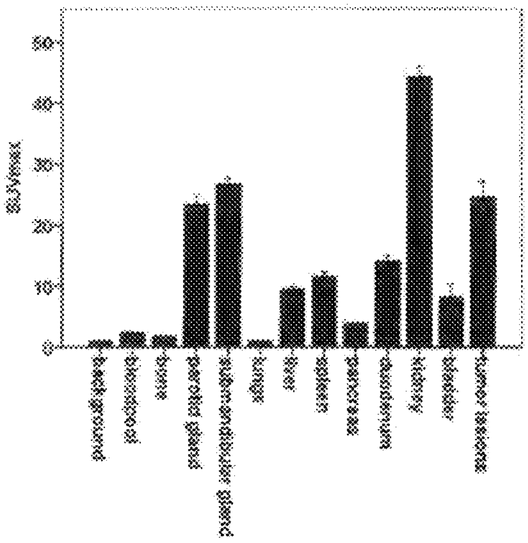
Figure 22:
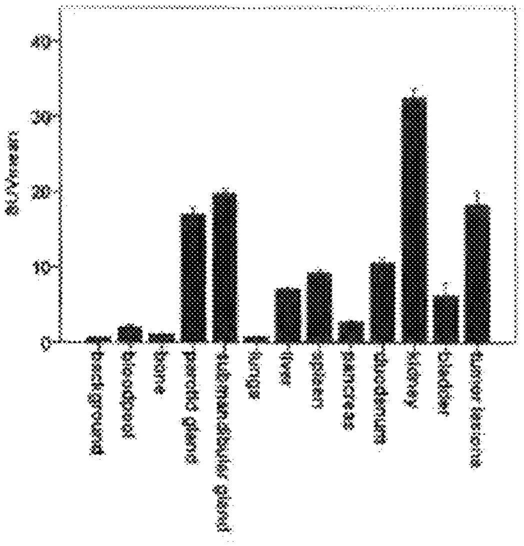

FIG. 22: is a graphical representation of Table 6

Figure 23:
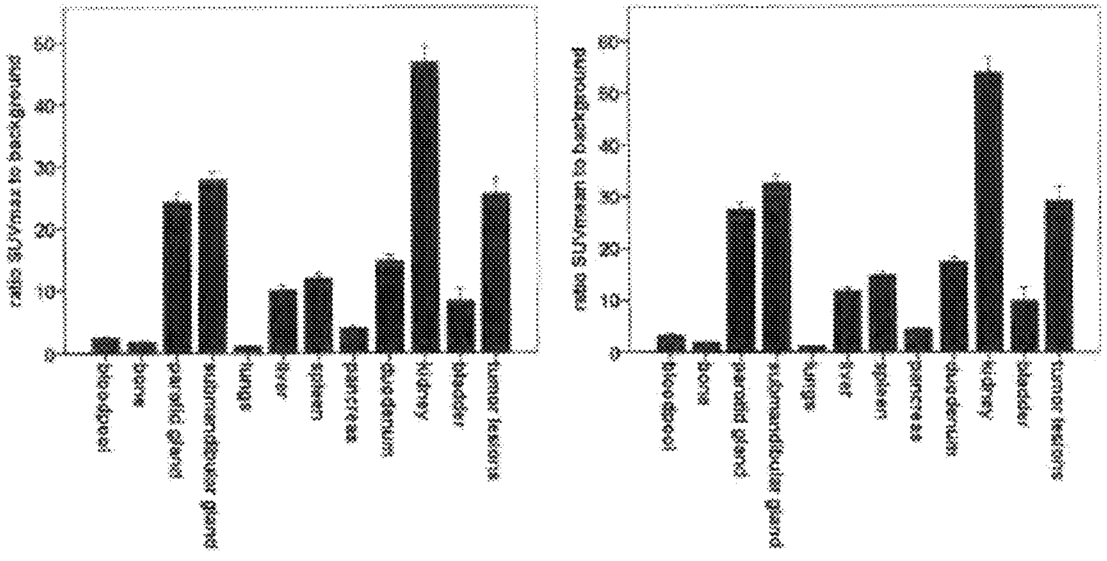

FIG. 23: is a graphical representation of Table 7

Figure 24:
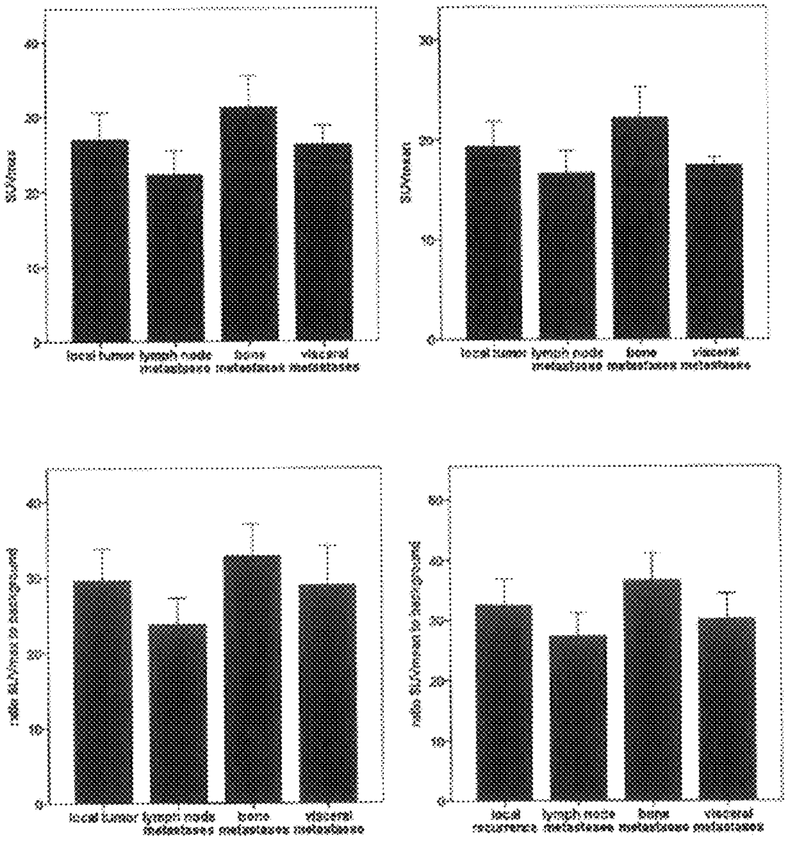

FIG. 24: is a graphical representation of Table 8

Figure 25:
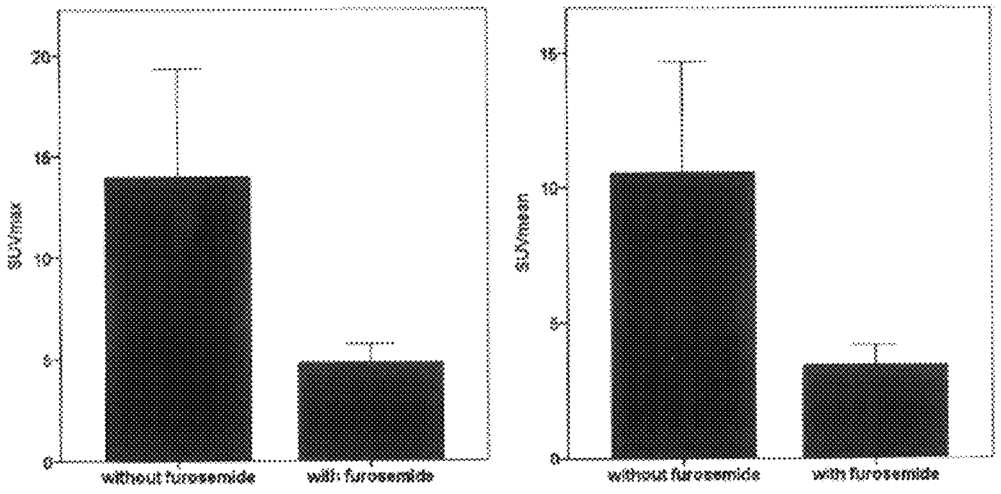

FIG. 25: is a graphical representation of Table 9

Figure 26:
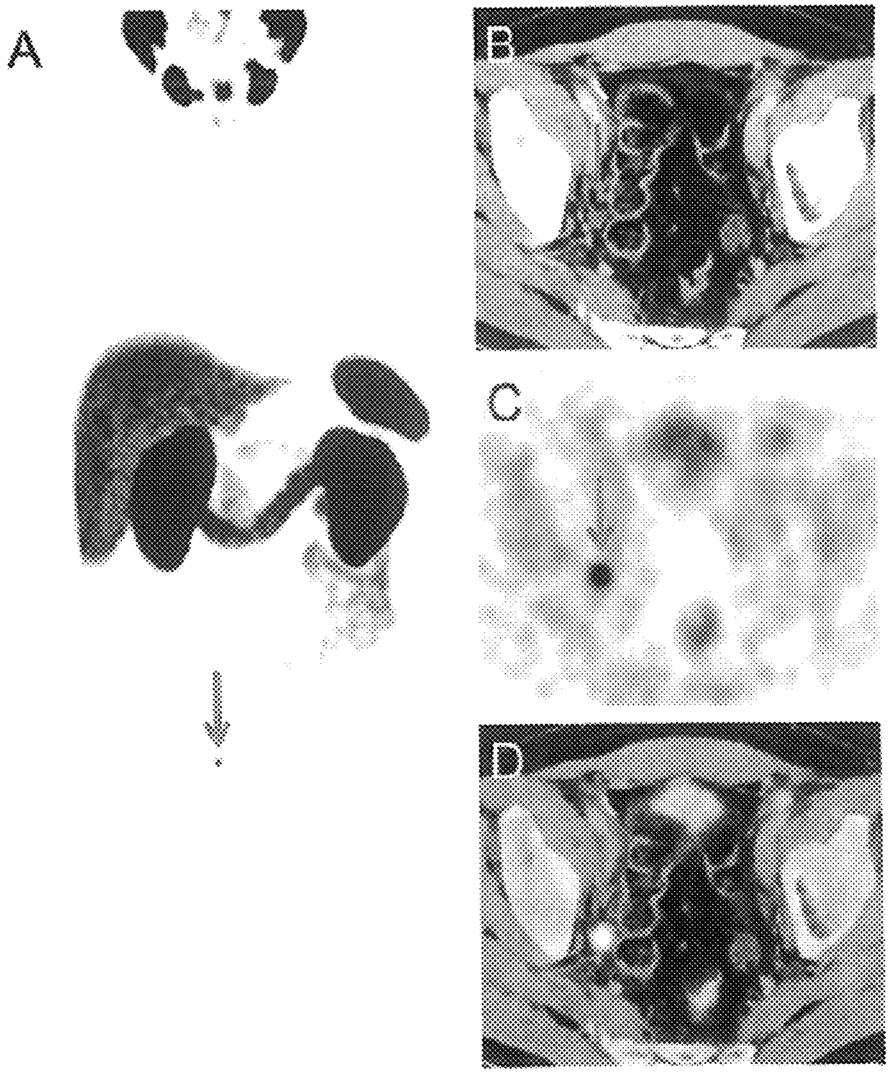

FIG. 26: shows: MIR (A) and transaxial images (B-D) of a 70 year old patient with biochemical recurrence 1.5 years after radical prostatectomy (Gleason 8, pT2c, pN1). A single prostate cancer typical lesion with 5 mm diameter in right pelvis with high uptake of 18F-labelled PSMA-SIFA3 (7) is present. Malignant nature of the lesion was verified by histopathology.

Figure 27:
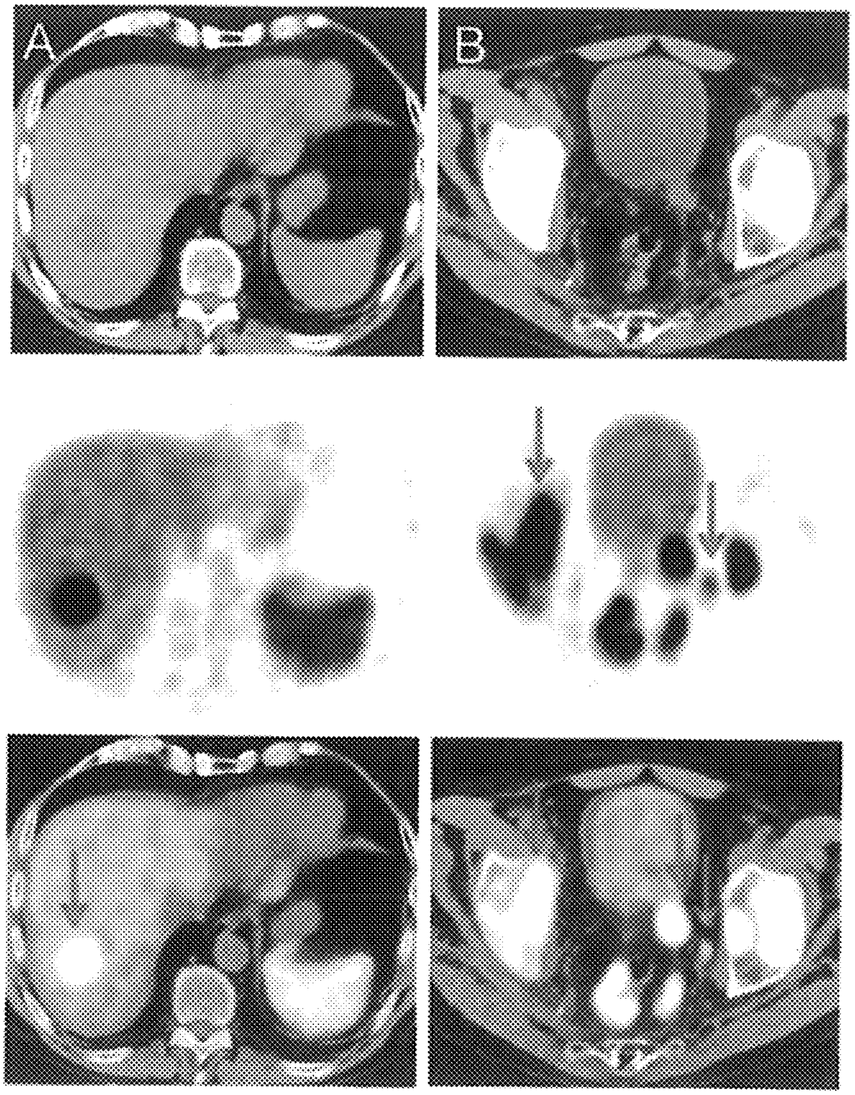

FIG. 27: Set of images of an 80 year old patient with progressive advanced castration resistant prostate cancer (PSA 66.4 ng/ml). Images shows high uptake of 18F-labelled PSMA-SIFA3 (7) in different classes of prostate cancer lesions (local tumor, lymph node metastases, bone metastases, liver metastases). Lesions demonstrated are as small as 2 mm (arrows indicate representative, not all tumor lesions).

Figure 28:
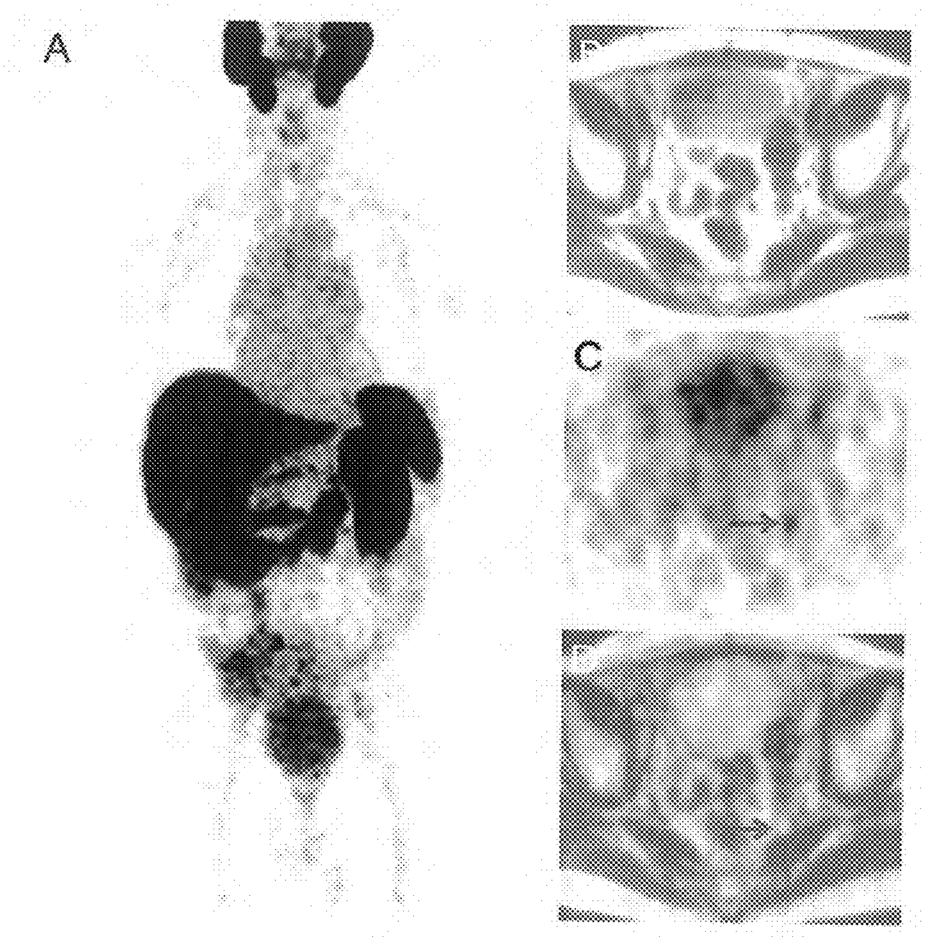

FIG. 28: shows proof of concept investigation of a $^{68}$Ga-labelled SiFA substituted chelator-based PET tracer.

Figure 29:
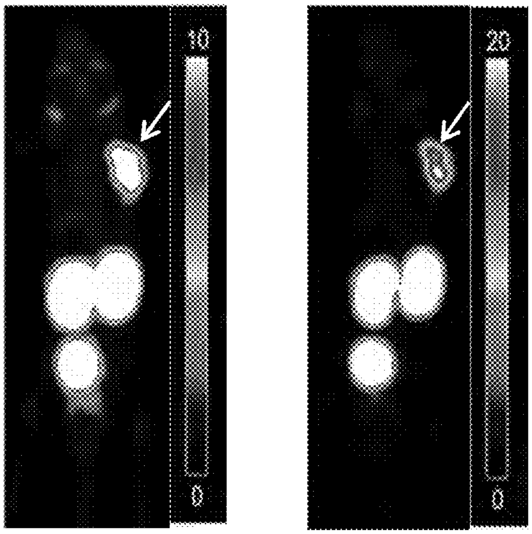

FIG. 29: Representative PET-images (maximum intensity projection, dorsal frame) of $^{18}$F-$^{nat}$Lu-rh-7 in LNCaP tumor-bearing SCID mice (1 h p.i., 15 min acquisition time) and ROI quantification of selected organs of the PET scan without blocking. Data are expressed as mean±SD (n=3). % ID/mL=% injected dose per mL. Tumor positions are indicated by arrows.

Figure 30:
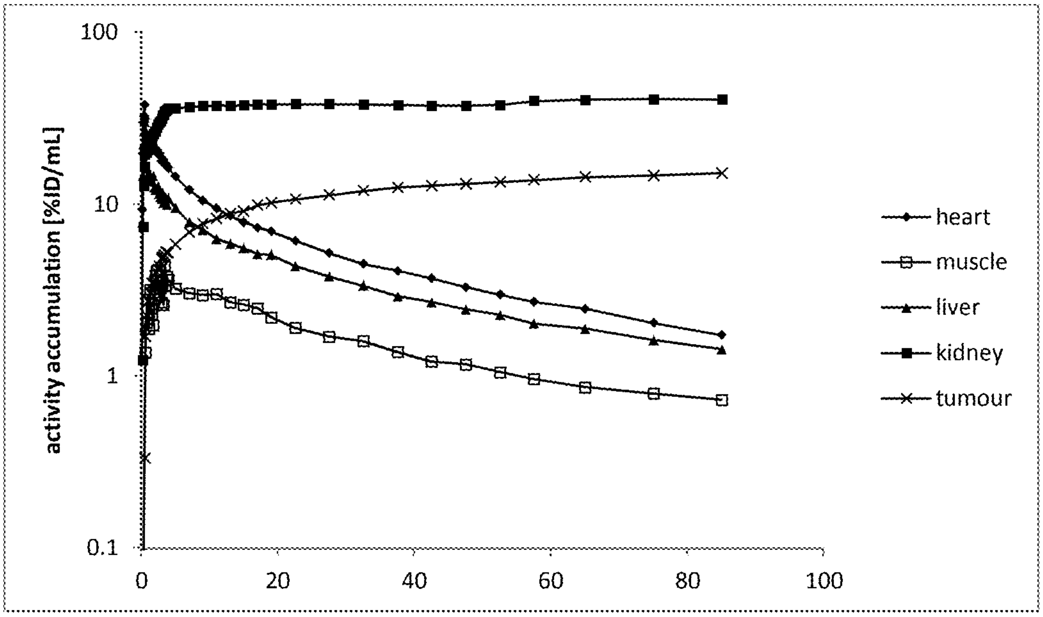

FIG. 30: Time activity curves (TACs, logarithmic plot) in % ID/mL derived from dynamic PET data (90 min acquisition time, OSEM 3D reconstruction) in blood pool (heart), muscle, kidneys, liver and LNCaP tumor xenograft of $^{18}$F-$^{nat}$Lu-rh-7 in a LNCaP tumor-bearing SCID mouse.

Figure 31:
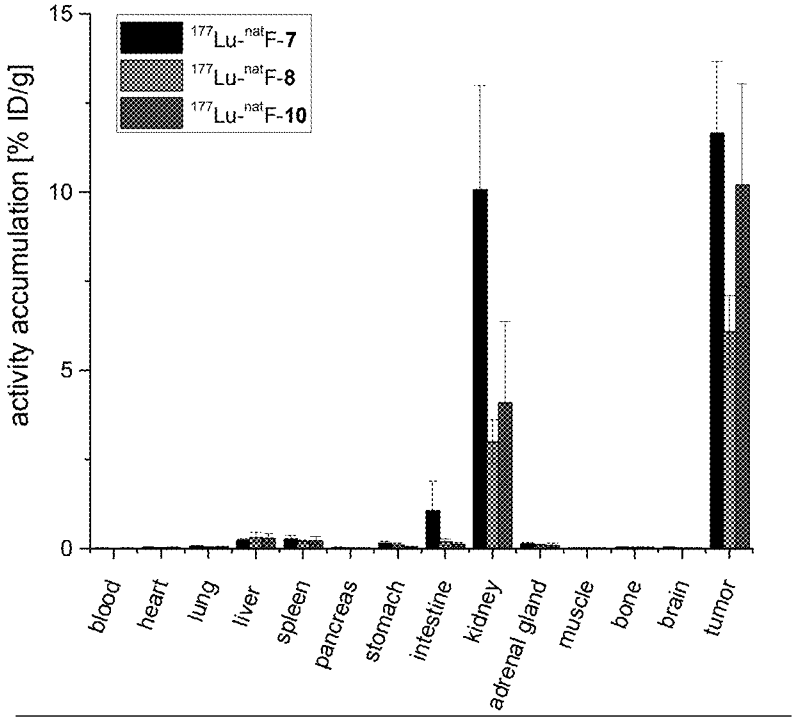

FIG. 31: Biodistribution (in % ID/g) of $^{177}$Lu-$^{nat}$F-7, $^{177}$Lu-$^{nat}$F-8 and $^{177}$Lu-$^{nat}$F-10 at 24 hour p.i. in LNCaP tumor-bearing SCID mice. Data are expressed as mean±SD (n=4).

Figure 32:
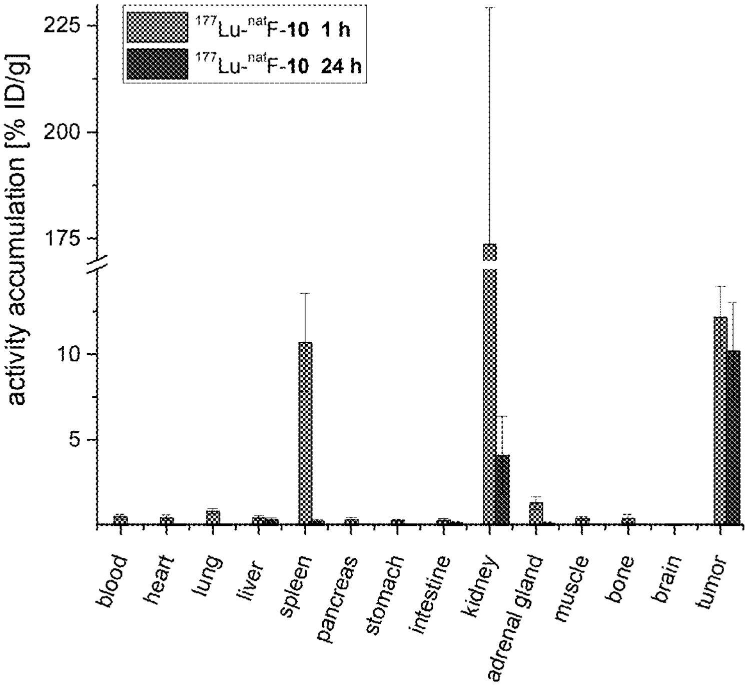

FIG. 32: Biodistribution (in % ID/g) of $^{177}$Lu-$^{nat}$F-10 at 1 hour and 24 h p.i. in LNCaP tumor-bearing SCID mice. Data are expressed as mean±SD (n=4).

Figure 33:
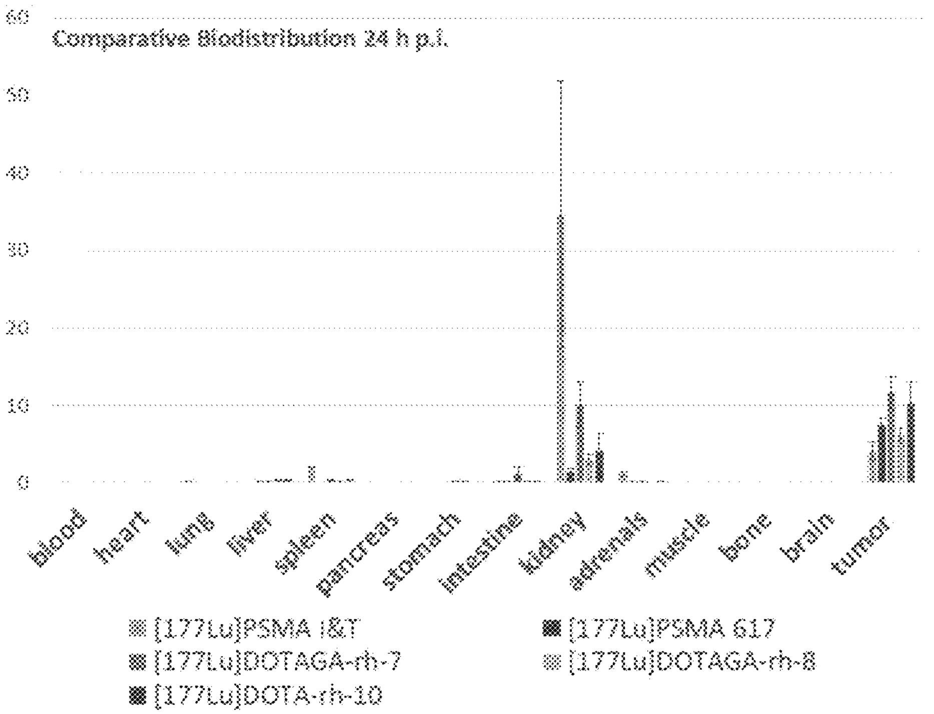
Figure 33:
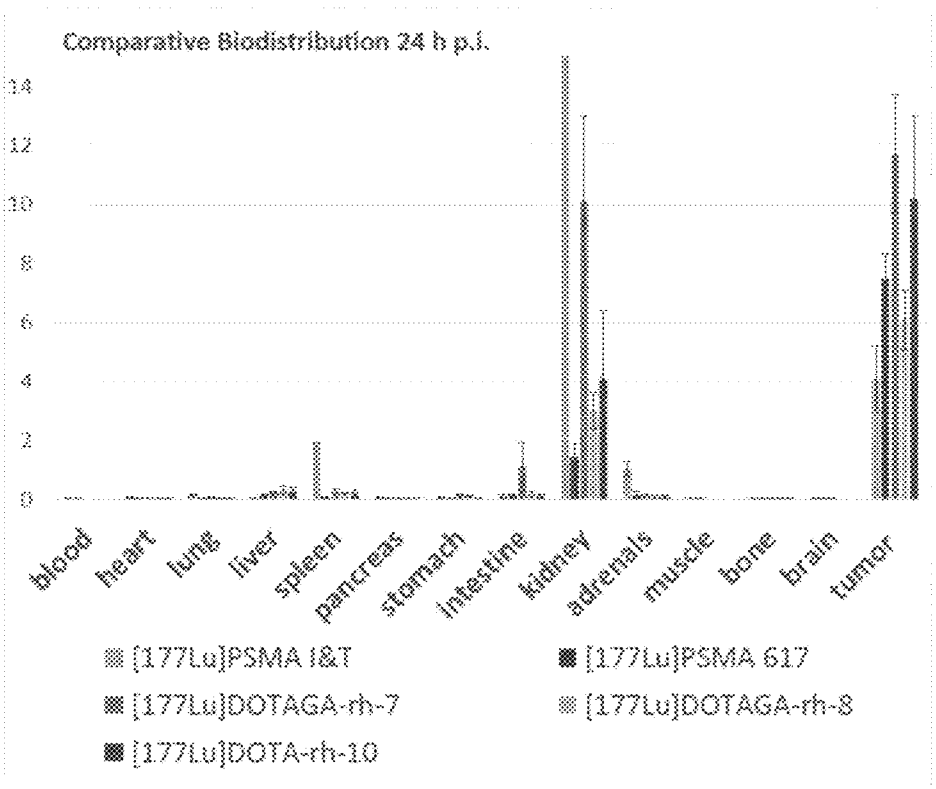

FIG. 33: Comparative biodistribution (in % ID/g) of established and new rhPSMA-ligands at 24 hour p.i. in LNCaP tumor-bearing SCID mice. Data are expressed as mean±SD (n=4-5).

Figure 34:
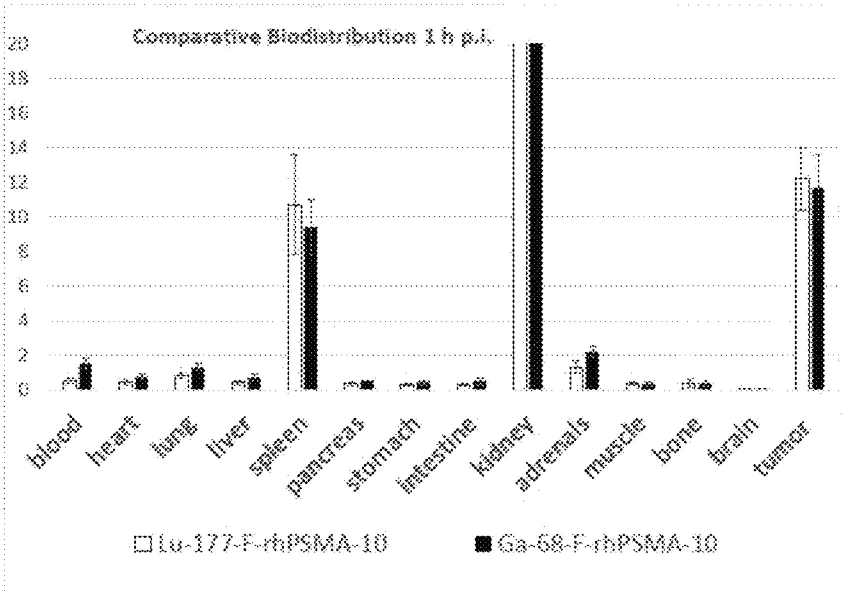
Figure 34:
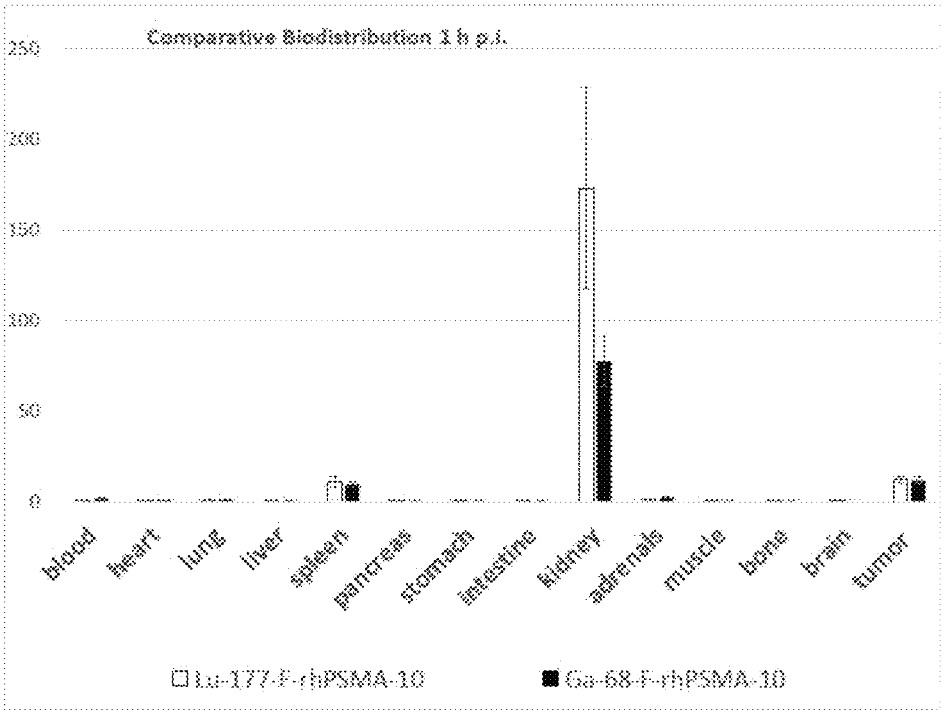

FIG. 34: Biodistribution (in % ID/g) of $^{177}$Lu-$^{nat}$F-10 and $^{68}$Ga-$^{nat}$F-10 at 1 hour p.i. in LNCaP tumor-bearing SCID mice. Data are expressed as mean±SD (n=4).

The Examples illustrate the invention.

EXAMPLE 1: MATERIAL AND METHODS

General

The Fmoc-(9-fluorenylmethoxycarbonyl-) and all other protected amino acid analogs were purchased from Bachem (Bubendorf, Switzerland) or Iris Biotech (Marktredwitz, Germany). The tritylchloride polystyrene (TCP) resin was obtained from PepChem (Tübingen, Germany). Chematech (Dijon, France) delivered the chelators DOTAGA-anhydride and NOTA. The TRAP chelator (1,4,7-triazacyclononane-1,4,7-tris[methylene(2-carboxyethyl)phosphinic acid]) was synthesized as described previously (Notni et al., Chemistry (Weinheim an der Bergstrasse, Germany) 16), 7174-85 (2010)). Synthesis of the silicon fluoride acceptor SIFA-benzoic acid was performed according to a previously published procedure (lovkova et al., Chemistry (Weinheim an der Bergstrasse, Germany) 15, 2140-7 (2009)). All necessary solvents and other organic reagents were purchased from either, Alfa Aesar (Karlsruhe, Germany), Sigma-Aldrich (Munich, Germany) or VWR (Darmstadt, Germany). Solid phase synthesis of the peptides was carried out by manual operation using an Intelli-Mixer syringe shaker (Neolab, Heidelberg, Germany). Analytical and preparative reversed-phase high pressure chromatography (RP-HPLC) were performed using Shimadzu gradient systems (Shimadzu Deutschland GmbH, Neufahrn, Germany), each equipped with a SPD-20A UV/Vis detector (220 nm, 254 nm). A Nucleosil 100 C18 (125×4.6 mm, 5 μm particle size) column (CS GmbH, Langerwehe, Germany) was used for analytical measurements at a flow rate of 1 mL/min. Both specific gradients and the corresponding retention times $t_R$ are cited in the text. Preparative HPLC purification was done with a Multospher 100 RP 18 (250×10 mm, 5 μm particle size) column (CS GmbH, Langerwehe, Germany) at a constant flow rate of 5 mL/min. Analytical and preparative radio RP-HPLC was performed using a Nucleosil 100 C18 (5 μm, 125×4.0 mm) column (CS GmbH, Langerwehe, Germany). Eluents for all HPLC operations were water (solvent A) and acetonitrile (solvent B), both containing 0.1% trifluoroacetic acid. Electrospray ionization-mass spectra for characterization of the substances were acquired on an expression$^L$ CMS mass spectrometer (Advion Ltd., Harlow, UK). Radioactivity was detected through connection of the outlet of the UV-photometer to a NaI(TI) well-type scintillation counter from EG&G Ortec (Munich, Germany). Gel permeation chromatography (GPC) was done on Sephadex GP-10 (100 g, bed size approx. 30×3 cm) with water as eluent, separating the eluate in 20 mL fractions. NMR spectra were recorded on Bruker AVHD-300 or AVHD-400 spectrometers at 300 K. pH values were measured with a SevenEasy pH-meter (Mettler Toledo, Gieβen, Germany).

Synthesis Protocols

1) Solid-Phase Peptide Synthesis Following the Fmoc-Strategy

TCP-Resin Loading

Loading of the tritylchloride polystyrene (TCP) resin with a Fmoc-protected amino acid (AA) was carried out by stirring a solution of the TCP-resin (1.95 mmol/g) and Fmoc-AA-OH (1.5 eq.) in anhydrous DCM with DIPEA (4.5 eq.) at room temperature for 2 h. Remaining tritylchloride was capped by the addition of methanol (2 mL/g resin) for 15 min. Subsequently the resin was filtered and washed with DCM (2×5 mL/g resin), DMF (2×5 mL/g resin), methanol (5 mL/g resin) and dried in vacuo. Final loading/of Fmoc-AA-OH was determined by the following equation:

$$l\left[\frac{\text{mmol}}{\text{g}}\right] = \frac{(m_2 - m_1)\times 1000}{(M_W - M_{HCl})m_2}$$

$m_2$=mass of loaded resin [g]

$m_1$=mass of unloaded resin [g]

$M_w$=molecular weight of AA [g/mol]

$M_{HCl}$=molecular weight of HCl [g/mol]

On-Resin Peptide Formation The respective side-chain protected Fmoc-AA-OH (1.5 eq.) was dissolved in DMF (8 mL/g resin) and pre-activated by adding TBTU (1.5 eq.), HOBt (1.5 eq.) and DIPEA (4.5 eq.). Pre-activation for SIFA-BA was performed analogously. For azido-substituted amino acids (2.0 eq.), HATU (3.0 eq.), HOAt (3.0 eq.) and DIPEA (6.0 eq.) were used. After activation for 15 minutes, the solution was added to resin-bound free amine peptide TCP-AA-$NH_2$ and shaken for 2 h at room temperature. Subsequently, the resin was washed with DMF (6×5 mL/g resin) and after Fmoc-deprotection the next amino acid was coupled analogously.

On-Resin Fmoc-Deprotection

The resin-bound Fmoc-peptide was treated with 20% piperidine in DMF (v/v, 8 mL/g resin) for 5 min and subsequently for 15 min. Afterwards, the resin was washed thoroughly with DMF (8×5 mL/g resin).

On-Resin Dde-Deprotection

The Dde-protected peptide (1.0 eq.) was dissolved in a solution of 2% hydrazine monohydrate in DMF (v/v, 5 mL/g resin) and shaken for 15 min. In the case of present Fmoc-groups, Dde-deprotection was performed by adding a solution of imidazole (0.46 g), hydroxylamine hydrochloride (0.63 g) in NMP (2.5 mL) and DMF (0.5 mL) for 3 h at room temperature. After deprotection the resin was washed with DMF (6×5 mL/g resin).

On-Resin Alloc-Deprotection

The allyloxy-protecting group was removed by the addition of triisopropylsilane (TIPS) (50.0 eq.) and tetrakis (triphenylphosphine)palladium(0) ($Pd(PPh_3)_4$) (0.3 eq.) dissolved in DCM (6 mL). After 1.5 h at room temperature, the resin was washed with DCM (6×5 mL/g resin).

tBu/Boc Deprotection

Removal of tBu/tBoc-protecting groups was carried out by dissolving the crude product in TFA and stirring for 40 min at RT. After removing TFA under a stream of nitrogen, the residue was dissolved in a mixture of tert-butanol and water. After lyophilisation the crude peptide was obtained.

Peptide Cleavage from the Resin a) Preservation of acid labile protecting groups: The resin-bound peptide was dissolved in a mixture of DCM/TFE/AcOH (v/v/v; 6/3/1, 8 mL/g resin) and shaken for 30 min. The solution containing the fully protected peptide was filtered off and the resin was treated with another portion of the cleavage solution for 30 min. Both fractions were combined and acetic acid was removed under reduced pressure by successively adding toluene and water. After lyophilisation of remaining water, the crude fully protected peptide was obtained.

b) Deprotection of all acid labile protecting groups: The fully protected resin-bound peptide was dissolved in a mixture of TFA/TIPS/water (v/v/v; 95/2.5/2.5) and shaken for 30 min. The solution was filtered off and the resin was treated in the same way for another 30 min. Both filtrates were combined and concentrated under a stream of nitrogen. After dissolving the residue in a mixture of tert-butanol and water and subsequent lyophilisation the crude peptide was obtained.

2) Synthesis of the Binding Motifs (1)

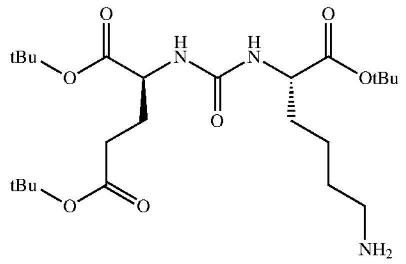

Lys-urea-Glu ((tBuO)KuE(OtBu)$_2$)

The synthesis of the tBu-protected Lys-urea-Glu binding motif (EuK) was carried out as described previously by solution phase synthesis (Weineisen et al., EJNMMI research 4, 63 (2014)). The product was obtained as a waxy solid (91.5%). HPLC (10 to 90% B in 15 min): $t_R$=12.6 min. Calculated monoisotopic mass ($C_{24}H_{45}N_3O_7$): 487.6 found: m/z=488.3 $[M+H]^+$, 510.3 $[M+Na]^+$.

(2)

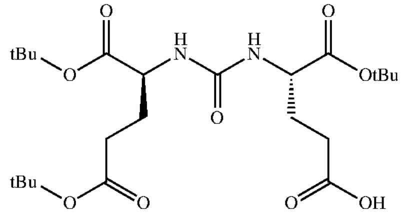

Glu-urea-Glu ((tBuO)EuE(OtBu)$_2$)

The tBu-protected Glu-urea-Glu binding motif (EuE) was synthesized according to a previously published procedure (Weineisen et al., EJNMMI research 4, 63 (2014)). The product was obtained as a hygroscopic solid (84%). HPLC (10% to 90% B in 15 min): $t_R$=11.3 min. Calculated monoisotopic mass ($C_{23}H_{49}N_2O_9$): 488.3; found: m/z=489.4 [M+H]$^+$, 516.4 [M+Na]$^+$.

(3)

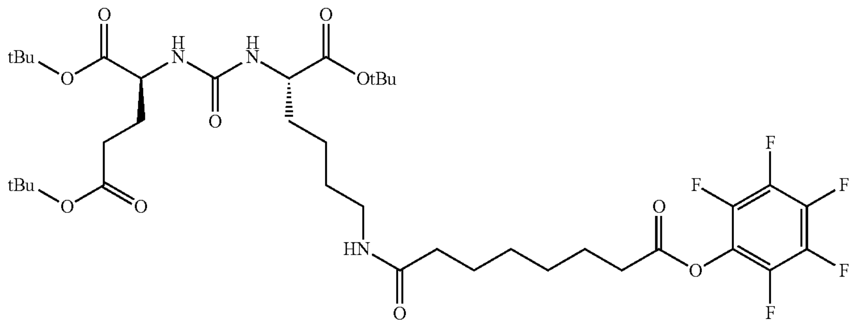

PfpO-Sub-(tBuO)KuE(OtBu)$_2$

Conjugation of EuK to the suberic acid spacer was performed as described previously (Weineisen et al., EJNMMI research 4, 63 (2014)). The product was obtained as a colorless oil (72%). HPLC (10 to 90% B in 15 min): $t_R$=15.5 min. Calculated monoisotopic mass ($C_{38}H_{56}F_5N_3O_{10}$): 809.4 found: m/z=810.6 [M+H]$^+$, 832.4 [M+Na]$^+$.

Conjugation of the EuK-sub-moiety (3) to the Peptide

The N-terminal deprotected peptide (1.0 eq.) was added to a solution of 3 (1.2 eq.) in DMF and TEA (8 eq.) was added. After stirring the solution for 2 h at room temperature, DMF was removed in vacuo. For cleavage of the tBu-esters, TFA was added and the solution was stirred for 45 min at room temperature. After removing TFA under a stream of nitrogen, the crude product was purified by RP-HPLC.

(4)

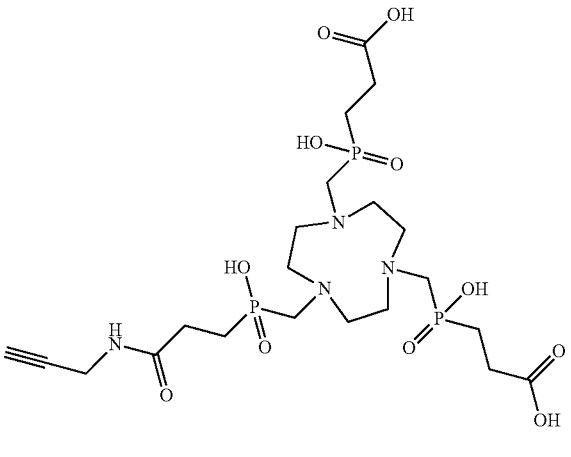

3) Synthesis of propargyl-TRAP

Synthesis of propargyl-TRAP was carried out as described previously (Reich et al., Chemical communications (Cambridge, England) 53, 2586-2589 (2017)). Final purification was done by preparative HPLC, affording 60.2 mg (82.4 μmol, 46%) of propargyl-TRAP as a colorless solid. HPLC (2 to 40% B in 20 min): $t_R$=6.0 min. Calculated monoisotopic mass ($C_{21}H_{39}N_4O_{11}P_3$): 616.5 found: m/z=617.5 [M+H]$^+$.

$^1$H-NMR (300 MHz, $D_2O$, 300 K) δ=1.96-2.08 (m, 6H, C(O)—$CH_2$), 2.46-2.55 (m, 2H, $P^B$—$CH_2$—C), 2.59-2.70 (m, 4H, $P^A$—$CH_2$-C), 3.36 (d, 2H, $^2J_{PH}$=6 Hz, $P^B$—$CH_2$—N), 3.41 (d, 4H, $^2J_{PH}$=6 Hz, $P^A$—$CH_2$—N), 3.47-3.48 (m, 12H, ring-$CH_2$), 3.95 (d, 2H, $CH_2$—C≡CH, $^4J_{HH}$=3 Hz) ppm*. $^{13}C\{^1H\}$-NMR (101 MHz, $D_2O$, 300 K) δ=24.61 (d, $^1J_{PP}$=95 Hz, $P^B$—C—C), 25.07 (d, $^1J_{PP}$=94 Hz, $P^A$—C—C), 26.71 (d, $^2J_{PP}$=4 Hz, $P^B$—C—C), 27.82 (d, $^2J_{PP}$=3 Hz, $P^A$—C—C), 28.89 (C—C≡C), 51.29/51.41/51.50 (three different ring-C), 53.66 (d, $^1J_{PP}$=91 Hz, N—C—$P^A$), 53.66 (d, $^1J_{PP}$=90 Hz, N—C—$P^B$), 71.79 (C—C≡C), 79.65 (C—C≡C), 174.46 (d, $^3J_{PP}$=14 Hz, N(H)—C=$O^B$), 177.24 (d, $^3J_{PP}$=13 Hz, C=$O^A$) ppm *. $^{31}P\{^1H\}$—NMR (162 MHZ, $D_2O$, 300 K) δ=37.99 ($P^A$), 38.68 ($P^B$) ppm*. *: indices $^A$ and $^B$ indicate P and O atoms belonging to the undecorated$^A$ and decorated$^B$ side arm, respectively.

Coupling of Propargyl-TRAP (4) to the Peptide

For conjugation of azide-functionalized peptides to propargyl-TRAP via copper(I)-catalyzed alkyne-azide cycloaddition a previously developed procedure was applied (Reich et al., Chemical communications (Cambridge, England) 53, 2586-2589(2017)). Briefly, propargyl-TRAP (1.0 eq.) was dissolved in water (40 mM solution) and combined with a solution of the peptide (1.1 eq.) in a 1:1 (v/v) mixture of tBuOH and water. Subsequently, a solution of sodium ascorbate (0.5 M, 50 eq.) in water was added. In order to start the reaction, an aqueous solution of $Cu(OAc)_2 \cdot H_2O$ (0.05 M, 1.2 eq.) was added, which resulted in a brown precipitate that dissolved after stirring in a clear green solution. For demetallation of TRAP, an aqueous solution of 1,4,7-triazacyclononane-1,4,7-triacetic acid (NOTA, 8 mM, 12 eq.) was added and the pH was adjusted to 2.2 with 1 M aq. HCl. After either 1 h at 60° C., or 48 h at room temperature the mixture was directly subjected to preparative HPLC purification.

4) Conjugation of DOTAGA

The condensation of peptides and the respective chelator DOTAGA-anhydride are described in several publications and summarized as follows: The N-terminal deprotected peptide (1.0 eq.) was dissolved together with DOTAGA-anhydride (1.5 eq.) and DIPEA (10.0 eq.) in dry DMF. After stirring the reaction mixture overnight, DMF was removed in vacuo, yielding the crude product.

5) Synthesis of EuK-Based PSMA-SIFA Inhibitors (5)

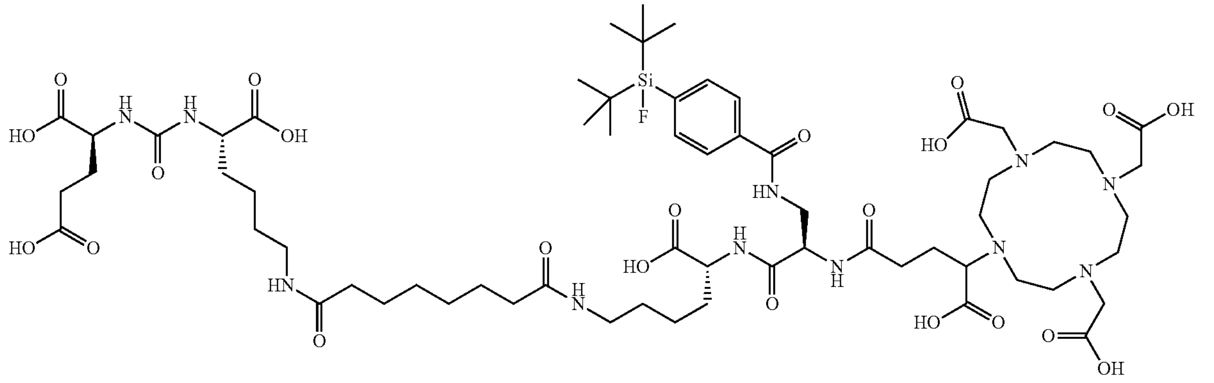

PSMA-SIFA1

PSMA-SIFA1 was synthesized according to standard Fmoc-solid-phase peptide synthesis (SPPS) on a tritylchloride polystyrene (TCP) resin, applying the above mentioned methods. Briefly, resin bound Fmoc-D-Lys (Boc) was Fmoc deprotected with 20% piperidine in DMF and Fmoc-D-Dap (Dde)-OH (2.0 eq.) was conjugated applying HOBt (2.0 eq.), TBTU (2.0 eq.) and DIPEA (6.0 eq.) in DMF. After orthogonal Dde-deprotection with imidazole and hydroxylamine hydrochloride in a mixture of NMP and DMF, SIFA-BA (1.5 eq.) was conjugated analogously. Subsequent Fmoc-deprotection and mild cleavage from the resin with TFE and AcOH in DCM yielded the Boc-protected peptide backbone. Condensation of DOTAGA-anhydrid (1.5 eq.) was performed by adding DIPEA (10 eq.) in DMF. After Boc-deprotection in TFA, the PfpO-Sub-(tBuO) KuE $(OtBu)_2$ moiety (1.2 eq.) was added in a mixture of TEA (8 eq.) and DMF. Final cleavage of the tBu-esters in TFA and RP-HPLC purification yielded PSMA-SIFA1 (70%) as a colorless solid. HPLC (10 to 90% B in 15 min): $t_R$=9.1 min. Calculated monoisotopic mass ($C_{63}H_{102}FN_{11}O_{22}Si$): 1411.7 found: m/z=1412.3 $[M+H]^+$, 706.8 $[M+2H]^{2+}$.

Scheme 1: Synthesis of PSMA-SIFA1

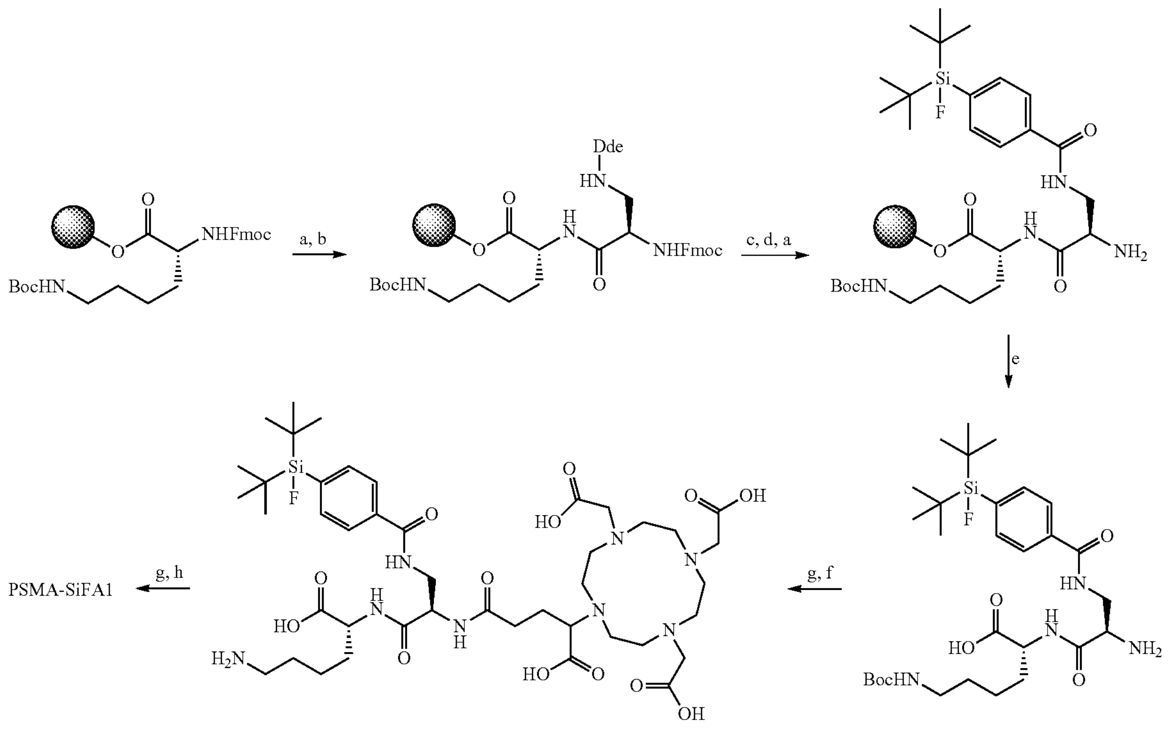

a) 20% piperidine (DMF); b) Fmoc-D-Dap(Dde)-OH, HOBt, TBTU, DIPEA (DMF); c) imidazole, hydroxylamine hydrochloride, (NMP, DMF);
d) SIFA-BA, HOBt, TBTU, DIPEA (DMF); e) TFE, AcOH, (DCM); f) DOTAGA-anhydrid, DIPEA, (DMF); g) TFA; h) PfpO-Sub-(tBuO)KuE$(OtBu)_2$, TEA, (DMF).

(6)

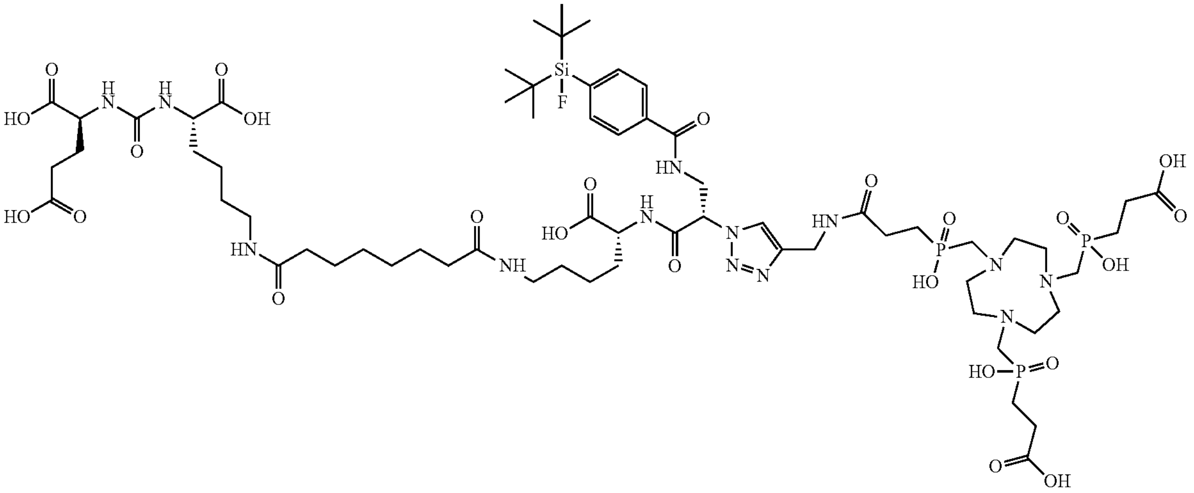

PSMA-SIFA2

Synthesis of PSMA-SIFA2 was carried out by applying the general methods and procedures mentioned before. Shortly, resin bound Fmoc-D-Lys (Boc)-OH was Fmoc-deprotected with 20% piperidine in DMF and conjugated to $N_3$-L-Dap (Fmoc)-OH (2.0 eq.) with HATU (3.0 eq.), HOAt (3.0 eq.) and DIPEA (6.0 eq.) in DMF. After cleavage of the Fmoc-group, SIFA-BA (1.5 eq.) was added with HOBt (1.5 eq.), TBTU (1.5 eq.) and DIPEA (4.5 eq.) in DMF. Subsequent cleavage from the resin with TFA yielded the fully deprotected peptide backbone. For conjugation of the EuK-moiety, PfpO-Sub-(tBuO) KuE $(OtBu)_2$ (1.2 eq.) was added in a mixture of TEA (8 eq.) and DMF. Cleavage of the tBu-esters was performed by adding TFA. In a final step the purified peptide (1.1 eq.) was reacted with propargyl-TRAP (1.0 eq.) in a copper(I)-catalyzed alkyne-azide cycloaddition, as mentioned above. After RP-HPLC purification PSMA-SIFA2 (4%) was obtained as a colourless solid. HPLC (10 to 90% B in 15 min): $t_R$=8.5 min. Calculated monoisotopic mass ($C_{65}H_{109}FN_{13}O_{24}P_3Si$): 1595.7 found: m/z=1596.5 $[M+H]^+$, 799.1 $[M+2H]^2$+.

Scheme 2
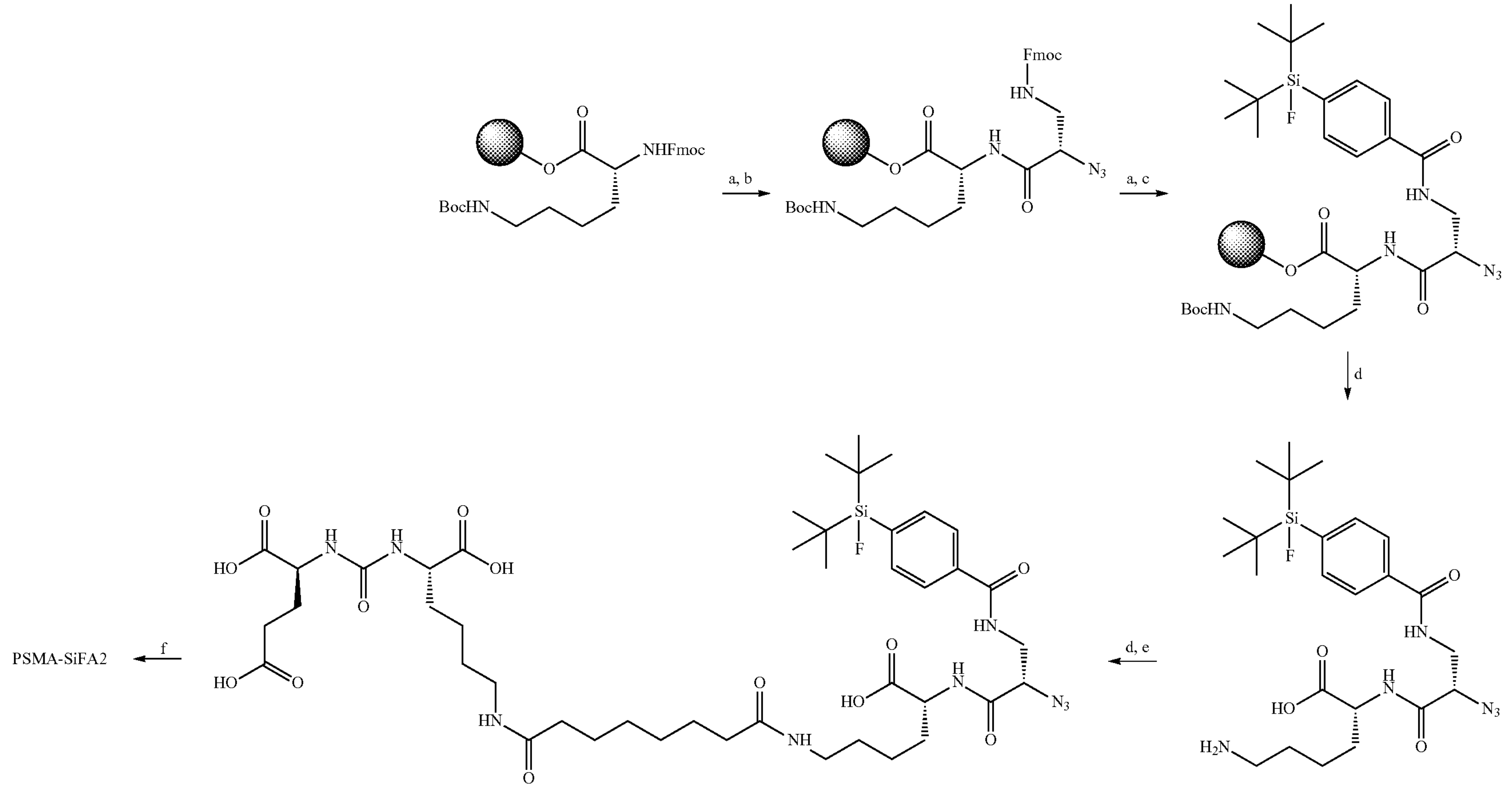
Synthesis of PSMA-SIFA2: a) 20% piperdine (DMF); b) $N_3$-L-Dap(Fmoc)-OH, HATU, HOAt, DIPEA (DMF); c) SIFA-BA, HOBt, TBTU, DIPEA (DMF); d) TFA; e) PfpO-Sub-(tBuO)-KuE(OtBu)$_2$, TEA, (DMF); f) propargyl-TRAP, Cu(OAc)$_2$•$H_2O$, sodium ascorbate (tBuOH, $H_2O$).

6) Synthesis of EuE-Based PSMA-SIFA Inhibitors (7)

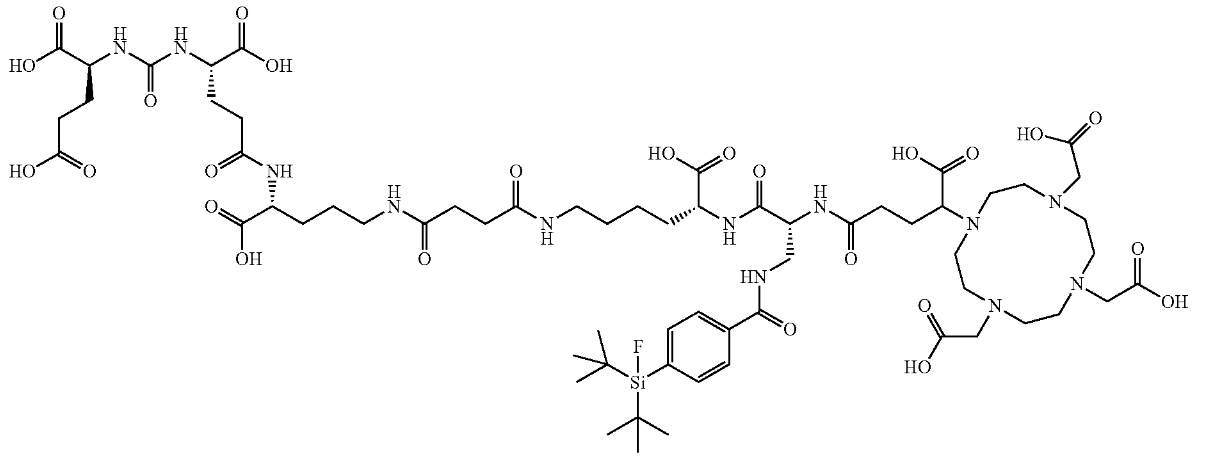

PSMA-SIFA3

PSMA-SIFA3 was synthesized applying the standard Fmoc-SPPS protocol described above. Briefly, resin bound Fmoc-D-Orn(Dde)-OH was Fmoc-deprotected with 20% piperidine in DMF and $(tBuO)EuE(OtBu)_2$ (2.0 eq.) was conjugated with HOBt (2.0 eq.), TBTU (2.0 eq.) and DIPEA (6.0 eq.) in DMF. After cleavage of the Dde-group with a mixture of 2% hydrazine in DMF, a solution of succinic anhydride (7.0 eq.) and DIPEA (7.0 eq.) in DMF was added. Conjugation of Fmoc-D-Lys-OAll·HCl (1.5 eq.) was achieved by adding a mixture of HOBt (1.5 eq.), TBTU (1.5 eq.) and DIPEA (4.5 eq.) in DMF. After cleavage of the Fmoc-group with 20% piperidine in DMF, the free amine was conjugated to Fmoc-D-Dap (Dde)-OH (2.0 eq.) after pre-activation of the amino acid in a mixture of HOBt (2.0 eq.), TBTU (2.0 eq.) and DIPEA (6.0 eq.) in DMF. Following orthogonal Dde-deprotection was done using imidazole and hydroxylamine hydrochloride dissolved in a mixture of NMP and DMF. SIFA-BA (1.5 eq.) was reacted with the free amine of the side chain with HOBt (1.5 eq.), TBTU (1.5 eq.) and DIPEA (4.5 eq.) as activation reagents in DMF. The allyloxy-protecting group was removed by the addition of TIPS (50.0 eq.) and $Pd(PPh_3)_4$ (0.3 eq.) dissolved in DCM. After Fmoc-deprotection with piperidine, the peptide was cleaved from the resin with preservation of the acid labile protecting groups by using a mixture of TFE and AcOH in DCM. Final condensation of DOTAGA-anhydrid (1.5 eq.) was achieved with piperidine (10 eq.) in DMF. After cleavage of the fBu-esters of the EuE-moiety with TFA, the crude peptide was purified by RP-HPLC, yielding PSMA-SIFA3 (24%) as a colorless solid. HPLC (10 to 70% B in 15 min): $t_R$=10.4 min. Calculated monoisotopic mass ($C_{63}H_{99}FN_{12}O_{25}Si$): 1470.7 found: m/z=1471.8 $[M+H]^+$, 736.7 $[M+2H]^{2+}$.

Scheme 3: Synthesis of PSMA-SIFA3:

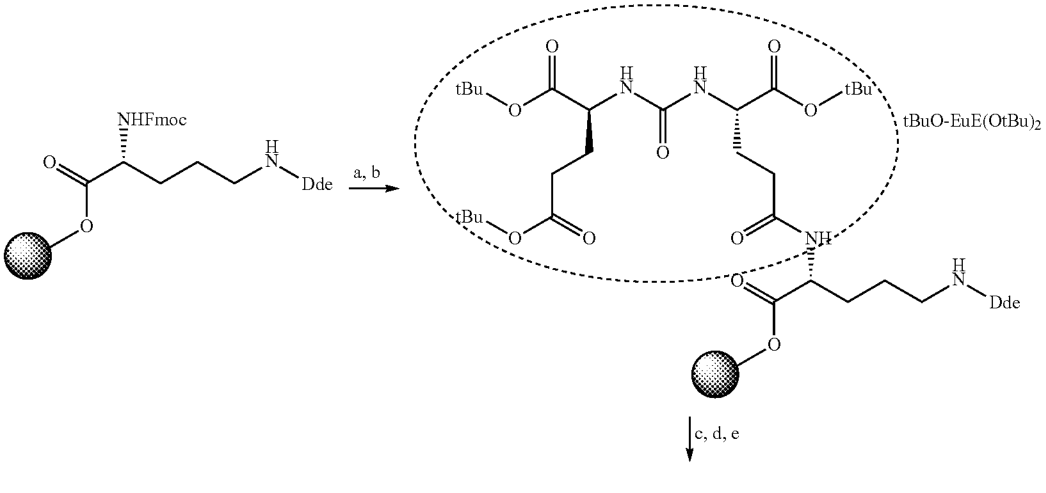

-continued

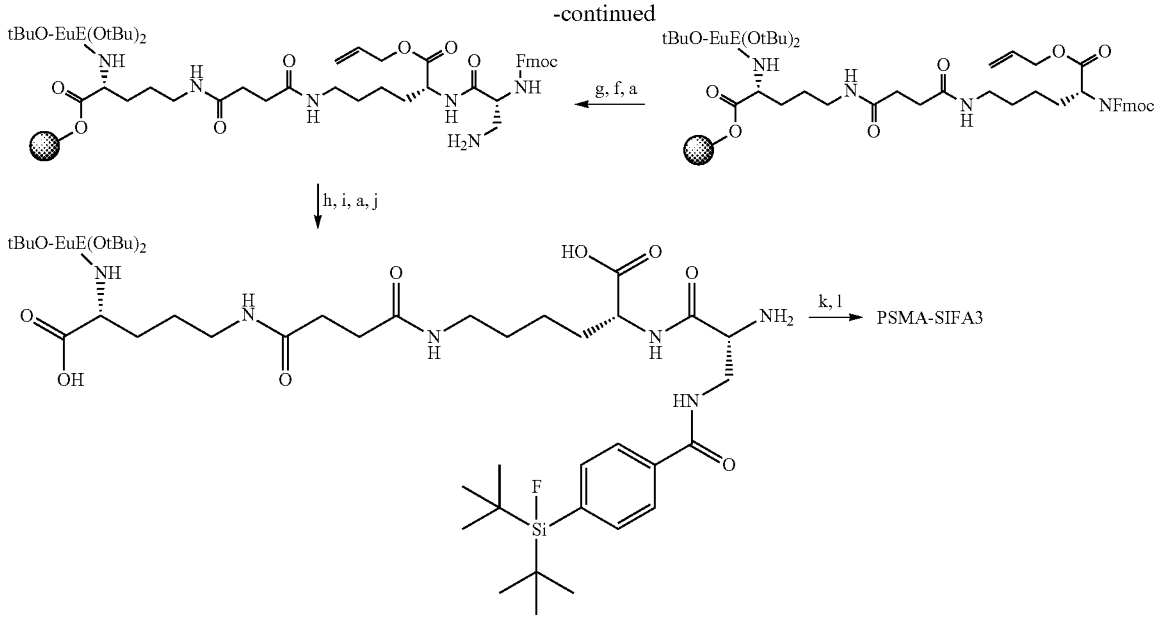

a) 20% piperidine, (DMF);
b) (tBuO)EuE(OtBu)$_2$, HOBt, TBTU, DIPEA, (DMF);
c) 2% hydrazine (DMF);
d) succinic anhydride, DIPEA, (DMF);
e) Fmoc-D-Lys-OAll-HCl, HOBt, TBTU, DIPEA, (DMF);
f) Fmoc-D-Dap(Dde)-OH, HOBt, TBTU, DIPEA, (DMF);
g) imidazole, hydroxylamine hydrochloride, (NMP, DMF);
h) SIFA-BA, HOBt, TBTU, DIPEA (DMF);
i) TIPS, Pd(PPh$_3$)$_4$, (DCM);
j) TFE, AcOH (DCM);
k) DOTAGA-anhydrid, DIPEA, (DMF);
l) TFA.

(8)

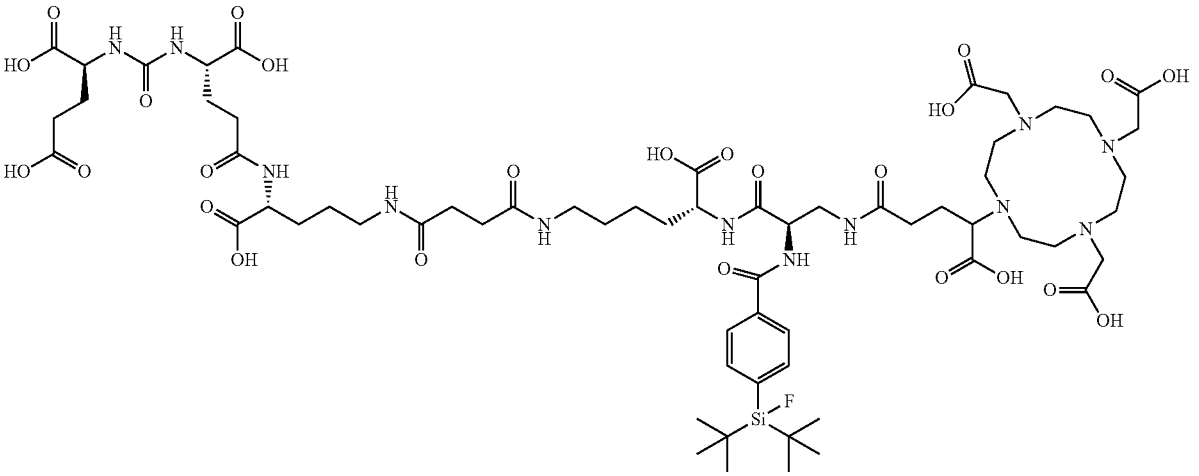

PSMA-SIFA4

PSMA-SIFA4 was synthesized through SPPS as compound 7, with one deviation; After conjugation of Fmoc-D-Dap (Dde)-OH, the Fmoc-protecting group was cleaved first with 20% piperidine in DMF and SIFA-BA was reacted with the free N-terminus of the peptide. The remaining Dde-group was cleaved after removing the allyloxy-protecting group by using imidazole and hydroxylamine hydrochloride dissolved in a mixture of NMP and DMF. Following reaction steps were identical to PSMA-SIFA3. After RP-HPLC purification, PSMA-SIFA4 (11%) was obtained as a colorless solid. HPLC (10 to 70% B in 15 min): $t_R$=10.4 min.

Calculated monoisotopic mass ($C_{63}H_{99}FN_{12}O_{25}Si$): 1470.7 found: m/z=1471.7 $[M+H]^+$, 736.8 $[M+2H]^{2+}$.

The peptide backbone of PSMA-SIFA5 was prepared analogously to ligand 7 and 8. A difference was the use of Scheme 4

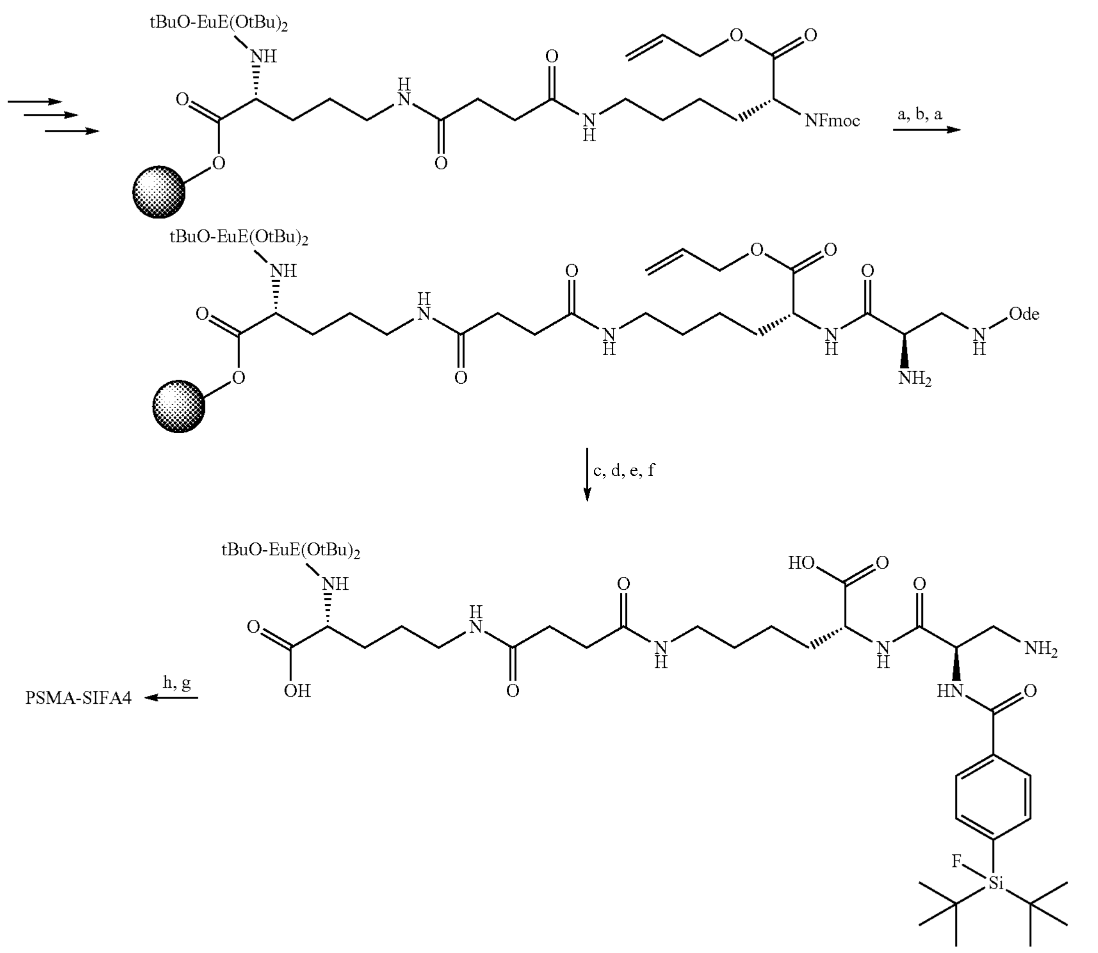

Synthesis of PSMA-SIFA4; a) 20% piperidine, (DMF); b) Fmoc-D-Dap(Dde)-OH, HOBt, TBTU, DIPEA, (DMF); c) SIFA-BA, HOBt, TBTU, DIPEA (DMF); d) TIPS Pd(PPh3)4, (DCM); e) imidazole, hydroxylamine hydrochloride, (NMP, DMF); f) TFE, AcOH (DCM); g) DOTAGA-anhydrid, DIPEA, (DMF); h) TFA.

(9)

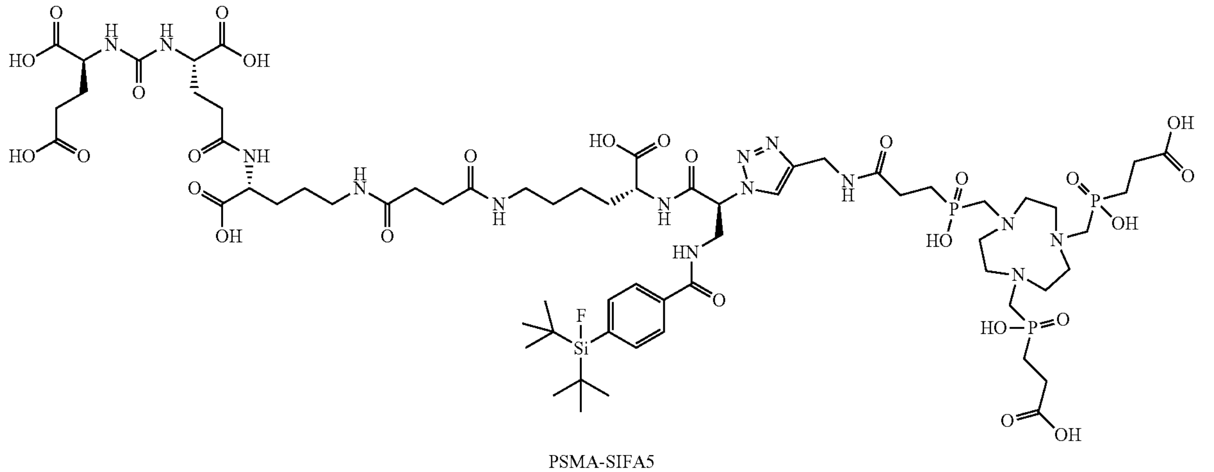

PSMA-SIFA5

$N_3$-L-Dap (Fmoc)-OH instead of Fmoc-D-Dap(Dde)-OH, which was required for the final click reaction with propargyl-TRAP. The azido-substituted amino acid (2.0 eq.) was conjugated with HATU (3.0 eq.), HOAt (3.0 eq.) and DIPEA (6.0 eq.) in DMF. After Fmoc-deprotection of its side chain with 20% piperidine, SIFA-BA (1.5 eq.) was reacted as mentioned above. Until conjugation of the chelator moiety, all remaining reaction steps were identical to peptide 7 and 8. After cleavage from the resin with TFA under concurrent deprotection of all acid labile protecting groups, the purified EuE-azido-conjugate (1.1 eq.) was reacted with propargyl-TRAP (1.0 eq.) in a copper(I)-catalyzed alkyne-azide cycloaddition. RP-HPLC purification yielded PSMA-SIFA5 (9%) as a colourless solid. HPLC (10 to 90% B in 15 min): $t_R$=8.7 min. Calculated monoisotopic mass ($C_{65}H_{106}FN_{14}O_{27}P_3Si$): 1654.6 found: m/z=1655.6 $[M+H]^+$, 828.4 $[M+2H]^{2+}$.

$^{nat}$Ga-PSMA-SIFA2: HPLC (10 to 90% B in 15 min): $t_R$=9.5 min. Calculated monoisotopic mass ($C_{65}H_{106}FGaN_{13}O_{24}P_3Si$): 1661.6 found: m/z=1663.9 $[M+H]^+$, 832.6 $[M+2H]^{2+}$.

$^{nat}$Ga-PSMA-SIFA5: HPLC (10 to 90% B in 15 min): $t_R$=9.0 min. Calculated monoisotopic mass ($C_{65}H_{103}FGaN_{14}O_{27}P_3Si$): 1720.5 found: m/z=1720.8 $[M+H]^+$, 861.1 $[M+2H]^{2+}$.

Synthesis of $^{nat}$Ga-DOTAGA complexes: 500 μL of a 2 mM stock solution of the PSMA precursor in DMSO was combined with 1500 μL of a 2 mM $Ga(NO_3)_3$ solution in water. The reaction mixture was heated for 30 min at 60° C. Outcome of the reaction was monitored by RP-HPLC and subsequent mass spectrometry. For radioactive labelling of [$^{nat}$Ga]PSMA-SIFA ligands with $^{18}F$, the complexed compound was purified by RP-HPLC before the labelling reaction.

Scheme 5

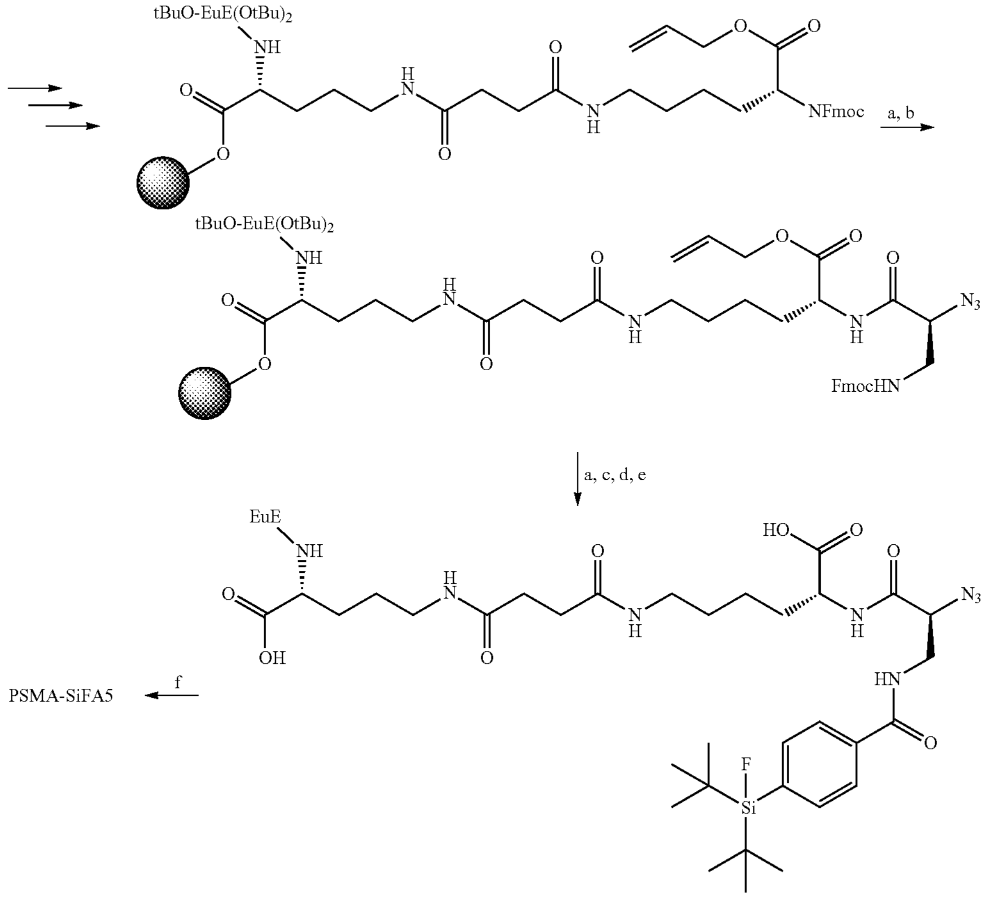

Synthesis of PSMA-SIFA5: a) 20% piperidine, (DMF); b) $N_3$-L-Dap(Fmoc)-OH, HOBt, TBTU, DIPEA, (DMF); c) SIFA-BA, HOBt, TBTU, DIPEA (DMF); d) TIPS $Pd(PPh_3)_4$, (DCM); e) TFA; (f) propargyl-TRAP, $Cu(OAc)_2$•$H_2O$, sodium ascorbate (tBuOH, $H_2O$).

Complexation Experiments

Synthesis of $^{nat}$Ga-TRAP complexes: 500 μL of a 2 mM stock solution of the PSMA precursor in DMSO was combined with 750 μL of a 2 mM $Ga(NO_3)_3$ solution in water. Complexation occurred instantaneously at room temperature. Completeness of the reaction was controlled by RP-HPLC and subsequent mass spectrometry.

$^{nat}$Ga-PSMA-SIFA1: HPLC (10 to 90% B in 15 min): $t_R$=9.1 min. Calculated monoisotopic mass ($C_{63}H_{99}FGaN_{11}O_{22}Si$): 1477.6 found: m/z=1479.5 $[M+H]^+$, 740.2 $[M+2H]^{2+}$.

$^{nat}$Ga-PSMA-SIFA3: HPLC (10 to 70% B in 15 min): $t_R$=10.4 min. Calculated monoisotopic mass ($C_{63}H_{96}FGaN_{12}O_{25}Si$): 1536.6 found: m/z=1539.4 $[M+H]^+$, 770.3 $[M+2H]^{2+}$.

$^{nat}$Ga-PSMA-SIFA4: HPLC (10 to 70% B in 15 min): HPLC (10 to 70% B in 15 min): $t_R$=10.4 min. Calculated monoisotopic mass ($C_{63}H_{96}FGaN_{12}O_{25}Si$): 1536.6 found: m/z=1539.1 $[M+H]^+$, 770.5 $[M+2H]^{2+}$.

$^{nat}$Lu-complexation: The corresponding $^{nat}Lu^{III}$-complexes were prepared from a 2 mM aqueous solution of the PSMA inhibitor with a 2.5 molar excess of $LuCl_3$ (20 mM solution), heated to 95° C. for 30 min. After cooling, the $^{nat}Lu^{III}$-chelate formation was confirmed using HPLC and MS. The resulting 1 mM aqueous solutions of the respective $^{nat}$Lu-complexes were then diluted and used in the in vitro $IC_{50}$ studies without further processing.

Radiolabelling $^{68}$Ga-labelling: $^{68}$Ga-labelling was done using an automated system (GallElut$^+$ by Scintomics, Germany) as described previously (Notni et al., EJNMMI research, 28 (2012)). Briefly, the $^{68}Ge/^{68}Ga$-generator with $SnO_2$ matrix (IThemba LABS) was eluted with 1.0 M aqueous HCl, from which a fraction (1.25 mL) of approximately 80% of the activity (500-700 MBq), was transferred into a reaction vial (ALLTECH, 5 mL). The reactor was loaded before elution with 2-5 nmol of respective chelator conjugate in an aqueous 2.7 M HEPES solution (DOTAGA-conjugates: 900 μL, TRAP-conjugates: 400 μL). After elution the vial was heated for 5 minutes at 95° C. Purification was done by passing the reaction mixture over a solid phase extraction cartridge (C 8 light, SepPak), which was purged with water (10 mL) and the product eluted with 50% aqueous ethanol (2 mL), phosphate buffered saline (PBS, 1 mL) and again water (1 mL). After removing ethanol in vacuo, purity of the radiolabelled compounds was determined by radio-TLC (ITLC-SG chromatography paper, mobile phase: 0.1 M trisodium citrate and 1:1 mixture (v/v) of 1 M ammonium acetate and methanol).

$^{18}$F-labelling: For $^{18}$F-labelling a previously published procedure (Wangler et al., Nat Protoc 7, 1946-55 (2012)). was applied, which was slightly modified. Briefly, aqueous $^{18}F^-$ was passed through a SAX cartridge (Sep-Pak Accell Plus QMA Carbonate light), which was preconditioned with 10 ml of water. After drying with 10 ml of air, water was removed, by rinsing the cartridge with 10 mL of anhydrous acetonitrile followed by 20 ml of air. $^{18}$F was eluted with 100 μmol of $[K^+ \subset 2.2.2]OH^-$ dissolved in 500 μL of anhydrous acetonitrile. Before labelling, 25 μmol of oxalic acid in anhydrous acetonitrile (1 M, 25 μL) were added. This mixture was used as a whole or aliquot for fluorination of 10-25 μmol of PSMA-SIFA (1 M in anhydrous DMSO). The resulting reaction mixture was incubated for 5 minutes at room temperature. For purification of the tracer, a Sep-Pak C18 light cartridge, preconditioned with 10 mL EtOH, followed by 10 mL of $H_2O$ was used. The labelling mixture was diluted with 9 mL 0.1 M HEPES buffer (pH 3) and passed through the cartridge followed by 10 ml of $H_2O$. The peptide was eluted with 500 μL of a 4:1 mixture (v/v) of EtOH in water. Radiochemical purity of the labelled compound was determined by radio RP-HPLC and radio-TLC (Silica gel 60 RP-18 $F_{254}$S, mobile phase: 3:2 mixture (v/v) of MeCN in $H_2O$ supplemented with 10% of 2 M NaOAc solution and 1% of TFA).

$^{125}$I-labelling: The reference ligand for in vitro studies ($[^{125}I]$I-BA) KuE was prepared according to a previously published procedure (Weineisen et al., EJNMMI research, 4, 63 (2014)). Briefly, 0.1 mg of the stannylated precursor ($SnBu_3$-BA)(OtBu)KuE$(OtBu)_2$ was dissolved in a solution containing 20 μL peracetic acid, 5.0 μL (21 MBq) $[^{125}I]$NaI (74 TBq/mmol, 3.1 GBq/mL, 40 mM NaOH, Hartmann Analytic, Braunschweig, Germany), 20 μL MeCN and 10 μL acetic acid. The reaction solution was incubated for 10 min at RT, loaded on a cartridge and rinsed with 10 mL water (C18 Sep Pak Plus cartridge, preconditioned with 10 mL MeOH and 10 mL water). After elution with 2.0 mL of a 1:1 mix (v/v) of EtOH/MeCN, the radioactive solution was evaporated to dryness under a gentle nitrogen stream and treated with 200 μL TFA for 30 min with subsequent evaporation of TFA. The crude product of ($[^{125}I]$I-BA) KuE was purified by RP-HPLC (20% to 40% B in 20 min): $t_R$=13.0 min.

$^{177}$Lu-labeling: To a reaction volume of 10 μL 1.0 M $NH_4OAc$ buffer pH=5.9 was added 0.75 to 1.0 nmol tracer (7.5 to 10 μL), 10 to 40 MBq $^{177}LuCl_3$ (Specific Activity ($A_s$)>3000 GBq/mg, 740 MBq/mL, 0.04 M HCl, ITG, Garching, Germany) and finally filled up to 100 μL with trace-pure Water (Merck, Darmstadt, Germany). The reaction mixture was heated for 30 min at 95° C. and the radiochemical purity was determined using radio-TLC (Silica gel 60 RP-18 $F_{254}$S, 3:2 mixture (v/v) of MeCN in $H_2O$ supplemented with 10% of 2 M NaOAc solution and 1% of TFA, $R_f$=0.5).

In Vitro Experiments

Determination of $IC_{50}$

The PSMA-posivite LNCaP cells were grown in Dublecco modified Eagle medium/Nutrition Mixture F-12 with Glutamax-I (1:1) (Invitrigon), supplemented with 10% fetal calf serum and maintained at 37° C. in a humidified 5% $CO_2$ atmosphere. For determination of the PSMA affinity ($IC_{50}$), cells were harvested 24±2 hours before the experiment and seeded in 24-well plates ($1.5 \times 10^5$ cells in 1 mL/well). After removal of the culture medium, the cells were treated once with 500 μL of HBSS (Hank's balanced salt solution, Biochrom, Berlin, Germany, with addition of 1% bovine serum albumin (BSA)) and left 15 min on ice for equilibration in 200 μL HBSS (1% BSA). Next, 25 μL per well of solutions, containing either HBSS (1% BSA, control) or the respective ligand in increasing concentration ($10^{-10}$-$10^{-4}$ M in HBSS, were added with subsequent addition of 25 μL of ($[^{125}I]$I-BA) KuE (2.0 nM) in HBSS (1% BSA). All experiments were performed at least three times for each concentration. After 60 min incubation on ice, the experiment was terminated by removal of the medium and consecutive rinsing with 200 μL of HBSS. The media of both steps were combined in one fraction and represent the amount of free radioligand. Afterwards, the cells were lysed with 250 μL of 1 M NaOH and united with the 200 μL HBSS of the following wash step. Quantification of bound and free radioligand was accomplished in a γ-counter.

Internalization

For internalization studies, LNCaP cells were harvested 24±2 hours before the experiment and seeded in 24-well plates ($1.25 \times 10^5$ cells in 1 mL/well). Subsequent to the removal of the culture medium, the cells were washed once with 500 μL DMEM-F12 (5% BSA) and left to equilibrate for at least 15 min at 37° C. in 200 μL DMEM-F12 (5% BSA). Each well was treated with either 25 μL of either DMEM-F12 (5% BSA) or a 100 μM PMPA solution for blockade. Next, 25 μL of the $^{68}Ga/^{18}F$-labelled PSMA inhibitor (5.0 nM) was added and the cells incubated at 37° C. for 60 min. The experiment was terminated by placing the 24-well plate on ice for 3 min and consecutive removal of the medium. Each well was rinsed with 250 μL HBSS and the fractions from these first two steps combined, representing the amount of free radioligand. Removal of surface bound activity was accomplished by incubation of the cells with 250 μL of ice-cold PMPA (10 μM in PBS) solution for 5 min and rinsed again with another 250 μL of ice-cold PBS.

The internalized activity was determined by incubation of the cells in 250 μL 1 M NaOH and the combination with the fraction of a subsequent wash step with 250 μL 1.0 M NaOH. Each experiment (control and blockade) was performed in triplicate. Free, surface bound and internalized activity was quantified in a γ-counter. All internalization studies were accompanied by reference studies using ([$^{125}$I]I-BA) KuE (c=0.2 nM), which were performed analogously. Data were corrected for non-specific internalization and normalized to the specific-internalization observed for the radioiodinated reference compound.

Octanol-Water Partition Coefficient

Approximately 1 MBq of the labelled tracer was dissolved in 1 mL of a 1:1 mixture (by volumes) of phosphate buffered saline (PBS, pH 7.4) and n-octanol in an Eppendorf tube. After vigorous mixing of the suspension for 3 minutes at room temperature, the vial was centrifuged at 15000 g for 3 minutes (Biofuge 15, Heraus Sepatech, Osterode, Germany) and 100 μL aliquots of both layers were measured in a gamma counter. The experiment was repeated at least six times.

HSA Binding

For the determination of HSA binding, a Chiralpak HSA column (50×3 mm, 5 μm, H13H-2433) was used at a constant flow rate of 0.5 mL/min. The mobile phase (A: $NH_4OAc$, 50 mM in water, pH 7 and B: isopropanol) was freshly prepared for each experiment and only used for one day. The column was kept at room temperature and each run was stopped after detection of the signal to reduce the acquisition time. All substances were dissolved in a 0.5 mg/ml concentration in 50% 2-propanol and 50% 50 mM pH 6.9 ammonium acetate buffer. The chosen reference substances display a range of HSA binding from 13% to 99% since a broad variety of albumin binding regarding the peptides was assumed. All nine reference substances (see Table 1) were injected consecutively to establish a non-linear regression with OriginPro 2016G; see FIG. 1.

TABLE 1

Reference substances (Yamazaki et al., Journal of pharmaceutical sciences 93, 1480-94 (2004)) used for the calibration of the HSA-column.

| Reference | $t_R$ | Log $t_R$ | Lit. HSA % | Log K HSA |
|---|---|---|---|---|
| p-benzyl alcohol | 2.40 | 0.38 | 13.15 | −0.82 |
| Aniline | 2.72 | 0.43 | 14.06 | −0.79 |
| Phenol | 3.28 | 0.52 | 20.69 | −0.59 |
| Benzoic Acid | 4.08 | 0.61 | 34.27 | −0.29 |
| Carbamazepine | 4.15 | 0.62 | 75.00 | 0.46 |
| p-nitrophenol | 5.62 | 0.75 | 77.65 | 0.52 |
| Estradiol | 8.15 | 0.91 | 94.81 | 1.19 |
| Probenecid | 8.84 | 0.95 | 95.00 | 1.20 |
| Glibenclamide | 29.18 | 1.47 | 99.00 | 1.69 |

The retention time is shown exemplary for a conducted experiment; $t_R$ retention time; Lit. HSA literature value of human serum albumin binding in [%]; Log K HAS logarithmic K of human serum albumin binding.

In Vivo Experiments

All animal experiments were conducted in accordance with general animal welfare regulations in Germany and the institutional guidelines for the care and use of animals. To establish tumor xenografts, LNCaP cells ($10^7$ cells/200 μL) were suspended in a 1:1 mixture (v/v) of Dulbecco modified Eagle medium/Nutrition Mixture F-12 with Glutamax-I (1:1) and Matrigel (BD Biosciences, Germany), and inoculated subcutaneously onto the right shoulder of 6-8 weeks old CB17-SCID mice (Charles River, Sulzfeld, Germany). Mice were used for when tumors had grown to a diameter of 5-8 mm (3-4 weeks after inoculation).

μPET Imaging

Imaging studies were performed at a Siemens Inveon small-animal PET system. Data were reconstructed as single frames employing a three-dimensional ordered subset expectation maximum (OSEM3D) algorithm, followed by data analysis (ROI-based quantification) using Inveon Research Workplace software. For PET studies mice were anesthetized with isoflurane and injected with 0.15-0.25 nmol (2-20 MBq) of the $^{68}$Ga or $^{18}$F-labelled tracer into the tail vein. Dynamic imaging was performed after on-bed injection for 90 minutes. Static images were recorded one hour after the injection with an acquisition time of 15 minutes. For blockade 8 mg/kg of PMPA was administered directly before tracer injection.

Biodistribution

Approximately 2-20 MBq (0.2 nmol) of the $^{68}$Ga or $^{18}$F-labelled PSMA inhibitors were injected into the tail vein of LNCaP tumor-bearing male CB-17 SCID mice and sacrificed after 1 h post injection (n=3). Selected organs were removed, weighted and measured in a γ-counter.

In Human Experiments

A proof-of-concept evaluation of use in humans was conducted under compassionate use. The agent was applied in compliance with The German Medicinal Products Act, AMG § 13 2b, and in accordance with the responsible regulatory body (Government of Oberbayern).

All subjects were examined on a Biograph mCT scanner (Siemens Medical Solutions, Erlangen, Germany) or a Biograph mMR scanner (Siemens Medical Solutions, Erlangen, Germany). All PET scans were acquired in 3D-mode with an acquisition time of 2-4 min per bed position. Emission data were corrected for randoms, dead time, scatter, and attenuation and were reconstructed iteratively by an ordered-subsets expectation maximization algorithm (four iterations, eight subsets) followed by a postreconstruction smoothing Gaussian filter (5-mm full width at one-half maximum). Images in 53 subjects with prostate cancer were obtained after injection of a mean of 324 (range 236-424) MBq 18F-labelled PSMA-SIFA3 (7) at a mean of 84 (range 42-166) min post injection. 47 subjects underwent imaging on a PET/CT, 6 subjects on a PET/MR scanner. In 33 subjects furosemide was applied at the time of tracer injection, in 20 subjects no furosemide was given.

The mean and maximum standardized uptake values (SUVmean/SUVmax) of parotid glands, submandibular glands, lungs, mediastinal blood pool, liver, spleen, pancreas head, duodenum, kidneys, bladder and non-diseased bone were analysed. For calculation of the SUV, circular regions of interest were drawn around areas with focally increased uptake in transaxial slices and automatically adapted to a three-dimensional volume of interest (VOI) at a 50% isocontour. Lesions that were visually considered as suggestive of relapses or metastases of prostate cancer were counted. One or two lesions from the same type (local tumor, lymph node metastases, bone metastases, visceral metastases) were analysed per patient using SUVmax and SUVmean as described above. Gluteal muscle served as background.

EXAMPLE 2: RESULTS
Overview of the Synthesised PSMA-SIFA Ligands
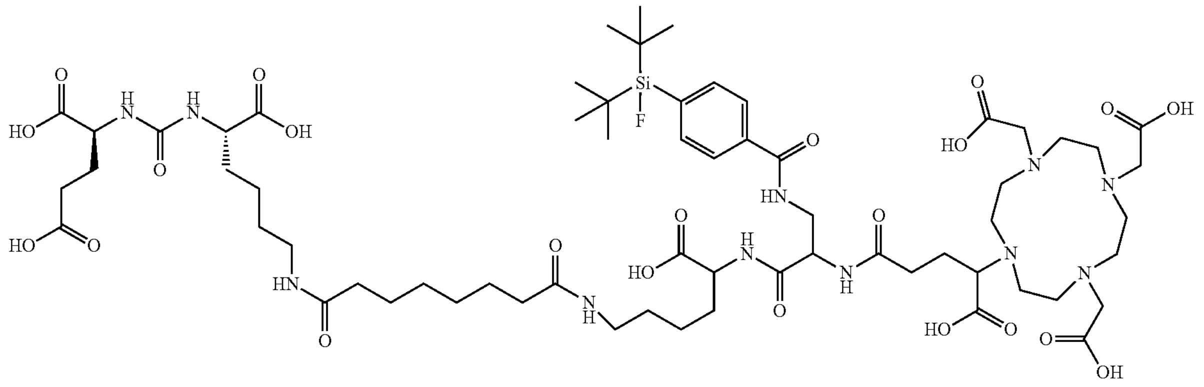
PSMA-SIFA1 (5)
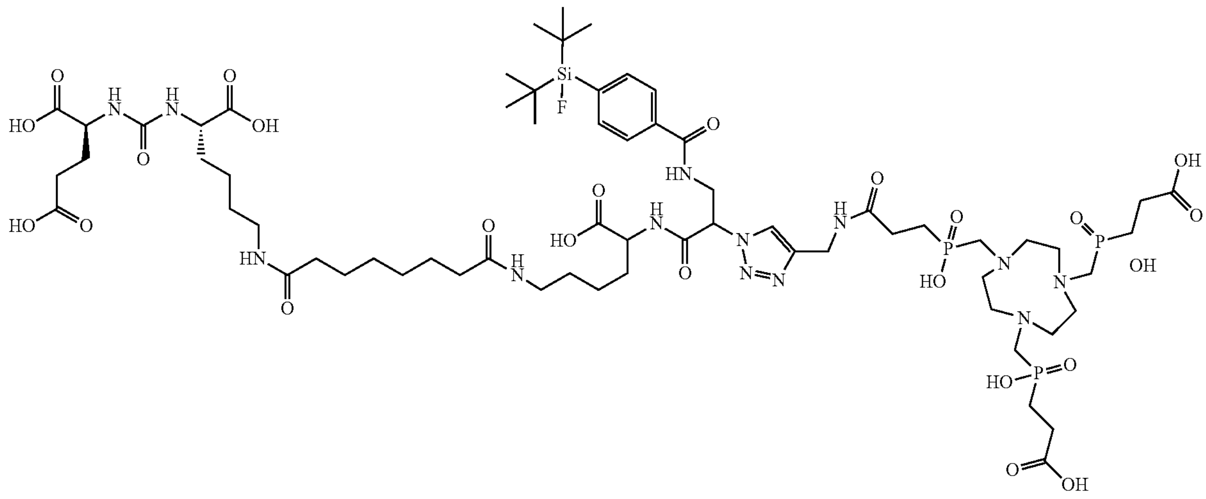
PSMA-SIFA2 (6)
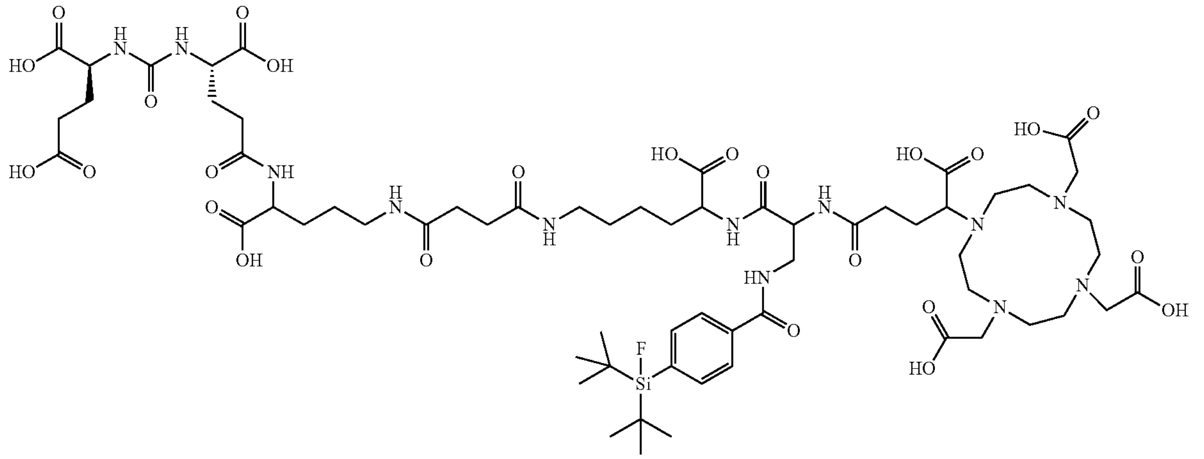
PSMA-SIFA3 (7)

-continued
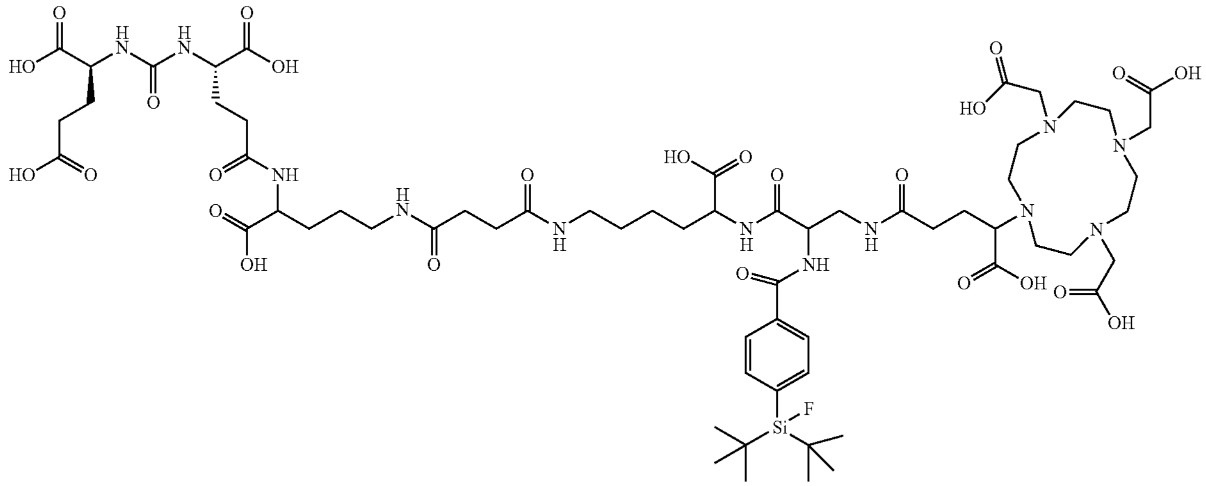
PSMA-SIFA4 (8)
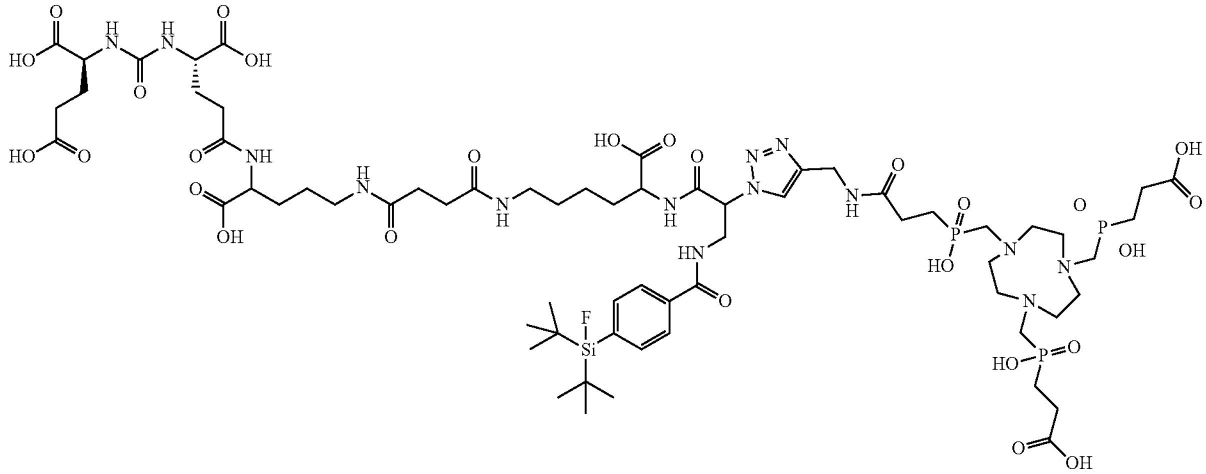
PSMA-SIFA5 (9)
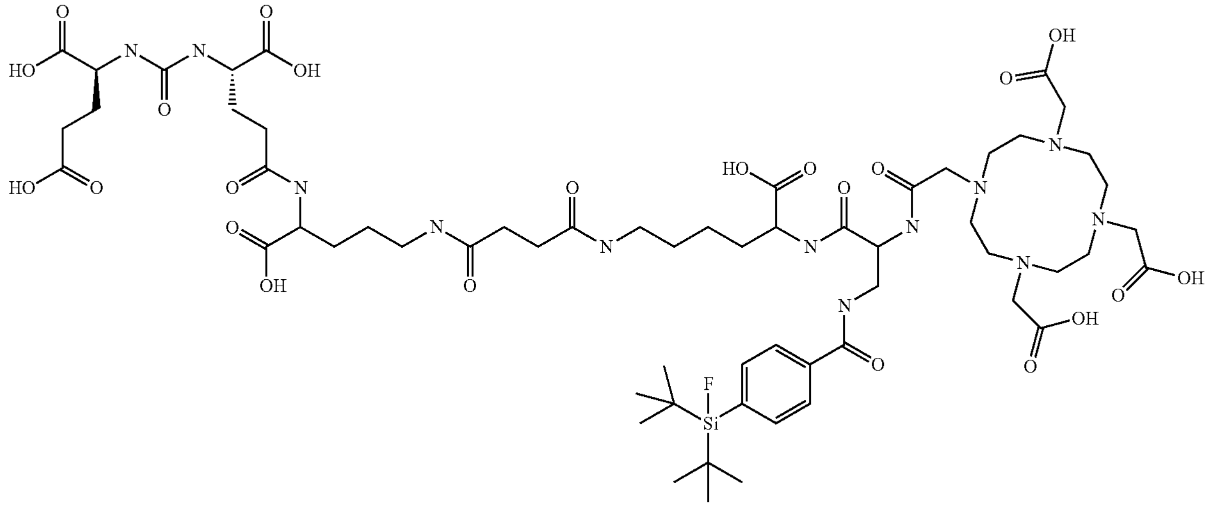
PSMA-SIFA 10

-continued

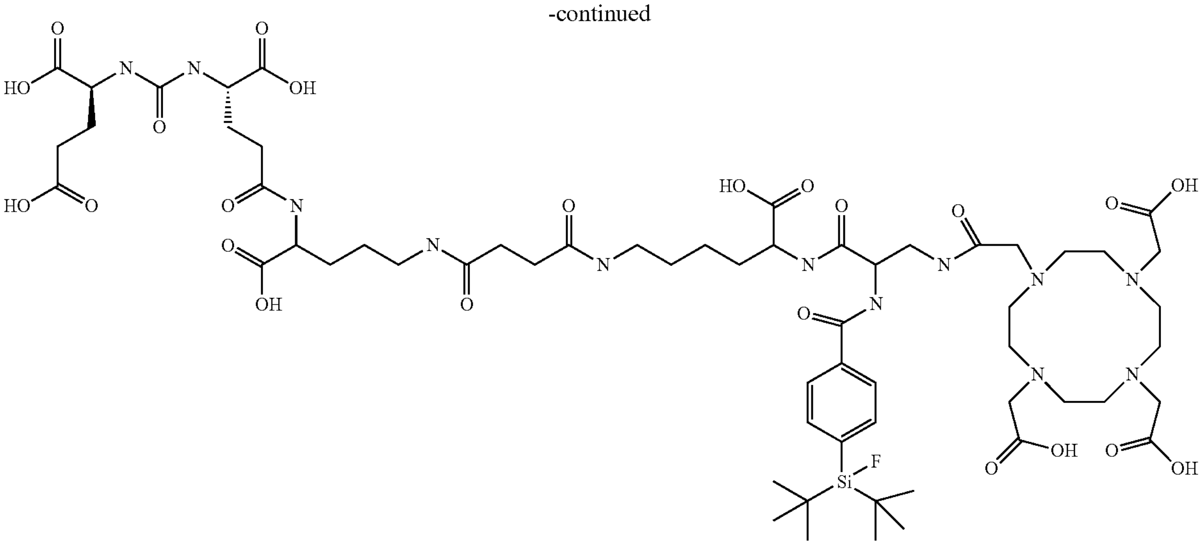

PSMA-SIFA 11

Lipophilicities

The determined octanol/water partition coefficients (log D) of the $^{68}$Ga- or $^{18}$F-labelled compounds are presented in Table 2. Within the $^{68}$Ga-labelled EuK-based inhibitors, the TRAP-functionalized compound (5), was found to be more hydrophilic than 6, where DOTAGA was used as a chelator. This result was also found for the $^{68}$Ga-labelled EuE-based agents, where the TRAP-derivative (9) showed the highest lipophilicity. All of the $^{18}$F-labelled compounds showed lower hydrophilicities, compared to the $^{68}$Ga-labelled tracers.

TABLE 2 log D values of the synthesized radiolabelled PSMA-SIFA ligands (n = 6).

| ligand | log D $^{68}$Ga-$^{nat}$F-L | log D $^{18}$F-L | log D $^{177}$Lu-$^{nat}$F-L |
|---|---|---|---|
| 5 | −2.75 ± 0.07 | nd. | |
| 6 | −3.00 ± 0.09 | n.d. | |
| 7 | −3.18 ± 0.05 | −1.98 ± 0.04 | −4.20 ± 0.09 |
| 8 | −2.59 ± 0.04 | −2.25 ± 0.07 | −3.75 ± 0.06 |
| 9 | −3.26 ± 0.06 | −2.23 ± 0.07 | |
| 10 | | | −3.59 ± 0.05 |
| 11 | | | −3.62 ± 0.06 |

Determination of PSMA Affinities

The synthesized compounds bearing a EuE-binding motif (7, 8, 9) showed higher PSMA affinities compared to the EuK-based agents (5, 6). Compounds with a TRAP-chelator (6 and 9) showed slightly decreased affinities, compared to their DOTAGA analogues (5 and 7, respectively). Between the $^{nat}$Ga-complexed agents and the respective uncomplexed compound no significant difference was observed regarding PSMA affinities (Table 3).

TABLE 3

Binding affinities ($IC_{50}$ in nM) of the PSMA-SIFA ligands to PSMA. Affinities were determined using LNCaP cells (150000 cells/well) and ([$^{125}$I]I-BA)KuE (c = 0.2 nM) as the radioligand (1 h, 4° C., HBSS + 1% BSA). Data are expressed as mean ± SD (n = 3, in 3 different experiments).

| ligand | $IC_{50}$ [nM] $^{nat}$Ga-$^{nat}$F-L | $IC_{50}$ [nM] $^{nat}$F-L | $IC_{50}$ [nM] $^{nat}$Lu-$^{nat}$F-L |
|---|---|---|---|
| 5 | 7.3 ± 0.2 | 6.4 ± 0.2 | |
| 6 | 10.8 ± 2.5 | 8.5 ± 1.7 | |
| 7 | 3.0 ± 0.7 | 3.5 ± 0.2 | 3.9 ± 0.5 |
| 8 | 3.8 ± 0.7 | 2.5 ± 0.2 | 3.0 ± 0.2 |
| 9 | 4.5 ± 0.3 | 4.3 ± 0.2 | |
| 10 | | | 2.8 ± 0.7 |
| 11 | | | 4.8 ± 0.7 |

references:
(I-BA)KuE $IC_{50}$ = 7.1 ± 2.4 nM
DCFPyL $IC_{50}$ = 12.3 ± 1.2 nM
PSMA-1007 $IC_{50}$ = 4.2 ± 0.5 nM Internalization In analogy to the binding affinities, EuE-based compounds (7, 8, 9) showed significant higher internalization values compared to peptides bearing a EuK-binding motif (5, 6). Regarding the influence of the chelator, TRAP showed to have a positive effect on internalization (5 and 9, compared to 6 and 7 respectively), even though binding affinities where higher for the DOTAGA analogues (Table 3). All of the $^{18}$F-labelled compounds showed higher internalization values, compared to the respective $^{88}$Ga-labelled tracers (Table 4).

TABLE 4

Summary of the internalized activity (c = 0.5 nM) at 1 hour as % of the reference ligand ([$^{125}$I]I-BA)KuE (c = 0.2 nM), determined on LNCaP cells (37° C., DMEM F12 + 5% BSA, 125000 cells/well). Data is corrected for non-specific binding (10 μmol PMPA) and expressed as mean ± SD (n = 3).

| ligand | Internalization [%] $^{68}$Ga-$^{nat}$F-L | Internalization [%] $^{18}$F-L | Internalization [%] $^{177}$Lu-$^{nat}$F-L |
|---|---|---|---|
| 5 | 33.0 ± 2.1 | n.d. | |
| 6 | 43.0 ± 3.4 | n.d. | |

TABLE 4-continued

Summary of the internalized activity (c = 0.5 nM) at 1 hour as % of the reference ligand ([$^{125}$I]I-BA)KuE (c = 0.2 nM), determined on LNCaP cells (37° C., DMEM F12 + 5% BSA, 125000 cells/well). Data is corrected for non-specific binding (10 μmol PMPA) and expressed as mean ± SD (n = 3).

| ligand | Internalization [%] $^{68}$Ga-$^{nat}$F-L | Internalization [%] $^{18}$F-L | Internalization [%] $^{177}$Lu-$^{nat}$F-L |
|---|---|---|---|
| 7 | 126.0 ± 13.1 | 164.8 ± 4.5 | 185.8 ± 4.5 |
| 8 | 98.2 ± 12.4 | 130.3 ± 5.5 | 165.9 ± 8.5 |
| 9 | 176.9 ± 11.7 | 211.6 ± 5.3 | |
| 10 | | | 184.1 ± 16 |
| 11 | | | 134.5 ± 18.5 |

references:
DCFPyL 118 ± 5
[%] PSMA-1007 118 ± 4

Human Serum Albumin Binding

TABLE 5

HSA binding of the synthesized PSMA-SIFA ligands, determined on a Chiralpak HSA column (50 × 3 mm, 5 μm, H13H-2433).

| ligand | HSA binding [%] $^{nat}$Ga-$^{nat}$F-L | HSA binding [%] $^{nat}$Lu-$^{nat}$F-L |
|---|---|---|
| 7 | 95.7 | 97.7 |
| 8 | 96.5 | 97.7 |
| 9 | 95.1 | |
| 10 | | 94.0 |
| 11 | | 92.4 |

Small Animal PET Imaging and Biodistribution

1. [$^{68}$Ga][$^{nat}$F]PSMA-SIFA1 ($^{68}$Ga-$^{nat}$F-5)
   See FIG. 2.
2. [$^{68}$Ga][$^{nat}$F]PSMA-SIFA2 ($^{68}$Ga-$^{nat}$F-6)
   See FIG. 3.
3. PSMA-SIFA3 (7)
   a) static $^{68}$Ga-PET imaging
   See FIG. 4.
   b) dynamic $^{68}$Ga-PET imaging
   See FIG. 5.
   c) static $^{18}$F-PET imaging
   See FIG. 6.
   d) dynamic $^{18}$F-PET imaging
   See FIG. 7.
   e) biodistribution studies
   See FIG. 8.
4. PSMA-SIFA4 (8)
   a) static $^{68}$Ga-PET imaging
   See FIG. 9.
   b) dynamic $^{68}$Ga-PET imaging
   See FIG. 10.
   c) static $^{18}$F-PET imaging
   See FIG. 11.
   d) dynamic $^{18}$F-PET imaging
   See FIG. 12.
   e) biodistribution studies
   See FIG. 13.
5. PSMA-SIFA5 (9)
   a) static $^{68}$Ga-PET imaging
   See FIG. 14.
   b) dynamic $^{68}$Ga-PET imaging
   See FIG. 15.
   c) static $^{18}$F-PET imaging
   See FIG. 16.
   d) static $^{18}$F-PET imaging
   See FIG. 17.
   e) biodistribution studies
   See FIG. 18.
6. Proof of Concept studies of $^{nat}$Ga-PSMA-SIFA3 ($^{nat}$Ga-7)
   a) static $^{18}$F-PET imaging
   See FIG. 19.
   b) biodistribution studies
   See FIG. 20.
7. Small animal PET imaging using Luthenium rhPSMA ligands.
   a) Static PET imaging: $^{18}$F-$^{nat}$Lu-rh-7
   See FIG. 29.
   b) Dynamic PET imaging: $^{18}$F-$^{nat}$Lu-rh7
   See FIG. 30.
   c) biodistribution studies of $^{177}$Lu-$^{nat}$F-7, $^{177}$Lu-$^{nat}$F-8 and $^{177}$Lu-$^{nat}$F-10 at 24 h
   See FIG. 31.
   d) biodistribution of $^{177}$Lu-$^{nat}$F-10 at 1 h and 24 h.
   See FIG. 32.
   e) Comparative biodistribution of established and new rhPSMA-ligands at 24 h.
   See FIG. 33.
   f) Comparative biodistribution of $^{177}$Lu-$^{nat}$F-rhPSMA-10 and $^{68}$Ga-$^{nat}$F-rhPSMA-10 at 1 h.
   See FIG. 34.

Human PSMA-SIFA3 (7) Biodistribution and Uptake in Tumor Lesions

No adverse events or clinically detectable pharmacological effects were noted.

FIG. 21 demonstrates the maximum intensity projection (MIR) from PET of a subject with normal biodistribution (no tumor lesions detectable). Images were acquired 76 min post injection of 272 MBq 18F-labelled PSMA-SIFA3 (7). FIG. 21 right demonstrates the maximum intensity projection (MIP) from PET of a subject with moderately advanced disease exhibiting multiple tumor lesions with high lesion-to-background ratio. Images were acquired 102 min post injection of 312 MBq 18F-labelled PSMA-SIFA3 (7).

Uptake parameters reflect background PSMA-expression for different tissue types. Significant radiotracer uptake was only discerned for salivary glands, kidneys, liver, spleen and duodenum. Uptake in background tissue was low. Uptake in tumor lesion was substantially higher than in low PSMA-expressing tissue.

TABLE 6

Average SUVmax (left) and SUVmean (right) in different tissues (tissues/organs: n = 53, tumor lesions: n = 72) with its standard error. See FIG. 22 for graphical representation.

| | SUVmax | | | SUVmean | | |
|---|---|---|---|---|---|---|
| | mean | min | max | mean | min | max |
| background | 1.0 | 0.6 | 1.9 | 0.6 | 0.4 | 1.2 |
| bloodpool | 2.4 | 1.6 | 3.9 | 2.0 | 1.1 | 17.0 |
| parotid gland | 23.5 | 8.2 | 42.3 | 16.8 | 5.5 | 32.7 |
| submandibular gland | 26.7 | 10.1 | 43.8 | 19.6 | 7.0 | 29.7 |
| lungs | 1.0 | 0.5 | 3.1 | 0.7 | 0.3 | 2.0 |
| liver | 9.5 | 4.5 | 25.2 | 7.0 | 3.2 | 17.7 |
| spleen | 11.8 | 4.7 | 21 | 9.1 | 3.4 | 17.1 |
| pancreas | 3.9 | 1.8 | 9.2 | 2.7 | 1.3 | 7.4 |
| duodenum | 14.2 | 2.8 | 32.7 | 10.5 | 1.9 | 23.9 |
| bone | 1.7 | 0.8 | 3.1 | 1.1 | 0.6 | 2.1 |
| kidney | 44.3 | 19.1 | 75.2 | 32.1 | 13.2 | 54.7 |
| bladder | 8.3 | 0.5 | 112.0 | 6.1 | 0.3 | 85.7 |
| tumor lesions | 28.6 | 4.0 | 95.4 | 19.2 | 2.7 | 71.7 |

Due to low background activity ratio SUV to background of organs and tumor lesions is favorable for clinical imaging. Tumor lesions are displayed with high contrast compared to background.

TABLE 7

Average ratio SUVmax (left) and SUVmean (right) with its standard error in different tissues (tissues/organs: n = 53, tumor lesions: n = 72) with its standard error. See FIG. 23 for graphical representation.

| | ratio SUVmax to background | | | ratio SUVmean to background | | |
|---|---|---|---|---|---|---|
| | mean | min | max | mean | min | max |
| bloodpool | 2.5 | 1.3 | 4.8 | 3.1 | 1.5 | 21.3 |
| parotid gland | 24.3 | 8.2 | 45.3 | 27.5 | 9.2 | 54.5 |
| submandibular gland | 27.8 | 10.1 | 54.7 | 32.5 | 11.7 | 61.8 |
| lungs | 1.1 | 0.4 | 3.3 | 1.1 | 0.4 | 4.0 |
| liver | 10.1 | 2.9 | 42.0 | 11.7 | 3.7 | 44.3 |
| spleen | 12.3 | 4.7 | 35.0 | 14.9 | 5.7 | 39.5 |
| pancreas | 4.0 | 1.5 | 11.3 | 4.3 | 1.9 | 10.8 |
| duodenum | 14.8 | 2.8 | 31.3 | 17.3 | 3.2 | 35.3 |
| bone | 1.7 | 0.9 | 2.9 | 1.8 | 1.0 | 3.2 |
| kidney | 46.7 | 16.9 | 96.7 | 53.8 | 19.8 | 109.3 |
| bladder | 8.3 | 0.6 | 112.0 | 9.8 | 0.5 | 142.8 |
| tumor lesions | 28.6 | 5.0 | 83.4 | 31.9 | 5.4 | 83.2 |

Uptake in tumor lesions and contrast to background was relatively equal between different types of tumors (local tumor [n=24], lymph node metastases [n=23], bone metastases [n=21], visceral metastases [n=4]).

TABLE 8

Average SUVmax, SUVmean, ratio SUVmax to background and ratio SUVmean to background in different tumor types with its standard error. See FIG. 24 for a graphical representation.

| | | SUVmax | ratio SUVmax | SUVmean | ratio SUVmean |
|---|---|---|---|---|---|
| local tumor | mean | 26.9 | 29.6 | 19.3 | 32.4 |
| | min | 4 | 5 | 2.7 | 5.4 |
| | max | 75.1 | 83.4 | 19.3 | 83.2 |
| LN | mean | 22.2 | 23.7 | 16.6 | 27.3 |
| | min | 8.1 | 5.8 | 6.4 | 7.1 |
| | max | 67.5 | 63.6 | 44.6 | 70.7 |
| bone | mean | 31.2 | 32.8 | 22.2 | 36.6 |
| | min | 7.9 | 7.9 | 5.3 | 8.8 |
| | max | 95.4 | 73.4 | 71.7 | 80 |
| visceral | mean | 26.1 | 28.9 | 17.4 | 30.2 |
| | min | 20.4 | 18.5 | 15.5 | 22.1 |
| | max | 32.5 | 40.6 | 19.1 | 38.2 |

Human PSMA-SIFA3 (7) Tracer Retention in Urinary Bladder

Tracer retention in excretory urinary system is a common drawback of PSMA-ligand imaging. 18F-labelled PSMA-SIFA3 (7) as potential lead compound of SiFA substituted chelator-based PET agent is excreted via the urinary excretory system, but to a much lower extent than most other PET-agents. In addition, its retention in the bladder can be significantly influenced by the application of furosemide at the time of tracer injection. T-test 8 revealed a statistical significantly lower tracer retention when furosemide was applied (p=0.018 both for SUVmax and SUVmean).

TABLE 9

Average SUVmax (left) and SUVmean (right) of tracer retention in bladder in subjects with and without administration of furosemide with its standard error. See FIG. 25 for graphical representation.

| | SUVmax | | | SUVmean | | |
|---|---|---|---|---|---|---|
| | mean | min | max | mean | min | max |
| with furosemide | 4.8 | 1.6 | 32 | 3.4 | 1.1 | 26.6 |
| without furosemide | 13.9 | 0.5 | 112 | 10.5 | 0.3 | 85.7 |

Clinical Results for PSMA-SIFA3 (7) Detection of Tumor Lesions and Histopathological Validation Subjects were imaged for primary staging (n=6) and recurrent disease (n=47). Lesions indicative for prostate cancer were detected in 39 patients. 72 lesions were analysed. 21 of 72 lesions had no correlate on morphological imaging. 14 of 72 lesions measured exhibited a size of equal or less than 5 mm on morphological imaging. Both demonstrate high clinical value of 18F-labelled PSMA-SIFA3 (7) for detection of lesions otherwise occult on morphological imaging. Uptake parameters of the 35 lesions with no correlate or small size on morphological imaging exhibited favorable uptake parameters.

TABLE 10

Average SUVmax, SUVmean, ratio SUVmax to background and ratio SUVmean to background in prostate cancer tumors with its standard error.

| | SUVmax | ratio SUVmax | SUVmean | ratio SUVmean |
|---|---|---|---|---|
| mean | 16.7 | 18.3 | 13.3 | 22.9 |
| min | 9.2 | 5.8 | 6.4 | 7.1 |
| max | 25 | 43.8 | 28.3 | 56.6 |

Imaging examples show favorable characteristics. Both small subcentimeter lesions and diffuse metastatic disease involving different tissue types are shown.

FIG. 26 shows: MIR (A) and transaxial images (B-D) of a 70 year old patient with biochemical recurrence 1.5 years after radical prostatectomy (Gleason 8, pT2c, pN1). A single prostate cancer typical lesion with 5 mm diameter in right pelvis with high uptake of 18F-labelled PSMA-SIFA3 (7) is present. Malignant nature of the lesion was verified by histopathology.

FIG. 27 shows: Set of images of an 80 year old patient with progressive advanced castration resistant prostate cancer (PSA 66.4 ng/ml). Images shows high uptake of 18F-labelled PSMA-SIFA3 (7) in different classes of prostate cancer lesions (local tumor, lymph node metastases, bone metastases, liver metastases). Lesions demonstrated are as small as 2 mm (arrows indicate representative, not all tumor lesions).

Clinical Application of $^{68}$Ga-Labelled PSMA-SIFA3 (7)

As a proof on concept investigation of a $^{68}$Ga-labelled SiFA substituted chelator-based PET tracers one subject with biochemical recurrence after radical prostatectomy (PSA 0.44 ng/ml, pT2c, pNO, Gleason 7b) underwent PET/MR 66 min after injection of 144 MBq $^{68}$Ga-labelled PSMA-SIFA3 (7). Uptake typical for recurrent prostate cancer is demonstrated in a 2 mm lymph node.

FIG. 28 shows proof of concept investigation of a $^{68}$Ga-labelled SiFA substituted chelator-based PET tracer.

Human PSMA-SIFA3 (7) Studies

1. Biodistribution and uptake in tumor lesions
   - (a) Maximum intensity projection from PET of a subject with normal biodistribution.

See FIG. 21.
   - (b) Average standardized uptake values in different tissues See FIG. 22.
   - (c) Average ratio standardized uptake values in different tissues See FIG. 23.
   - (d) Average standardized uptake values in different tumor types See FIG. 24.
2. Tracer retention in urinary bladder
   - (a) Average standardized uptake values of tracer retention in bladder See FIG. 25.
3. Clinical results for detection of tumor lesions and histopathological validation See FIGS. 26 and 27.
4. Clinical application of $^{68}$Ga-labelled PSMA-SIFA3 (7)

See FIG. 28.

The invention claimed is:

1. A compound having a structure according to formula

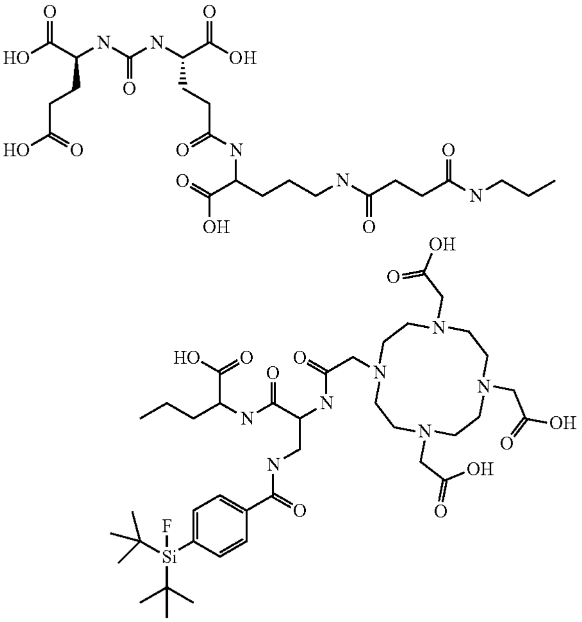

or a pharmaceutically acceptable salt and or individual isomer thereof, optionally containing a chelated radioactive cation.

2. The compound of claim 1 comprising a chelated radioactive cation.

3. The compound of claim 2, wherein the chelated radioactive cation is selected from the group consisting of $^{43}$Sc, $^{44}$Sc, $^{47}$Sc, $^{51}$Cr, $^{52}$mMn, $^{58}$Co, $^{52}$Fe, $^{56}$Ni, $^{57}$Ni, $^{62}$Cu, $^{64}$Cu, $^{67}$Cu, $^{66}$Ga, $^{67}$Ga, $^{68}$Ga, $^{89}$Zr, $^{90}$Y, $^{89}$Y, $^{99m}$Tc, $^{97}$Ru, $^{105}$Rh, $^{109}$Pd, $^{111}$Ag, $^{110}$ min, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{152}$Tb, $^{155}$Tb, $^{161}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At., $^{212}$Bi, $^{213}$Bi, $^{223}$Ra, $^{225}$Ac, $^{227}$Th, and a cationic molecule comprising $^{18}$F.

4. The compound of claim 3, wherein the chelated radioactive cation is selected from the group consisting of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, $^{227}$Th, and a cationic molecule comprising $^{18}$F.

5. The compound of claim 4, wherein the chelated radioactive cation is selected from the group consisting of $^{177}$Lu and $^{225}$Ac.

6. The compound of claim 5, wherein the chelated radioactive cation is $^{177}$Lu.

7. The compound of claim 5, wherein the chelated radioactive cation is $^{225}$Ac.

* * * * *